(12) United States Patent
Green et al.

(10) Patent No.: US 7,312,323 B2
(45) Date of Patent: Dec. 25, 2007

(54) ENZYMES AND POLYNUCLEOTIDES ENCODING THE SAME

(75) Inventors: Sol Green, Auckland (NZ); Ellen Friel, Auckland (NZ); Lesley Beuning, Huapai (NZ); Elspeth Macrae, Mt. Albert (NZ); Adam Matich, Palmerston North (NZ)

(73) Assignee: The Horticulture and Food Research Institute of New Zealand Limited, Auckland (NZ)

( * ) Notice: Subject to any disclaimer, the term of this patent is extended or adjusted under 35 U.S.C. 154(b) by 1 day.

(21) Appl. No.: 10/540,759

(22) PCT Filed: Dec. 24, 2003

(86) PCT No.: PCT/NZ03/00294

§ 371 (c)(1),
(2), (4) Date: Nov. 21, 2005

(87) PCT Pub. No.: WO2004/058814

PCT Pub. Date: Jul. 15, 2004

(65) Prior Publication Data

US 2006/0162008 A1    Jul. 20, 2006

(30) Foreign Application Priority Data

Dec. 24, 2002 (NZ) ..................... 523384

(51) Int. Cl.
| C07H 21/04 | (2006.01) |
| C12N 15/00 | (2006.01) |
| C12N 9/00 | (2006.01) |
| C12N 15/29 | (2006.01) |

(52) U.S. Cl. .................. 536/23.1; 536/23.2; 536/23.6; 435/183; 435/320.1

(58) Field of Classification Search ..................... None
See application file for complete search history.

(56) References Cited

U.S. PATENT DOCUMENTS 5,264,558 A    11/1993 Kim et al.
5,487,983 A    1/1996 Kim et al.

OTHER PUBLICATIONS

Guterman et al, The Plant Cell 14: 2325-2338, 2002.*
Bohlmann et al, Proc. Natl. Acad. Sci. USA 95, 4126-4133, 1998; *of record in IDS.*
Guo et al, Proc Natl Acad Sci 101(25):9205-9210, 2004.*
Hult and Berglund, Curr Opin Biotechnol 14:395-400, 2003.*
Aharoni et al "Terpenoid Metabolism in Wild-Type and TransgenicArabidopsis Plants," The Plant Cell, vol. 15, 2866-2884 (2003).
Altschul et al, "Gapped BLAST and PSI-BLAST: A New Generation of Protein Database Search Programs," Nucleic Acids Res. 25, 3389-3402 (1997).
Benedict et al, "The Cyclization of Farnesyl Diphosphate and Nerolidyl Diphosphate by a Purified Recombinant d-Cadinene Synthase," Plant Phys 125, 1754-1765 (2001).
Bohlmann, et al, "Plant terpenoid synthases: Molecular biology and phylogenetic analysis," Proc. Natl. Acad. Sci. U.S.A. 95, 4126-4133 (1998).
Bulow and Konig, "The role of germacrene D as a precursor in sesquiterpene biosynthesis: investigations of acid catalyzed, photochemically and thermally induced rearrangements," Phytochem 55, 141-168 (2000).
Cai et al, "A cDNA Clone for β-Caryophyllene Synthase from Artemisia annual," Phytochem 61, 523-529 (2002).
Cane et al., "Trichodiene Synthase: Mechanism-Based Inhibition of a Sesquiterpene Cyclase," Bioorg. Med. Chem. Lett. 9, 1127-1132 (1999).
Chamblee et al "Identification of Sesquiterpenes in Citrus Essential Oils by Cryofusing GC/FT-IR," J Essent Oil Res 9: 127-132 (1997).
Chang et al "Antimite Activity of Essential Oils and Their Constitutentsfrom Taiwania cryptomerioides," J Med Entom. 38:455-458 (2001).
Chen et al, "Cloning, Expression, and Characterization of (l)-d-Cadinene Synthase: A Catalyst for Cotton Phytoalexin Biosynthesis," Arch Biochem Biophys 324, 255-266 (1955).
Chen et al, "Cloning and Heterologous Expression of a Second (+)—Cadinene Synthase from Gossypium arboreum," J. Nat. Prod. 59 (10), 944-951 (1996).
Benfey et al, "Regulated Genes in Transgenic Plants," Science 244, 174-181 (1989).
Davis et al., "Cyclization Enzymes in the Biosynthesis of Monoterpenes, Sesquiterpenes, and Diterpenes," Top. Curr. Chem 209, 53-95 (2000).
Davis and Essenberg, "(+)-6-Cadinene is a Product of Sesquiterpene Cyclase Activity in Cotton," Phytochem 39, 553-567 (1995).
Davis et al, "Purification of (+)-fi-Cadinene Synthase, A Sesquiterpene Cyclase From Bacteria-Inoculated Cotton Foliar Tissue," Phytochem 41, 1047-1055 (1996).
Guterman et al "Rose Scent: Genomics Approach to Discovering Novel Floral Fragrance-Related Genes" Plant Cell, vol. 14, 2325-2338 (Oct. 2002).
van der Hoeven et al "Genetic Control and Evolution of Sesquiterpene Biosynthesis in Lycopersicon esculentum and L.hirsutum," Plant Cell 12 (11), 2283-2294 (2000).
Iijima et al "Characterization of Geraniol Synthase from the Peltate Glands of Sweet Basil," Plant Physiology 134, 1-10 (2004).
Iijima et al "The Biochemical and Molecular Basis for the Divergent Patterns in the Biosynthesis of Terpenes and Phenylpropenes in the Peltate Glands of Three Cultivars of Basil," Plant Physiology 136, 3724-3736 (2004).

(Continued)

*Primary Examiner*—Q. Janice Li
*Assistant Examiner*—Kevin K. Hill
(74) *Attorney, Agent, or Firm*—Greenlee Winner and Sullivan, PC

(57) ABSTRACT

The invention relates to a multifunctional germacrene-D synthase and a polynucleotide encoding it. Included also are genetic constructs, transgenic organisms, plant selection methods and biofermentation methods. The enzyme may be used to prepare germacrene-D and/or other sesquiterpenes such as germacrene-D, delta-cadinene, gamma-cadinene, gamma-muurolene, gamma-elemene, delta-elemene, elemol or germacrene-B.

8 Claims, 22 Drawing Sheets

OTHER PUBLICATIONS

Juteau et al "Antibacterial and antioxidant activities of Artemisia annua essential oil," Fitoterapia 73, 532-535 (2002).

Kawasaki et al, "Specific Regulation of Gene Expression by Antisense Nucleic Acids: A Summary of Methodologies and Associated Problems," Artific. Organs 20, 836-848 (1996).

Konig et al "The Sesquiterpene Constituents of the Liverwort Preissia Quadrata," Phytochem 43, 629-633 (1996).

Lange, et al, "Isoprenoid biosynthesis: The evolution of two ancient and distinct pathways across genomes," Proc. Natl. Acad. Sci. U.S.A. 97, 13172-13177 (2000).

Langenkamper et al, "Sucrose-Phosphate Synthase Steady-State mRNA Increases in Ripening Kiwifruit," Plant Mol Biol. 36, 857-869 (1998).

Lesburg, et al, "Managing and Manipulating Carbocations in Biology: Terpenoid Cyclase Structure and Mechanism," Curr Opin Struct Biol 8 695-703 (1998).

Llave et al, "Cleavage of Scarecrom-like mRNA Targets Directed by a Class of Arabidopsis miRNA," Science 297, 2053-2056 (2002).

Luehrsen "Intron Enhancement of Gene Expression and the Splicing Efficiency of Introns in Maize Cells," Mo. Gen. Genet 225, 81-93 (1991).

Maruyama et al., NCBI Entrez Nucleotide, Accession No. AF282875 (online) Jul. 25, 2001 (retrieved Apr. 6, 2004).

McIntyre "Strategies for the Suppression of Peroxidase Gene Expression in Tobacco. I. Designing Efficient Ribozymes," Transgenic Res. 5, 257-262 (1996).

Meng et al "Coordinated Accumulation of (+)-ä-Cadinene Synthase mRNAs and Gossypol in Developing Seeds of Gossypium hirsutum and a New Member of the cad1 Family from G. arboreum," J Nat. Prod. 62, 248-252 (1999).

Mozuraitis et al "Germacrene D Increases Attraction and Oviposition by the Tobacco Budwarm Moth Heliothis virescens," Chem Senses 27, 505-509 (2002).

Napoli et al, "Introduction of a Chimeric Chalcone Synthase Gene into Petunia Results in Reversible Co-Suppression of Homologous Genes In trans," Plant Cell 2, 279-289 (1990).

Needleman et al. "A General Method Applicable to the Search for Similarities in the Amino Acid Sequence of Two Proteins," J. Mol. Biol. 48; 443-453 (1970).

Niebel et al "Post-Transcriptional Cosuppression of β-1,3-Glucanase Genes Does not Affect Accumulation of Transgene Nuclear mRNA," Plant Cell 7 347-358 (1995).

Nishino et al, "Electroantennogram Responses of the American Cockroach to Germacrene D Sex Pheromone Mimic," J Insect Physiol 23, 415-419 (1977).

Prosser et al "(+)-(10R)-Germacrene A synthase from goldenrod, Solidago canadensis; cDNA isolation, bacterial expression and functional analysis," Phytochemistry 60, 691-702 (2002).

Schmidt et al "Mechanisms of the Biosynthesis of Sesquiterpene Enantiomers (+)- and (−)-Germacrene D in Solidago canadensis," Chirality 11:353-362 (1999).

Schmidt et al, "Biosynthese von (+)- und (−)-Germacren D in *Solidago canadensis*: Isolierung und Charakterisierung zweier enantioselektiver Germacren-D-Synthasen," Angewandte Chemie 110: 1479-1481 (1998).

Steele et al "Sesquiterpene Synthases from Grand Fir (Abies grandis)," J. Biol. Chem. 273, 2078-2089 (1998).

Steinmetz, A.A. et al., NCBI Entrez Nucleotide, Accession No. AY561842 (online) Mar. 21, 2004 (retrieved Apr. 6, 2004).

Steinmetz, A.A. et al., NCBI Entrez Nucleotide, Accession No. AY561843 (online) Mar. 21, 2004 (retrieved Apr. 6, 2004).

Steliopoulos et al, "Biosynthesis of the sesquiterpene germacrene D in *Solidago canadensis*: 13C and 2H labeling studies," Phytochemistry 60: 13-20 (2002).

Trapp & Croteau, "Genomic Organization of Plant Terpene Synthases and Molecular Evolutionary Implications," Genetics 158, 811-832 (2001).

Van Geldre et al, "Cloning and Molecular Analysis of Two New Sesquiterpene Cyclases from Artemisia annua L," Plant Sci. 158, 163-171 (2000).

Yoshihara and Hirose "The Sesquiterpenes of Dendropanax trifidus," Bull Chem Soc Jpn 51:3395-3396 (1978).

Yoshihara et al, "Germacrene D A Key Intermediate of Cadinene Group Compounds and Bourbonenes," Tetrahedron Letts 27: 2263-2264 (1969).

Zubay "In Vitro Synthesis of Protein in Microbial Systems," Annu Rev Genet 7, 267-287 (1973).

Benfey et al, "Regulated Genes in Transgenic Plants," Science 244, 174-181, 1989.

* cited by examiner

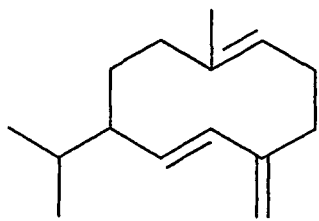
Germacrene D
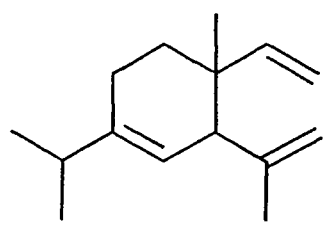
δ-elemene
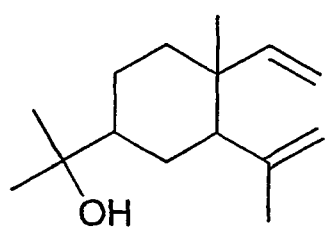
Elemol
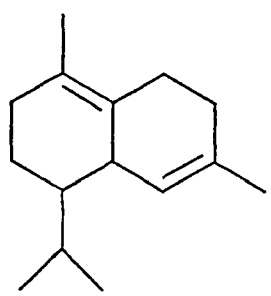
δ-cadinene
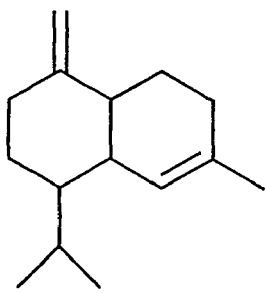
γ-cadinene
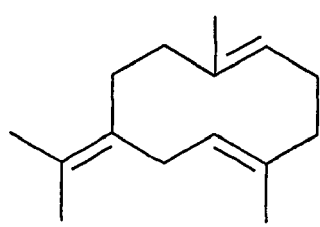
Germacrene B
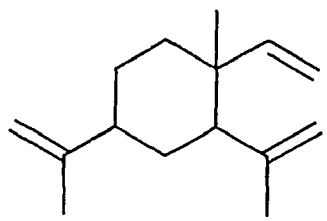
β-elemene
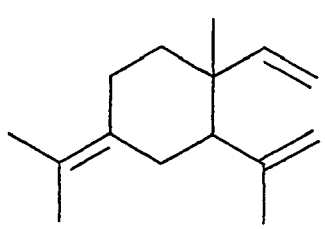
γ-elemene
FIGURE 1

FIGURE 3

```
  1 MQLPCAQALP IPTVTTTTSI EPPHVTRRSA NYHPSIWGDH FLAYSSDAME
 51 EEVINMEQQQ RLHHLKQKVR KMLEAAAEQS SQMLNLVDKI QRLGVSYHFE
101 TEIETALRHI YKTCDYHFDD LHTAALSFRL LRQQGYPVSC DMFDKFKNSK
151 GEFQESIISD VQGMLSLYEA TCLRIHGEDI LDEALAFTIT QLRSALPNLS
201 TPFKEQIIHA LNQPIHKGLT RLNARSHILF FEQNDCHSKD LLNFAKLDFN
251 LLQKLHQREL CEITRWWKDL NFAKTLPFAR DRMVECYFWI LGVYFEPQYL
301 LARRMLTKVI AMISIIDDIY DVYGTLEELV LFTDAIERWE ISALDQLPEY
351 MKLCYQALLD VYSMIDEEMA KQGRSYCVDY AKSSMKILVR AYFEEAKWFH
401 QGYVPTMEEY MQVALVTAGY KMLATSSFVG MGDLATKEAF DWVSNDPLIV
451 QAASVIGRLK DDIVGHKFEQ KRGHVASAVE CYSKQHGTTE EEAIIELDKQ
501 VTHSWKDINA ECLCPIKVPM PLLARVLNLA RVLYVIYQDE DGYTHPGTKV
551 ENFVTSVLID SMPIN*
```

FIGURE 4

>EST72838 (A. deliciosa variant of multifunctional germacrene D
synthase)
CTAAAATAGGCCAAGTGTGTAGGTTCATCTCTAGTTTTTCTCTTGAAAACTAAAATAGGCCAAGTG
TGTAGGTTCATCTCTAGTTTTTCTCTTGAAAACTAAAATAGGCCAAGTGTGTAGGTTCATCTCTAG
TTTTTCTCTTTAAATTAATCCTTCAACCCAGAAAAAAAACATGCAACTACCTTGTGCTCAAGCTTT
GCCAATACCAACTGTTACAACCAACACTAGTATTGAACCACCACATGTAACTCGTCGATCTGCAAA
TTATCATCCTAGCATTTGGGGAGATCATTTCCTCGCCTACTCTTCCGATGCTATGGAAGAAGAGGA
TATTAACATGGAACAACAACAACGACTTCATCACCTGAAACAAAAGGTGAGAAAAATGCTAGAGGC
AGCTGCTGAACAATCTTCACAGATGCTGAACCTCGTCGACAAAATCCAACGCTTAGGCGTGTCTTA
CCATTTTGAAACTGAGATCGAAACAGCTTTACGGCACATATACAAAACCTGTGATTACCATTTTGA
TGATCTCCACACTGCTGCTCTCTCTTTTCGGTTACTTAGACAACAAGGATATCCAGTTTCTTGTGA
TATGTTCGACAAATTCAAGAACAGCAAAGGTGAATTTCAAGAATCCATAATCAGCGATGTGCGAGG
AATGTTAAGTTTGTATGAAGCTACATGTCTAATGATACACGGAGAAGATATACTAGACGAAGCACT
AGCTTTTACCATCACTCAACTTCGGTCCGCATTGCCCAACTTAAGCACTCCTTTCAAGGAACAAAT
CATTCATGCTCTGAACCAGCCCATCCACAAGGGGTTGACAAGGCTCAATGCAAGGAGCCACATTTT
ATTTTTTGAACAGAATGATTGCCATAGCAAAGACCTTTTGAATTTCGCAAAATTAGATTTCAACTT
ATTACAAAAGTTGCACCAGAGGGAGCTATGTGAAATCACAAGGT.....................
..................................................................
..................................................................
.....................................................
.GAGATCAGTGCCTTGGATCAACTTCCAGAGTATATGAAACTATGTTATCAAGCACTTTTGGATGT
TTATAGTATGATTGATGAAGAGATGGCGAAGCAAGGAAGATCTTATTGCGTAGACTATGCAAAATC
TTCAATGAAAATTTTGGTTAGAGCATACTTCGAAGAAGCCAAATGGTTTCACCAAGGATATGTTCC
AACTATGAAGAGTATATGCAAGTTGCATTAGTAACCGCGGGTTACAAAATGCTTGCAACCTCTTC
CTTTGTTGGCATGGGAGAGTTGGCAACCAAAGAGGCCTTTGATTGGGTGTCAAATGATCCTTTAAT
TGTTCAAGCTGCATCAGTGATAGGCAGACTCAAGGATGACATTGTTGGCCACAAGTTTGAGCAAAA
GAGAGGGCACGTGGCGTCGGCTGTTGAATGCTACAGTAAGCAACATGGTACAACAGAGGAAGAGGC
TATTATTGAATTGTATAAACAAGTTACACATTCATGGAAAGACATGAACGCAGAGTGCCTCTGCCC
AACCAAGGTCCCAATGCCTCTTCTTGCGCGAGTTCTCAATCTTGCACGAGTGCTTTATGTTATATA
CCAGGATGCAGATGGCTACACTCATTCTGGAACCAAGGTCAAGAACTTTGTAACCTCAGTGCTTAT
CGATTCTATGCCAATCAATTAGAAAATTTAACAAGACACTGAAGTGGAGGTATAAATAAATTCAAA
AGTTGATTTAAAGTTGGGCTAGTGAACGGGGATTCTTACCATTAAGAGATATTCTTGCTAAAAAGC
AATTAATTCAATGCATTTCCAATAAAATAATTTAGCCAGCTGTTGTTCAAAAAAAA

FIGURE 5

>EST 80968 (*A. deliciosa* variant of multifunctional germacrene D synthase)
CTAAAATAGGCCAAGTGTGTAGGTTCATCTCTAGTTTTTCTCTTGAAAACTAAAATAGGCCAAGTG
TGTAGGTTCATCTCTAGTTTTTCTCTTTAAATTAATCCTTCAACCCAGAAAAAAAACATGCAACTA
CCTTGTGCTCAAGCTTTGCCAATACCAACTGTTACAACCAACACTAGTATTGAACCACCACATGTA
ACTCGTCGATCTGCAAATTATCATCCTAGCATTTGGGGAGATCATTTCCTCGCCTACTCTTCCGAT
GCTATGGAAGAAGAGGATATTAACATGGAACAACAACAACGACTTCATCACCTGAAACAAAAGGTG
AGAAAAATGCTAGAGGCAGCTGCTAAACAATCTTCACAGATGCTGAACCTCGTCGACAAAATCCAA
CGCTTAGGCGTGTCTTACCATTTTGAAACTGAGATCGAAACAGCTTTACGGCACATATACAAAACC
TGTGATTACCATTTTGATGATCTCCACACTGCTGCTCTCTTTTCGGTTACTTAGACAACAAGGA
TATCCAGTTTCTTGTGACATGTTCGGCAAATTCAAGAACTGCAAAGGTGAGTTTCAAGAATCCATA
ATCAGCGATGTGCGAGGAATGTTAAGCTTGTATGAAGCTACATGTCTAAGGATACGCGGAGAAGAT
ATACTAGACGAAGCACTAGCTTTTACCACGACTCAGCTTCAGTCTGCATTGCCCAACTTAAGCACT
CCTATCAAGGAACAAATCATTCATGCTCTGAACCAGCCCATCCACAAGTGGTTGACAAGGCTCGAC
GCAAGGCGCCACATTTTATTCTTCGAACAGAATGATTGCCATGGCAAAGACCTTTTGAATTTCGCA
AAATTAGATTTCAACTCGTTACAAAAGTTGCACCAGAGGGAGCTATGTGAAATCACAAGGTGGTGG
AAAGATCTGGATTTTGCCAAGAAACTACCTTTTGCCAGAGACAGAATGGTAGAGTGCTACTTCTGG
ATACTTGGGGTGTACTTTGAGCCCCAATATTTGCGTGCTAGGAGGATGCTAACCAAGGTGATTGCC
TTGACTTCCATTATCGATGACATCTACGATGTCTACGGTACCTTGGAAGAACTTGTTCTCTTCACT
GATGCAATTGAGAGGTGGGAAATTAGTGCCTTGGATAACCTTCCAGATTATATGAAACTATGTTAT
CAAGCACTTTTGGATGTTTATAGTATGATTGATGAAGAGATGGCCAAGCAAGGAAGATCTTATTGC
GTAGACTATGCAAAATCTTCAATGAAAATTTTGGTTAGAGCATACTTCGAAGAAGCCAAATGGTTT
CACCAAGGATATGTTCCAACTATGGAAGAGTATATGCAAGTTGCATTAGTAACCGCGGGTTACAAA
ATGCTTGCAACCTCTTCCTTTGTTGGCATGGGAGAGTTGGCAACCAAAGAGGCCTTTGATTGGGTG
TCAAATGATCCTTTAATTGTTCAAGCTGCATCAGTGATAGGCAGACTCAAGGATGACATTGTTGGC
CACAAGTTTGAGCAAAAGAGAGGGCACGTGGCGTCGGCTGTCGAATGCTACAGTAAGCAACATGGT
ACAATAGAGGAAGAGGCTATTATTGAATTGGATAAACAAGTTACACATTCATGGAAAGACATCAAC
GCAGAGTGCCTCTGCCCAATCAAGGTCCCAATGCCTCTTCTTGCGCGAGTTCTCAATCTTGCACGA
GTGCTTTATGTTATATACCAGGATGAAGACGGCTACACTCATTCTGGAACCAAGGTCAAGAACTTT
GCAACCTCAGTGCTTATCGATTCTATGCCAATCAATTAGAAAATGTAACAAGACACTGAAGTGGAG
GCATAAATAAATTCAAAAGTTGGCTTAAAGTTGGGCTAAAAAAAAAAAA >EST 304951 (*A. chinensis* variant of multifunctional germacrene D synthase)
ATCTTATTGCGTAGACTATGCAAAATCTTCAATGAAAAGTTTGGTTAGAGCATACTTCGAAGAAGC
CAAATGGTTTCACCAAGGATATGTTCCAACTATGGAAGAGTATATGCAAGTTGCAATAGTAACCGG
GGCTTACAAAATTCTTGCAACCACTTCCTTTGTTGGCATGGGAGAGTTGGCAACCAAAGAGGTCTT
TGATTGGGTGTCAAATGATCCTTTAATTGTTCAAGCTGCATCAATTGTTTCCAGACTCACGGATGA
CATTGTTGGCCACAAGTTTGAGCAAAAGAGAGGGCACGTGGCATCGGCGGTTGAATGCTACATGAA
GCAACATGGTACAACAGAGGAAGAGGCCATTGTTGAATTGTATAAGCAAGTTACAAATGCATGGAA
AGACATGAATGCAGAGTGCCTCTTCCCCACCAAGGTCCCAATGCCTCTTCTCGTGAGAGTTCTCAA
TCTTGCACGAGTGATTAATGTTCTATACAAGGATGAAGATGGCTACACTCATTCAAGAACCAAGGT
TAAGAAATTTGTGACCTCAGTGCTTGTAGATTTTGTGCCGATCAGCTAGCAAACGTTCCTCTCTAC
CACATGTTAATTAGTCTGCTTGCTAATGCAGTTTACTAATATGAAATTTAATAAATGCGTATTTTC
CAATAAAGGAATTTAAAAAAAAAAAA >EST 82293 (*Vaccinium corymbosum* variant of multifunctional germacrene D sythase)
GGAAGCCAAATGGTTTCATGAAGGTTATGTTCCGAGTATGGAAGAGTATATGAGAGTTGCACTGGT
TACCGGTGCTTACAAAATGCTTGCAACCACTTCTTTTGTTGGCATGGGGGATTTGGTGACCAAAGA
GGCCTTTGAATGGGTGTCAAGTGATCCTTTAATTGTTGAAGCTGCATCCGTGATTTGCAGACTCAT
GGATGATATGGCAGGCCACAAGTTTGAGCAAGAGAGAGGACACGTGGCTTCGGCAGTTGAATGCTA
CATGAAACAACATGGTGCAACACAAGAAGTGGTTCTTCTTGAATTTAAAAAAAGAGTTACAAATGC
ATGGAAAGACATGAACGCAGAGTGCCTCCGCCCAACTGCCGTTCCAATGCCTCTCCTCACCCGAGT
TCTCAATCTCGCACGAGTGATCAATGTTATATACAAGGATGAAGATGGGTACACTCATTCTGGAAC
AAAGCTCAAGAACTTTGTAATCTCAGTGCTTATCGATTCTGTGCCGATCAATTAGCAAACAGTAGT
CCTAACTTAAATAATCTGTTGGCTTATAACTTTATAAGTGTCGTGAAATGTTCTAGTGAACTTGGT
AAGGATGTATTTCCGATATGTAGCTCTATCTCCACTGTACGGTTGTAATCTTGCTCTCTTCTACTA
AGAAAGCTCATTAATCGCTGCTTAAAATGTAAAGCCAACTTGCTCAAGTTTATCGTCAAACAAGTT
CTGTTTTACGATTTTTGTTGGAAAAAAA

FIGURE 5 (continued)

>72838
MQLPCAQALPIPTVTTNTSIEPPHVTRRSANYHPSIWGDHFLAYSSDAMEEEDINMEQQQRLHHLK
QKVRKMLEAAAEQSSQMLNLVDKIQRLGVSYHFETEIETALRHIYKTCDYHFDDLHTAALSFRLLR
QQGYPVSCDMFDKFKNSKGEFQESIISDVRGMLSLYEATCLMIHGEDILDEALAFTITQLRSALPN
LSTPFKEQIIHALNQPIHKGLTRLNARSHILFFEQNDCHSKDLLNFAKLDFNLLQKLHQRELCEIT
R~~~~~~~~~~~~~~~~~~~~~~~~~~~~~~~~~~~~~~~~~~~~~~~~~~~~~~~~~~~~~~
~~~~~~~~~EISALDQLPEYMKLCYQALLDVYSMIDEEMAKQGRSYCVDYAKSSMKILVRAYFEEA
KWFHQGYVPTMEEYMQVALVTAGYKMLATSSFVGMGELATKEAFDWVSNDPLIVQAASVIGRLKDD
IVGHKFEQKRGHVASAVECYSKQHGTTEEEAIIELYKQVTHSWKDMNAECLCPTKVPMPLLARVLN
LARVLYVIYQDADGYTHSGTKVKNFVTSVLIDSMPIN

>80968
MQLPCAQALPIPTVTTNTSIEPPHVTRRSANYHPSIWGDHFLAYSSDAMEEEDINMEQQQRLHHLK
QKVRKMLEAAAKQSSQMLNLVDKIQRLGVSYHFETEIETALRHIYKTCDYHFDDLHTAALSFRLLR
QQGYPVSCDMFGKFKNCKGEFQESIISDVRGMLSLYEATCLRIRGEDILDEALAFTTTQLQSALPN
LSTPIKEQIIHALNQPIHKWLTRLDARRHILFFEQNDCHGKDLLNFAKLDFNSLQKLHQRELCEIT
RWWKDLDFAKKLPFARDRMVECYFWILGVYFEPQYLRARRMLTKVIALTSIIDDIYDVYGTLEELV
LFTDAIERWEISALDNLPDYMKLCYQALLDVYSMIDEEMAKQGRSYCVDYAKSSMKILVRAYFEEA
KWFHQGYVPTMEEYMQVALVTAGYKMLATSSFVGMGELATKEAFDWVSNDPLIVQAASVIGRLKDD
IVGHKFEQKRGHVASAVECYSKQHGTIEEEAIIELDKQVTHSWKDINAECLCPIKVPMPLLARVLN
LARVLYVIYQDEDGYTHSGTKVKNFATSVLIDSMPIN

>304951
YCVDYAKSSMKSLVRAYFEEAKWFHQGYVPTMEEYMQVAIVTGAYKILATTSFVGMGELATKEVFD
WVSNDPLIVQAASIVSRLTDDIVGHKFEQKRGHVASAVECYMKQHGTTEEEAIVELYKQVTNAWKD
MNAECLFPTKVPMPLLVRVLNLARVINVLYKDEDGYTHSRTKVKKFVTSVLVDFVPIS

>82293
EAKWFHEGYVPSMEEYMRVALVTGAYKMLATTSFVGMGDLVTKEAFEWVSSDPLIVEAASVICRLM
DDMAGHKFEQERGHVASAVECYMKQHGATQEVVLLEFKKRVTNAWKDMNAECLRPTAVPMPLLTRV
LNLARVINVIYKDEDGYTHSGTKLKNFVISVLIDSVPIN

FIGURE 6

ENZYMES AND POLYNUCLEOTIDES ENCODING THE SAME

CROSS-REFERENCE TO RELATED APPLICATIONS

This is a submission to enter National Stage under 35 U.S.C. § 371 for PCT Application No. PCT/NZ2003/000294, filed on Dec. 24, 2002 and published in English on Jul. 15, 2004 as WO 2004/058814 A1, which claims priorty to New Zealand patent application 523384, filed on Dec. 24, 2002, all of which are incorporated by reference in their entirety to the extent not inconsistent with the disclosure herewith.

TECHNICAL FIELD

The present invention relates to the enzyme multifunctional germacrene-D synthase and to polynucleotide sequences encoding the enzyme. The invention also relates to nucleic acid constructs, vectors and host cells incorporating the polynucleotide sequences. It further relates to the production of a multifunctional germacrene-D synthase and more specifically to the production of germacrene-D, gamma-muurolene and delta-and gamma-cadinene and minor quantities of other sesquiterpenes and their use in products such as an insect attractant/deterrent, anti-bacterial and anti-fungal agents, flavours and fragrances and other products. Germacrene-D, gamma muurolene and delta- and gamma-cadinene may also be used to produce further products with characteristic aromas useful as flavours and fragrances, or products that are useful as insect attractants/deterrents or antimicrobial agents.

BACKGROUND ART

Germacrene-D (FIG. 1) is a cyclic sesquiterpene hydrocarbon ($C_{15}H_{24}$; 7-iso-propyl-10-methyl-4-methylene-cyclodeca-5,10-diene) that is either constitutively present or induced in a wide range of plant species. Delta-Cadinene, gamma-muurolene and gamma-cadinene (FIG. 1) are cyclic sesquiterpene hydrocarbons that are either constitutively present or induced in a wide range of plant species.

The biosynthetic pathway for the sesquiterpenes branches off from the general terpenoid pathway, beginning with the allylic diphosphate ester farnesyl diphosphate (FDP, also called FPP) (Bohlmann, et al., Proc. Natl. Acad. Sci. U.S.A. 95, 4126-4133 (1998), Cane and Bowser, Bioorg. Med. Chem. Lett. 9, 1127-1132 (1999), Davis and Croteau, Top. Curr. Chem 209, 53-95 (2000)). Germacrene-D and delta-Cadinene can both be synthesised from FDP in a reaction that proceeds through a carbocation intermediate (FIG. 2) and are catalysed by the sesquiterpene synthases germacrene-D synthase (Guterman et al Plant Cell 14, 2325-2338 (2002)) and delta-cadinene synthase (Benedict et al Plant Phys 125, 1754-1765 (2001)) respectively. No gene has been isolated that has been demonstrated to produce significant quantities of gamma-muurolene or gamma cadinene. The pathway for sesquiterpene biosynthesis, the acetate/mevalonate pathway, is localised to the cytoplasm; in contrast to the pathways for monoterpene and diterpene biosynthesis, which occur in the chloroplast (Lange, et al., Proc. Natl. Acad. Sci. U.S.A 97, 13172-13177 (2000)). However recent labelling studies have shown that germacrene D in *Solidago canadensis* is formed predominantly via the methylerythritol phosphate pathway (Steliopoulos et al., Phytochemistry 60: 13-20 (2002)).

All known plant terpene synthases, however, whether monoterpene, sesquiterpene or diterpene, appear to be closely related. Similarities include the positioning of intron sequences (Trapp and Croteau, Genetics 158, 811-832 (2001)) and the presence of conserved sequences, such as an aspartate-rich DDXX(D,E) motif (Lesburg, et al., 8, 695-703 (1998)). This motif is involved in the binding of metal ions, usually $Mg^{2+}$, that are necessary for catalysis.

Germacrene-D is considered to be a key intermediate in the biosynthesis of many sesquiterpenes (Yoshihara et al., Tetrahed Lett 27: 2263-2364 (1969); Bülow and König, Phytochem 55, 141-168 (2000)). Furthermore, it has been shown to increase attraction of and oviposition by the tobacco budworm moth *Heliothis virescens* (Mozuraitis et al Chem Senses 27, 505-509 (2002)) and is also a sex stimulant for the male American cockroach (*Periplanata americana* L.) (Nishino et al., J Insect Physiol 23, 415-419 (1977)). Germacrene-D, as a component of certain essential oils, has also been shown to possess antibacterial properties (Juteau et al Fitoterapia 73, 532-535 (2002)). Germacrene D is also a major volatile in leaves of *Solidago* species (Prosser et al. Phytochemistry 60, 691-702 (2002)) and in lemon basil (Iijima et al. Plant Physiology 134, 1-10 (2004)). In general the (R)-(+)-enantiomer is found in lower plants, whereas the (S)-(–) enantiomer is found in higher plants, although there are plants where both enanfiomers exist (Schmidt et al., Angewandte Chemie 110: 1479-1481 (1998); Schmidt et al., Chirality 11:353-362 (1999)). To date a gene for germacrene-D synthase has been isolated only from rose (Guterman et al Plant Cell 14, 2325-2338 (2002)), which appeared to produce germacrene-D only. Its enantiomeric form is unknown.

Cadinene is the first intermediate in the conversion by delta-cadinene synthase of FDP to sesquiterpene phytoalexins in cotton (*Gossypium barbadense*) (Benedict et al Plant Phys 125, 1754-1765 (2001); Davis and Essenberg, Phytochem 39, 553-567 (1995); Davis et al., Phytochem 41, 1047-1055 (1996)), and is the precursor of deoxyhemigossypol and hemigossypol defense sesquiterpenes. Alpha-cadinol has been shown to be a potent miticide against house dust mites (Chang et al., J. Med Entom. 38:455-458 (2001)). To date four cDNAs for delta-cadinene synthase have been isolated from *Gossypium arboreum* and characterisation of at least one of these has been reported (Chen et al, Arch. Biochem Biophys 324, 255-266 (1995); Meng et al, J. Nat. Prod. 62, 248-252 (1999)). Although gamma-cadinene and gamma-muurolene are present widely in plants, no genes encoding for proteins that allow production of any of these compounds in any quantity have been discovered.

The applicants have identified a polynucleotide encoding a multifunctional germacrene-D synthase which facilitates the production of germacrene-D, gamma-muurolene and delta- and gamma-cadinene in biofermentation processes. By manipulation of the process conditions, the applicant obtained germacrene-D or germacrene-D with a mix of delta-cadinene, gamma-cadinene and gamma-muurolene in different ratios. Minor amounts of delta-elemene, germacrene B, elemol and delta-cadinene may be coproduced with germacrene-D. Minor amounts of alpha-cubebene, alphaylangene, alpha-copaene, beta-cubebene, isoledene, epibicyclosesquiphellandrene and alpha-cadinol/beta-eudesmol may be coproduced under acidic conditions with major quantities of gamma-muurolene, delta-cadinene, gammacadinene and germacrene-D. The polynucleotide can also be used to co-ordinately manipulate production of germacrene-D, delta-elemene, germacrene-B, elemol and delta-cadinene in transgenic plants to alter fragrance/flavour characteristics and/or plant pathogen and/or insect interactions. The gene can also be used as a marker in marker assisted breeding to discover plant material with altered germacrene-D, and delta-cadinene, delta-elemene, elemol or germacrene-B composition.

SUMMARY OF THE INVENTION

In a first aspect the invention provides an isolated polynucleotide encoding a multifunctional germacrene-D synthase.

In a further aspect the invention provides an isolated polynucleotide comprising the sequence shown in FIG. 3 (SEQ ID NO:1) or a fragment or variant thereof encoding a polypeptide with multifunctional germacrene-D synthase activity.

The polypeptides of the invention are multifunctional. They are capable of facilitating the conversion of FDP to a mixture of germacrene-D and gamma-muurolene, delta-and gamma-cadinene and other minor sesquiterpenes. Depending on the manner of trapping of the volatile products, the recombinant enzyme, can be used to obtain: germacrene D (plus minor amounts of other sesquiterpenes), or germacrene D with a mix of delta-and gamma-cadinene and gamma-muurolene (plus minor amounts of other sesquiterpenes)

In a further aspect, the invention provides an isolated polynucleotide encoding the polypeptide shown in FIG. 4 (SEQ ID NO:2) or encoding a variant or a fragment of that sequence which has a multifunctional germacrene-D synthase activity.

In a further aspect the invention provides an isolated multifunctional germacrene-D synthase polypeptide.

In yet a further aspect, the invention provides an isolated multifunctional germacrene-D synthase having the sequence shown in FIG. 4 (SEQ ID NO:2) or a fragment or variant thereof with similar multifunctional germacrene-D synthase activity.

The polypeptides of the invention are useful for in vitro preparation of germacrene-D and/or delta-cadinene, and/or gamma-muurolene, and/or gamma-cadinene. They may also be used for in vitro preparation of delta-elemene, germacrene B, gamma-elemene or elemol, or alpha-cubebene, alpha-ylangene, alpha-copaene, beta-cubebene, isoledene, epibicyclosesquiphellandrene and alpha-cadinol/beta-eudesmol.

In a further aspect the invention provides a vector comprising a polynucleotide of the invention.

In a further aspect the invention provides a genetic construct comprising an open reading frame polynucleotide encoding a polypeptide of the invention.

In yet a further aspect the invention provides a genetic construct comprising in the 5'-3' direction
(a) a promoter sequence; and
(b) an open reading frame polynucleotide encoding a polypeptide of the invention Preferably the genetic construct also comprises a termination sequence.

In another aspect the invention provides a genetic construct comprising in the 5'-3' direction
(a) a promoter sequence; and
(b) a polynucleotide which hybridizes to a polynucleotide encoding a polypeptide of the invention Preferably the genetic construct also comprises a termination sequence.

In a further aspect the invention provides a host cell comprising a genetic construct of the invention.

In still a further aspect, the invention provides a transgenic plant cell which includes a genetic construct of the invention.

In a yet further aspect, the invention provides a plant cell which has been modified to alter expression of a multifunctional germacrene-D synthase.

In addition the invention provides a transgenic plant comprising such cells.

In another aspect the invention provides a method of preparing germacrene-D, delta-cadinene, gamma-cadinene, gamma-muurolene, gamma-elemene, delta-elemene, elemol or germacrene B comprising the steps of
(a) culturing a cell which has been genetically modified with a polynucleotide of the invention to provide increased multifunctional germacrene-D synthase activity,
(b) providing the cell with farnesyl diphosphate or geranyl diphosphate if necessary; and
(c) separating the germacrene-D and/or delta-cadinene and/or and/or delta elemene and/or elemol and/or germacrene B, and/or gamma-cadinene, and/or gamma-muurolene, and/or gamma-elemene produced.

This method of the invention allows use of biofermentation as a convenient method for preparing the product.

Depending on the manner of trapping of the volatile products from the recombinant enzyme, it is possible to obtain germacrene D, elemol, delta-elemene, germacrene B and delta-cadinene, or germacrene D with a mix of delta cadinene, gamma muurolene and gamma-cadinene (plus minor amounts of other sesquiterpenes)

This gives us the opportunity to produce all these major compounds with the one protein. By varying the conditions in non plant production systems each compound may be obtained in a controlled manner.

In further aspect the invention provides a method for modulating the Germacrene-D and/or delta-cadinene and/or germacrene B and or elemol and/or delta-elemene, and/or gamma-cadinene, and/or gamma-muurolene, and/or gamma-elemene production of a plant, the method comprising: increasing or decreasing expression of multifunctional germacrene-D synthase wherein said increasing or decreasing is achieved by genetic modification to alter the expression of a gene encoding a multifunctional germacrene-D synthase.

In a further aspect the invention provides a method for modulating germacrene-D and/or delta-cadinene and/or germacrene B and or elemol and/or delta-elemene, and/or gamma-cadinene, and/or gamma-muurolene, and/or gamma-elemene production, in a plant, the method comprising of:
(a) introducing into the plant, a genetic construct of the invention; and
(b) transcriptionally expressing the polynucleotide in the plant.

In a further aspect the invention provides a method for modulating a multifunctional germacrene-D synthase production in a plant, the method comprising of
(a) introducing into the plant, a DNA genetic construct of the invention; and
(b) expressing a polypeptide of the invention in the plant.

In a further aspect the invention provides a method of selecting a plant with altered germacrene-D (and/or or other sesquiterpenes as above) content comprising the steps of:
(a) contacting polynucleotides from at least one plant with at least one polynucleotide comprising at least 15 contiguous nucleotides of the polynucleotide of the invention to assess the expression of the multifunctional germacrene-D synthase; and (b) selecting a plant showing altered expression.

Preferably the plant is an angiosperm, more preferably selected from Actinidiaceae and Ericaceae, most preferably from Actinidiaceae.

In yet a farther aspect the invention provides a method for preparing germacrene-D and/or other sesquiterpenes comprising:
(a) obtaining a polypeptide of the invention; and
(b) incubating farnesyl diphosphate in the presence of the polypeptide, and
(c) separating the germacrene D and and/or other compounds produced.

In a further aspect the invention provides an isolated polynucleotide comprising a sequence selected from the sequences of SEQ ID NO:1, SEQ ID NO:3, SEQ ID NO:4 and SEQ ID NO: 7 and SEQ ID NO: 9, or a fragment or variant thereof encoding a polypeptide with multifunctional germacrene-D synthase activity.

In a further aspect the invention provides an isolated polypeptide with multifunctional germacrene-D synthase activity comprising a sequence selected from SEQ ID NO: 2, SEQ ID NO:5, SEQ ID NO:6, SEQ ID NO:8 and SEQ ID NO:10, or a fragment or variant thereof.

BRIEF DESCRIPTION OF THE DRAWINGS

The present invention will be better understood with reference to the accompanying drawings in which:

FIG. 1 shows the structure of Germacrene D and other sesquiterpenes produced by EST 75565.

FIG. 3 shows the polynucleotide sequence (SEQ ID NO:1) that encodes a multifunctional germacrene-D synthase. The sequence was obtained from a cDNA library that was constructed using mRNA extracted from *Actinidia deliciosa* petals.

FIG. 4 shows the predicted amino acid sequence (SEQ ID NO:2) of a multifunctional germacrene-D synthase from *A. deliciosa* petals.

FIG. 5 shows the polynucleotide sequences of ESTs 72838 (SEQ ID NO:3), 80968 (SEQ ID NO:4), 304951 (SEQ ID NO:7) and 82293 (SEQ ID NO:9).

FIG. 6 shows the amino acid sequences of ESTs 72838 (SEQ ID NO:5), 80968 (SEQ ID NO:6), 304951 (SEQ ID NO:8) and 82293 (SEQ ID NO: 10).

DETAILED DESCRIPTION

Figure 2A:
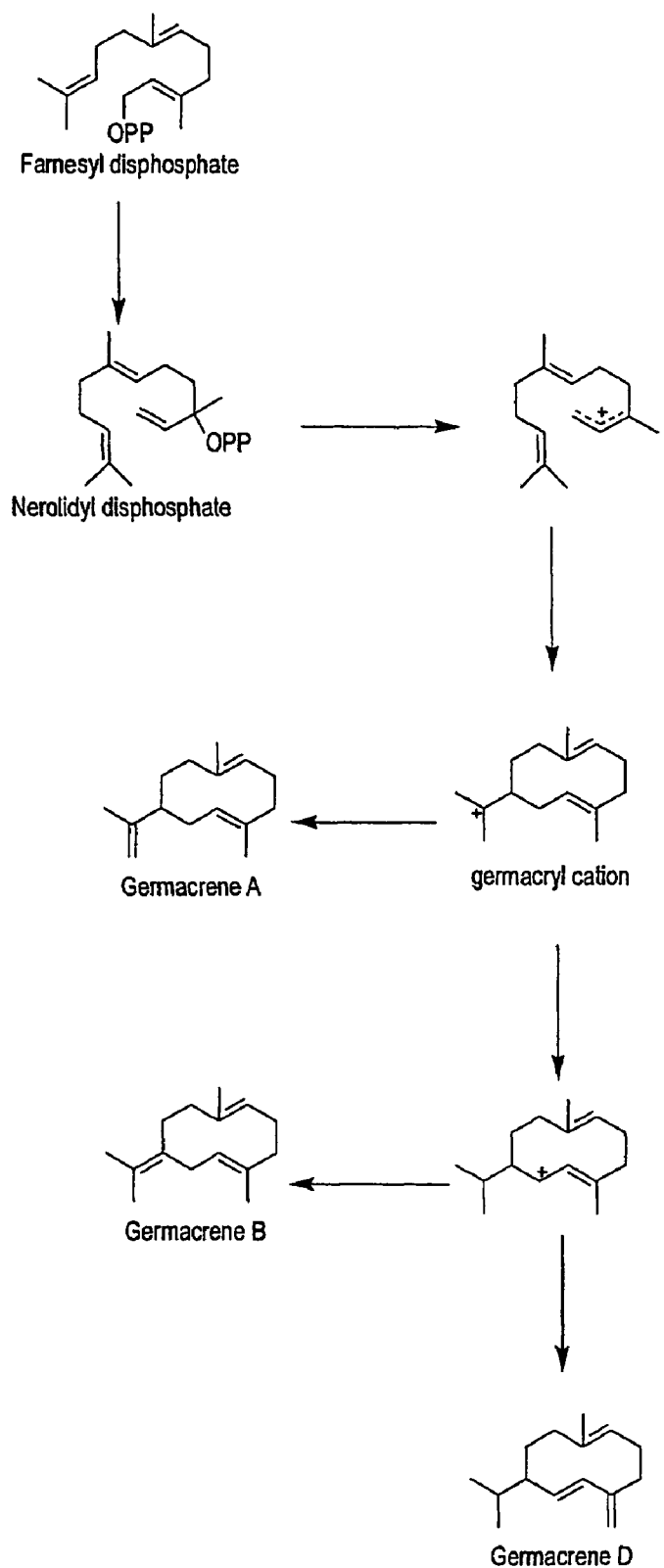
FIG. 2 shows (A) a pathway for the synthesis of germacrene D from FDP and (B) examples of acid catalysed rearrangement products of germacrene D.
Figure 2B:
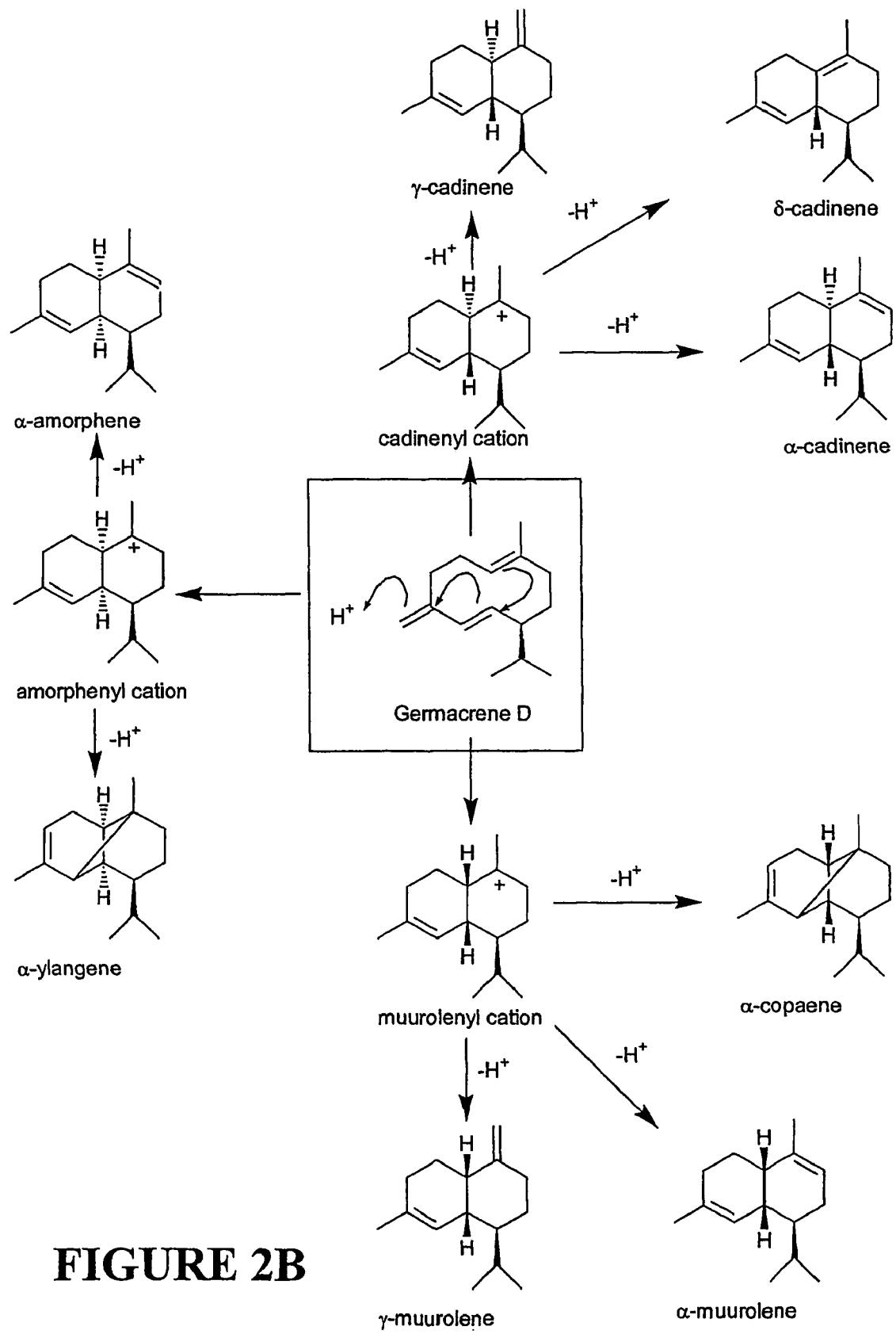

In one embodiment of the invention, cells genetically modified to exhibit a multifunctional germacrene-D synthase activity are used for the production of germacrene-D and/or delta-cadinene, and/or elemol and/or delta-elemene and/or germacrene B. While the cells may potentially be of any cell type that can be grown in culture, it is currently preferred to use bacteria or yeast cells for producing germacrene-D and/or delta-cadinene and other compounds (and oxidation products or derivatives). Preferred cells for use in the biofermentation processes of this embodiment are GRAS microbes; eg *E. coli, Lactobacillus* spp and other non-pathogenic bacteria or yeasts such as brewers yeast or fungi such as *Aspergillus niger*. Methods of capture of the produced compounds will be important in determining the composition eg. materials such as Chromasorb results predominantly in germacrene D, whereas silica-based matrices will result in predominantly gamma-muurolene and delta-cadinene.

Germacrene-D and its co- or by-products may be used as flavour and fragrance additives, an antimicrobial agent, as a pheromone for attracting or repelling insects. Delta-cadinene and its co- or by-products may be used as flavour and fragrance additives (eg baking goods, detergents, cosmetics, chewing gum), and as a pheromone repellent, particularly for cotton. Both compounds may be used as precursors for synthesis of other compounds of value.

In another aspect of the invention, the polynucleotides of the invention are used to prepare transgenic plants that over-express the multifunctional germacrene-D synthase in at least some parts of the plant. In this way the invention is used to impart fragrance to flowers, repel or attract insects (either as indicator plants, host plants, or alternative hosts) or impart an altered flavour to fruit or prevent disease in fruit, or to extract pharmaceutical products or animal or insect efficacious extracts.

In one particular aspect the polynucleotides of the invention are used in plants of the order Actinidiaceae and Ericaceae, particularly in the genus *Actinidia* and the genus *Vaccinium* to provide increased fragrance in flowers (or fruit). This aspect has particular use in kiwifruit and blueberries.

In another aspect polynucleotides of the invention are used to decrease multifunctional germacrene-D synthase activity in kiwi fruit. This may be achieved in several ways, for example by genetically modifying the kiwi fruit so that the multifunctional germacrene-D synthase polynucleotide is transcribed in an antisense orientation which results in decreased multifunctional germacrene-D synthase translation. Such fruit may then be more resistant to certain diseases and pests.

Altering the levels of germacrene-D and/or delta-cadinene and/or other components in flowers may alter attraction/repulsion of pollinators or may also affect invasion by pathogens.

In another aspect the invention provides a method useful in kiwifruit or blueberry breeding. Segments of the polynucleotide sequences of the invention may be used as probes to investigate the genetic makeup of candidate kiwifruit or blueberry varieties with respect to multifunctional germacrene-D synthase activity. The presence of high levels of polynucleotides encoding multifunctional germacrene-D synthase activity in the flowers or fruit of kiwifruit or blueberry may be used to identify kiwifruit or blueberries with altered fragrance or flavours.

Figure 3:
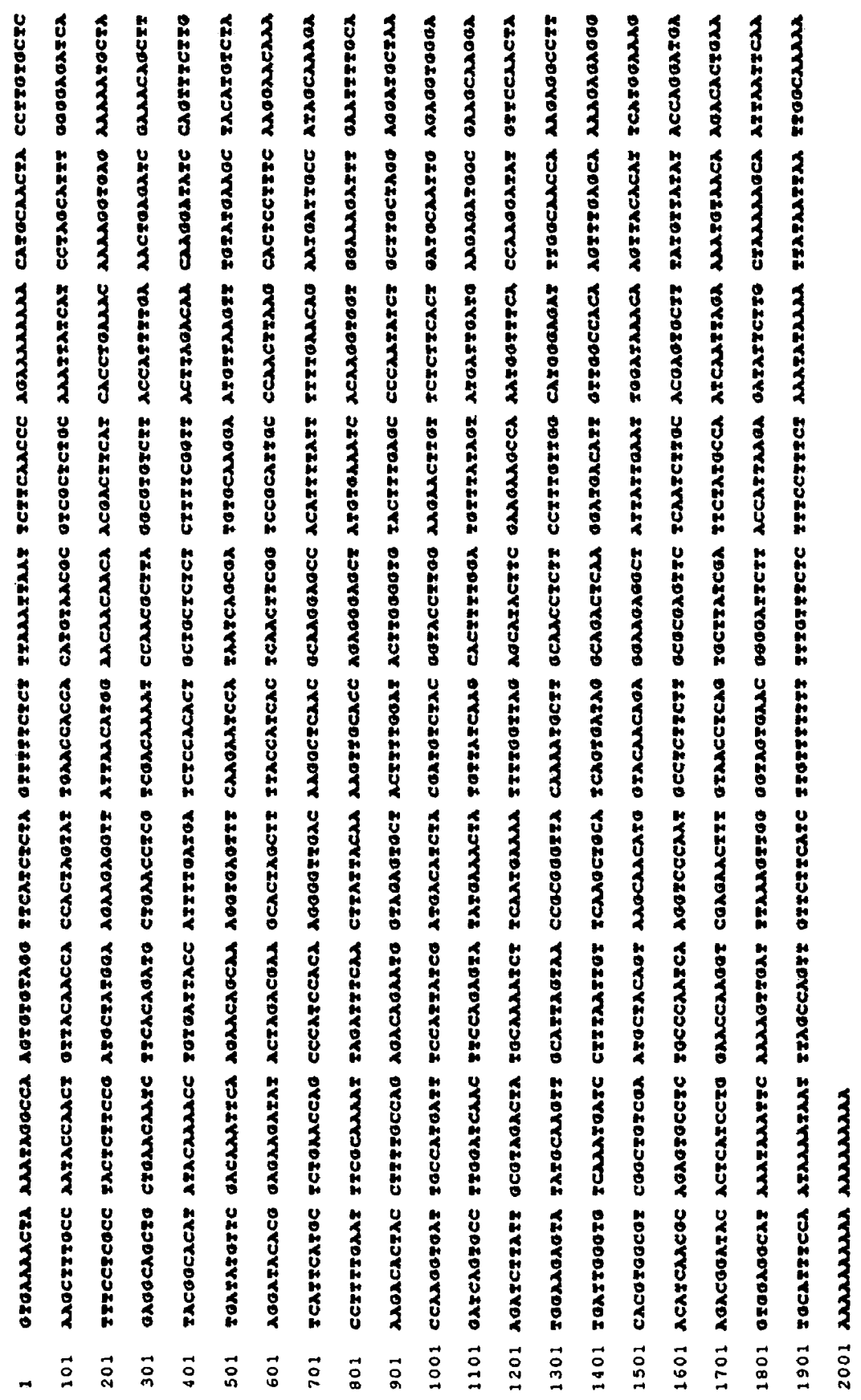

The amino acid sequence of one polypeptide, a multifunctional germacrene-D synthase from kiwifruit, and that of the polynucleotide sequence encoding it are given in FIGS. 4 and 3 respectively (SEQ ID NO:2 and SEQ ID NO:1). It will however be appreciated that the invention is not restricted only to the polynucleotide/polypeptide having the specific nucleotide/amino acid sequence given in FIGS. 3 and 4. Instead, the invention also extends to variants of the polynucleotide/polypeptide of FIGS. 3 and 4 which possess or encode a multifunctional germacrene-D synthase activity.

The term "polynucleotide(s)" as used herein means a single or double-stranded polymer of deoxyribonucleotide or ribonucleotide bases and includes DNA and corresponding RNA molecules, including hnRNA and mRNA molecules, both sense and anti-sense strands, and comprehends cDNA, genomic DNA and recombinant DNA, as well as wholly or partially synthesized polynucleotides. An hnRNA molecule contains introns and corresponds to a DNA molecule in a generally one-to-one manner. An mRNA molecule corresponds to an hnRNA and DNA molecule from which the introns have been excised. A polynucleotide may consist of an entire gene, or any portion thereof. Operable anti-sense polynucleotides may comprise a fragment of the corresponding polynucleotide, and the definition of "polynucleotide" therefore includes all such operable anti-sense fragments.

The term 'polypeptide(s)' as used herein includes peptides, polypeptides and proteins.

The phrase "variants with multifunctional germacrene-D synthase activity" is used in recognition that it is possible to vary the amino acid/nucleotide sequence of a polypeptide/polynucleotide while retaining substantially equivalent functionality. The equivalent can be, for example, a fragment of the polypeptide, a fusion of the polypeptide with another polypeptide or carrier, or a fusion of a fragment with additional amino acids.

An "isolated" polypeptide is a polypeptide that has been identified and separated or recovered to be largely free of components of its natural environment, (that is so that the polypeptide comprises at least 50% of the polypeptides from its natural environment, preferably at least 80%, more preferably at least 90%). The term "isolated" polypeptide includes polypeptides in situ within recombinant cells. However generally isolated polypeptides will be prepared by at least one purification step.

An "isolated" polynucleotide is a nucleotide molecule that is identified and separated from at least one contaminant polynucleotide with which it is ordinarily associated.

Variant polynucleotide sequences also include equivalent sequences, which vary in size, composition, position and number of introns, as well as size and composition of untranslated terminal regions. Variant polynucleotides also include those encoding functionally equivalent polypeptides.

It will be understood that a variety of substitutions of amino acids is possible while preserving the structure responsible for activity of the polypeptides. Conservative substitutions are described in the patent literature, as for example, in U.S. Pat. Nos. 5,264,558 or 5,487,983. It is thus expected, for example, that interchange among non-polar aliphatic neutral amino acids, glycine, alanine, proline, valine and isoleucine, would be possible. Likewise, substitutions among the polar aliphatic neutral amino acids, serine, threonine, methionine, asparagine and glutamine could be made. Substitutions among the charged acidic amino acids, aspartic acid and glutamic acid, could probably be made, as could substitutions among the charged basic amino acids, lysine and arginine. Substitutions among the aromatic amino acids, including phenylalanine, histidine, tryptophan and tyrosine are also possible. Such substitutions and interchanges are well known to those skilled in the art.

Equally, nucleotide sequences encoding a particular product can vary significantly simply due to the degeneracy of the nucleic acid code.

A polynucleotide or polypeptide sequence may be aligned, and the percentage of identical nucleotides in a specified region may be determined against another sequence, using computer algorithms that are publicly available. An exemplary algorithm for aligning and identifying the similarity of polynucleotide sequences is the BLASTN algorithm. The similarity of polypeptide sequences may be examined using the BLASTP algorithm. Both the BLASTN and BLASTP software are available on the NCBI anonymous FTP server (ftp://ncbi.nlm.nih.gov) under /blast/executables/. The BLASTN algorithm version 2.0.4 [Feb. 24, 1998], set to the default parameters described in the documentation of variants according to the present invention. The use of the BLAST family of algorithms, including BLASTN and BLASTP, is described at NCBI's website at URL http://www.ncbi.nlm.nih.gov/BLAST/newblast.html and in the publication of Altschul et al., Nucleic Acids Res. 25, 3389-34023 (1997).

The following running parameters are preferred for determination of alignments and similarities using BLASTN that contribute to E values (as discussed below) and percentage identity: Unix running command: blastall -p blastn -d embldb -e 10 -G 1 -E 1 -r 2 -v 50 -b 50 -I queryseq -o results; and parameter default values:
-p Program Name [String]
-d Database [String]
-e Expectation value (E) [Real]
-G Cost to open a gap (zero invokes default behaviour) [Integer]
-E Cost to extend a cap (zero invokes default behaviour) [Integer]
-r Reward for a nucleotide match (blastn only) [Integer]
-v Number of one-line descriptions (V) [Integer]
-b Number of alignments to show (B) [Integer]
-i Query File [File In]
-o BLAST report Output File [File Out] Optional
For BLASTP the following running parameters are preferred: blastall -p blastp -d swissprotdb -e 10 -G 1 -E 1 -v 50 -b 50 -I queryseq -o results
-p Program Name [String]
-d Database [String]
-e Expectation value (E) [Real]
-G Cost to open a gap (zero invokes default behaviour) [Integer]
-E Cost to extend a cap (zero invokes default behaviour) [Integer]
-v Number of one-line descriptions (v) [Integer]
-b Number of alignments to show (b) [Integer]
-i Query File [File In]
-o BLAST report Output File [File Out] Optional The "hits" to one or more database sequences by a queried sequence produced by BLASTN, BLASTP, or a similar algorithm, align and identify similar portions of sequences. The hits are arranged in order of the degree of similarity and the length of sequence overlap. Hits to a database sequence generally represent an overlap over only a fraction of the sequence length of the queried sequence.

The BLASTN algorithm also produces "Expect" or E values for alignments. The E value indicates the number of hits one can "expect" to see over a certain number of contiguous sequences by chance when searching a database of a certain size. The Expect value is used as a significance threshold for determining whether the hit to a database, such as the preferred EMBL database, indicates true similarity. For example, an E value of 0.1 assigned to a hit is interpreted as meaning that in a database of the size of the EMBL database, one might expect to see 0.1 matches over the aligned portion of the sequence with a similar score simply by chance. By this criterion, the aligned and matched portions of the sequences then have a 90% probability of being the same. For sequences having an E value of 0.01 or less over aligned and matched portions, the probability of finding a match by chance in the EMBL database is 1% or less using the BLASTN algorithm.

According to one embodiment, "variant" polynucleotides, with reference to each of the polynucleotides of the present invention, preferably comprise sequences having the same number or fewer nucleic acids than each of the polynucleotides of the present invention and producing an E value of 0.01 or less when compared to the polynucleotide of the present invention. That is, a variant polynucleotide is any sequence that has at least a 99% probability of being the same as the polynucleotide of the present invention, measured as having an E value of 0.01 or less using the BLASTN algorithm set at the parameters discussed above.

Variant polynucleotide sequences will generally hybridize to the recited polynucleotide sequence under stringent conditions. As used herein, "stringent conditions" refers to prewashing in a solution of 6×SSC, 0.2% SDS; hybridizing at 65° C., 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C. The variant polynucleotide sequences of the invention are at least 50 nucleotides in length.

Variant polynucleotides also include sequences which have a sequence identity of at least 60%, generally 70%, preferably 80%, more preferably 90%, even more preferably 95%, very preferably 98% and most preferably 99% or more to the nucleotide sequence given in the sequence listing herein.

In general, polypeptide sequences that code for the multifimctional germacrene-D synthases of the invention will be at least 60%, preferably 70%, and even 80%, 85%, 90%, 95%, 98%, most preferably 99% homologous or more with the disclosed amino acid sequence. That is, the sequence similarity may range from 60% to 99% or more. In addition the invention includes polynucleotide sequences encoding these amino acid sequences.

Also encompassed by the invention are fragments of the polynucleotide and polypeptide sequences of the invention. Polynucleotide fragments may encode protein fragments which retain the biological activity of the native protein. Alternatively, fragments used as hybridisation probes generally do not encode biologically active sequences. Fragments of a polynucleotide may range from at least 15, 20, 30, 50, 100, 200, 400 or 1000 contiguous nucleotides up to the full length of the native polynucleotide sequences disclosed herein.

Fragments of the polypeptides of the invention will comprise at least 5, 10, 15, 30, 50, 75, 100, 150, 200, 400 or 500 contiguous amino acids, or up to the total number of amino acids in the full length polypeptides of the invention.

Variant is also intended to allow for rearrangement, shifting or swapping of one or more nucleotides or domains/motifs (from coding, non-coding or intron regions) from genes (including terpene synthases) from the same or other species, where such variants still provide a functionally equivalent protein or polypeptide of the invention or fragment thereof.

It is, of course, expressly contemplated that homologs to the specifically described multifunctional germacrene-D synthase having the sequence of FIG. 4 (SEQ ID NO:2) exist in other plants. Such homologs are also "variants" as the phrase is used herein.

A polynucleotide sequence of the invention may further comprise one or more additional sequences encoding one or more additional polypeptides, or fragments thereof, so as to encode a fusion protein. Systems for such recombinant expression include, but are not limited to, mammalian, yeast, bacteria and insect systems.

DNA sequences from plants other than *A. deliciosa* which are homologs of the multifunctional germacrene-D synthase of FIG. 3 (SEQ ID NO:1) may be identified (by computer-aided database searching) and isolated following high throughput sequencing of cDNA libraries prepared from such plants. Alternatively, oligonucleotide probes based on the sequence of FIG. 4 (SEQ ID NO:2) can be synthesized and used to identify positive clones in either cDNA or genomic DNA libraries from other plants by means of hybridization or PCR techniques. Probes should be at least about 10, preferably at least about 15 and most preferably at least about 20 nucleotides in length. Hybridization and PCR techniques suitable for use with such oligonucleotide probes are well known in the art. Positive clones may be analyzed by restriction enzyme digestion, DNA sequencing or the like.

The polynucleotides of the present invention may be generated by synthetic means using techniques well known in the art. Equipment for automated synthesis of oligonucleotides is commercially available from suppliers such as Perkin Elmer/Applied Biosystems Division (Foster City, Calif.) and may be operated according to the manufacturer's instructions.

As a result of the identification of the polypeptides and polynucleotides of the invention multifunctional germacrene-D synthase activity may be modulated in plants.

Modulation may involve a reduction in the expression and/or activity (i.e. silencing) of the polypeptide.

Any conventional technique for effecting this can be employed. Intervention can occur post-transcriptionally or pre-transcriptionally. Further, intervention can be focused upon the gene itself or on regulatory elements associated with the gene and which have an effect on expression of the encoded polypeptide. "Regulatory elements" is used here in the widest possible sense and includes other genes which interact with the gene of interest.

Pre-transcriptional intervention can involve mutation of the gene itself or of its regulatory elements. Such mutations can be point mutations, frameshift mutations, insertion mutations or deletion mutations. These latter mutations include so called "knock-out" mutations in which expression of the gene is entirely ablated.

Examples of post-transcriptional interventions include co-suppression or anti-sense strategies, a dominant negative approach, or techniques which involve ribozymes to digest, or otherwise be lethal to, RNA post-transcription of the target gene.

Co-suppression can be effected in a manner similar to that discussed, for example, by Napoli et al. *Plant Cell* 2, 279-290 (1990) and de Carvalho Niebel et al. *Plant Cell* 7, 347-358 (1995). In some cases, it can involve over-expression of the gene of interest through use of a constitutive promoter. It can also involve transformation of a plant with a non-coding region of the gene, such as an intron from the gene or 5' or 3' untranslated region (UTR).

Anti-sense strategies involve expression or transcription of an expression/transcription product capable of interfering with translation of mRNA transcribed from the target gene. This will normally be through the expression/transcription product hybridising to and forming a duplex with the target mRNA.

The expression/transcription product can be a relatively small molecule and still be capable of disrupting translation from the mRNA. However, the same result is achieved by expressing the whole polynucleotide in an anti-sense orientation such that the RNA produced by transcription of the anti-sense oriented gene is complementary to all or part of the endogenous target mRNA.

Anti-sense strategies are described generally by Robinson-Benion et al. Methods in Enzymol 254, 363-375 (1995) and Kawasaki et al., Artific. Organs 20, 836-845 (1996).

Genetic constructs designed for gene silencing may include an inverted repeat. An 'inverted repeat' is a sequence that is repeated where the second half of the repeat is in the complementary strand, e.g.,

```
5'-GATCTA.........TAGATC-3'

3'-CTAGAT.........ATCTAG-5'
```

The transcript formed may undergo complementary base pairing to form a hairpin structure provided there is a spacer of at least 3-5 bp between the repeated regions.

Another approach is to develop a small antisense RNA targeted to the transcript equivalent to an mRNA (Llave et al., Science 297, 2053-2056 (2002) that could be used to target gene silencing.

The ribozyme approach to regulation of polypeptide expression involves inserting appropriate sequences or subsequences (eg. DNA or RNA) in ribozyme constructs (McIntyre Transgenic Res. 5 257-262 (1996)). Ribozymes are synthetic RNA molecules that comprise a hybridizing region complementary to two regions, each of which comprises at least 5 contiguous nucleotides of a mRNA molecule encoded by one of the inventive polynucleotides. Ribozymes possess highly specific endonuclease activity, which autocatalytically cleaves the mRNA.

Alternately, modulation may involve an increase in the expression and or activity of the polypeptide by over-expression of the polynucleotide, or by increasing the number of copies of the polynucleotide in the genome of the host.

To give effect to the above strategies, the invention also provides genetic constructs usually DNA constructs. The DNA constructs include the intended DNA (such as one or more copies of a polynucleotide sequence of the invention in a sense or anti-sense orientation or a polynucleotide encoding the appropriate ribozyme), a promoter sequence and a termination sequence (which control expression of the gene), operably linked to the DNA sequence to be transcribed. The promoter sequence is generally positioned at the 5' end of the DNA sequence to be transcribed, and is employed to initiate transcription of the DNA sequence. Promoter sequences are generally found in the 5' non-coding region of a gene but they may exist in introns (Luehrsen Mol. Gen. Genet 225, 81-93 (1991)) or in the coding region.

A variety of promoter sequences which may be usefully employed in the DNA constructs of the present invention are well known in the art. The promoter sequence, and also the termination sequence, may be endogenous to the target plant host or may be exogenous, provided the promoter and terminator are functional in the target host. For example, the promoter and termination sequences may be from other plant species, plant viruses, bacterial plasmids and the like. Preferably, promoter and termination sequences are those endogenously associated with the multifunctional germacrene-D synthase genes.

Factors influencing the choice of promoter include the desired tissue specificity of the construct, and the timing of transcription and translation. For example, constitutive promoters, such as the 35S Cauliflower Mosaic Virus (CaMV 35S) promoter, will affect the transcription in all parts of the plant. Use of a tissue specific promoter will result in production of the desired sense or antisense RNA only in the tissue of interest. With DNA constructs employing inducible promoter sequences, the rate of RNA polymerase binding and initiation can be modulated by external stimuli, such as light, heat, anaerobic stress, alteration in nutrient conditions and the like. Temporally regulated promoters can be employed to effect modulation of the rate of RNA polymerase binding and initiation at a specific time during development of a transformed cell. Preferably, the original promoters from the gene in question, or promoters from a specific tissue-targeted gene in the organism to be transformed are used. Other examples of promoters which may be usefully employed in the present invention include, mannopine synthase (mas), octopine synthase (ocs) and those reviewed by Chua et al. Science 244, 174-181 (1989).

The termination sequence, which is located 3' to the DNA sequence to be transcribed, may come from the same gene as the promoter sequence or may be from a different gene. Many termination sequences known in the art may be usefully employed in the present invention, such as the 3' end of the *Agrobacterium tumefaciens* nopaline synthase gene. However, preferred termination sequences are those from the original gene or from the target species to be transformed.

The DNA constructs of the present invention may also contain a selection marker that is effective in cells, to allow for the detection of transformed cells containing the construct. Such markers, which are well known in the art, typically confer resistance to one or more toxins. One example of such a marker is the NPTII gene whose expression results in resistance to kanamycin or hygromycin, antibiotics which are usually toxic to plant cells at a moderate concentration. Alternatively, the presence of the desired construct in transformed cells can be determined by means of other techniques well known in the art, such as PCR or Southern blots.

Techniques for operatively linking the components of the inventive DNA constructs are well known in the art and include the use of synthetic linkers containing one or more restriction endonuclease sites. The DNA construct may be linked to a vector capable of replication in at least one host system, additional to the intended destination host system for example, *E. coli*, whereby after each manipulation the resulting construct can be sequenced and the correctness of the manipulation determined.

The DNA constructs of the present invention may be used to transform a variety of plants including agricultural, ornamental and horticultural plants. In a preferred embodiment, the DNA constructs are employed to transform kiwifruit, blueberry, apple, banana, tomato, cotton, rose, olive, potato, carnation, mango, papaya, freesia, orchids, lisianthus, gerbera, grape plants for altered flavour, fragrance, disease or insect attraction characteristics. In addition the DNA constructs of the present invention may be used to transform medicinal plants such as *Solidago* species or plants used for biopharming such as tobacco. In a particularly preferred embodiment the plant is a carnation.

As discussed above, transformation of a plant with a DNA construct including an open reading frame comprising a polynucleotide sequence of the invention wherein the open reading frame is orientated in a sense direction can, in some cases, lead to a decrease in expression of the polypeptide by co-suppression. Transformation of the plant with a DNA construct comprising an open reading frame or a non-coding (untranslated) region of a gene in an anti-sense orientation will lead to a decrease in the expression of the polypeptide in the transformed plant.

It will also be appreciated that transformation of other non-plant hosts is feasible, including well known prokaryotic and eukaryotic cells such as bacteria (e.g. *E. coli*, *Agrobacterium*, *Lactobacillus*), fungi, insect, and animal cells is anticipated. This would enable production of recombinant polypeptides of the invention or variants thereof. The use of cell free systems (e.g. Roche Rapid Translation System) for production of recombinant proteins is also anticipated (Zubay Annu Rev Genet 7, 267-287 (1973)).

The polypeptides of the invention produced in any such hosts may be isolated and purified from same using well known techniques. The polypeptides may be used in cell-free systems for enzymic synthesis of sesquiterpenes for flavouring or scent uses, or for use in pheromone or anti-microbial agents. Such compounds could be germacrene-D and/or delta-cadinene and/or gamma-cadinene, and/or alpha-cubebene and/or delta-elemene and/or alpha-ylangene and/or alpha-copaene and/or gamma-elemene and/or gamma-muurolene and/or selinadiene and/or alpha-muurolene and/or germacrene B, and/or delta-elemene and/or elemol and/or alpha-cadinol.

Techniques for stably incorporating DNA constructs into the genome of target plants are well known in the art and include *Agrobacterium tumefaciens* mediated introduction, electroporation, protoplast fusion, injection into reproductive organs, injection into immature embryos, high velocity projectile introduction, floral dipping and the like. The choice of technique will depend upon the target plant to be transformed.

Once the cells are transformed, cells having the DNA construct incorporated into their genome may be selected by means of a marker, such as the kanamycin resistance marker discussed above. Transgenic cells may then be cultured in an appropriate medium to regenerate whole plants, using techniques well known in the art. In the case of protoplasts, the cell wall is allowed to reform under appropriate osmotic conditions. In the case of seeds or embryos, an appropriate germination or callus initiation medium is employed. For explants, an appropriate regeneration medium is used.

In addition to methods described above, several methods are well known in the art for transferring DNA constructs into a wide variety of plant species, including gymnosperms angiosperms, monocots and dicots. The resulting transformed plants may be reproduced sexually or asexually, using methods well known in the art, to give successive generations of transgenic plants.

The nucleotide sequence information provided herein will also be useful in programs for identifying nucleic acid variants from, for example, other organisms or tissues, particularly plants, and for pre-selecting plants with mutations in multifunctional germacrene-D synthase genes or their equivalents which render those plants useful in an accelerated breeding program to produce plants in which the content of germacrene-D or delta-cadinene (and other cpds) and their derivatives is modulated. More particularly, the nucleotide sequence information provided herein may be used to design probes and primers for probing or amplification of multifunctional germacrene-D synthase encoding polynucleotides. An oligonucleotide for use in probing or PCR may be about 30 or fewer nucleotides in length Generally, specific primers are upwards of 14 nucleotides in length. For optimum specificity and cost effectiveness, primers of 16-24 nucleotides in length are preferred. Those skilled in the art are well versed in the design of primers for use in processes such as PCR.

If required, probing can be done with entire restriction fragments of the gene disclosed herein. Naturally, sequences based upon FIG. 3 (SEQ ID NO:1) or the complements thereof can be used. Such probes and primers also form aspects of the present invention.

Methods to find variants of the of polynucleotides of the invention from any species, using the sequence information provided by the invention, include but are not limited to, screening of cDNA libraries, RT-PCR, screening of genomic libraries and computer aided searching of EST, cDNA and genomic databases. Such methods are well known to those skilled in the art. Such variants are exemplified in Example 2.

The invention will now be illustrated with reference to the following non-limiting Examples.

EXAMPLES

Example 1

Plant material and volatile collection: *A. deliciosa* ([A. Chev] C. F. Liang et A. R. Ferguson var. *deliciosa* 'Hayward') flowers were taken at anthesis from vines grown in a HortResearch orchard at Te Puke New Zealand in 2003. Branches containing flowers were transported with stems in water, immediately after harvest. Whole flowers (at all stages of petal unfolding, and in good quality; 124.9 g) were picked just under the receptacle and placed into a 250 mL Quickfit® Erlenmeyer flasks which was fitted with a headspace adaptor with an air inlet and outlet. Volatiles were collected in duplicate onto 100 mg Chromosorb 105 adsorbent traps, which were fitted to the air outlet port of each adaptor. The volatiles were purged from the vessel onto the traps with clean air at 100 mL min$^{-1}$ for 60 minutes. The traps were stored at −15° C. for one week, and then subjected to GC-FID/MS analysis.

Whole flowers of the same plants were also harvested at anthesis in 2000. 18.6 g and 21 g of flowers from a mixture of developmental stages were placed in 2× Quickfit® Erlenmeyer flasks as above. Volatiles were collected onto a Chromosorb adsorbent trap in duplicate, after the system had been equilibrated for 30 min at room temperature (ca. 23° C.), by purging onto the trap with clean air at 25 mL min$^{-1}$ for 60 minutes. The trap was stored at −15° C. for one week and then analysed by GC-FD/MS. The same petals (1.99 g) were then extracted with pentane-ether (2 ml) and stored at −20° C. until analysed. The pentane (GPR, BDH) had been purified by distillation and by passing through a column of activated alumina. Pentane extracts were reduced by rotary evaporation and were dried by passing through a small column of anhydrous MgSO$_4$ before the volume was reduced to ca. 50 μL under a gentle stream of nitrogen. The extract was analysed by GC-FID/MS.

Whole flowers of *A. deliciosa var deliciosa* genotype 32-10-07a were also collected in 2000. 3.5 g of flowers from mixed developmental stages were placed in a Quickfit® Erlenmeyer flask as above. Volatiles were collected onto a Tenax TA adsorbent trap, after the system had been equilibrated for 30 min at room temperature (ca. 20° C.), by purging onto the trap with clean air at 20 mL min$^{-1}$ for 100 minutes. The trap was stored at −15° C. for two weeks and then analysed by GC-FID/MS.

GC-MS Analysis of dynamic headspace samples and pentane extracts: Volatile compounds were thermally desorbed from the headspace traps at 150° C. and were cryofocussed at the beginning of the GC column (Young, 1981). The column outlet was split between the GC (Hewlett Packard 5890) FID detector (for quantitation) and VG-70SE (VG-Micromass, Manchester, U.K.) mass spectrometer (for component identification) with an electron impact ionisation of 70 eV. Separations were carried out in a 30 m×0.32 mm i.d., 0.5 μm DBWax capillary column (J & W Scientific, Folsom, USA), starting at 30° C. for 6 min, increasing by 3° C. min$^{-1}$ to 102° C., 5° C. min$^{-1}$ to 210° C. and held for 5 min. Injector temperature was 210° C. The carrier gas was He at a flow rate of ~30 cm s$^{-1}$, and the FID and mass spectrometer transfer line were at 210° C. Quantification of compounds was carried out using an average detector response based on methyl butanoate, ethyl butanoate, hexanol and methyl benzoate. Components were identified by comparison with spectra in the mass spectral database (NIST 1998, Wiley 7 and an in-house database), retention indices (in-house database) and in some cases direct GC-MS comparison with authentic standards. Separations for the earlier 2000 samples were carried out in the same manner as above except the programme started at 30° C. for 6 min, increasing by 3° C. min$^{-1}$ to 102° C., 5° C. min$^{-1}$ to 190° C. and held for 5 min. Analysis of the pentane extract used a programme of 2 min at 40° C., 5° C. min$^{-1}$ to 200° C., 15° C. m$^{-1}$ to 240° C. and held for 20 min. For genotype 32-10-07a: the GC-MS was programmed to start at 30° C. for 2 min, increasing by 3° C. min$^{-1}$ to 50° C., 5° C. min$^{-1}$ to 130° C., 10° C. min$^{-1}$ to 240° C. and held for 2 min. Injector temperature was 240° C.

Figure 7:
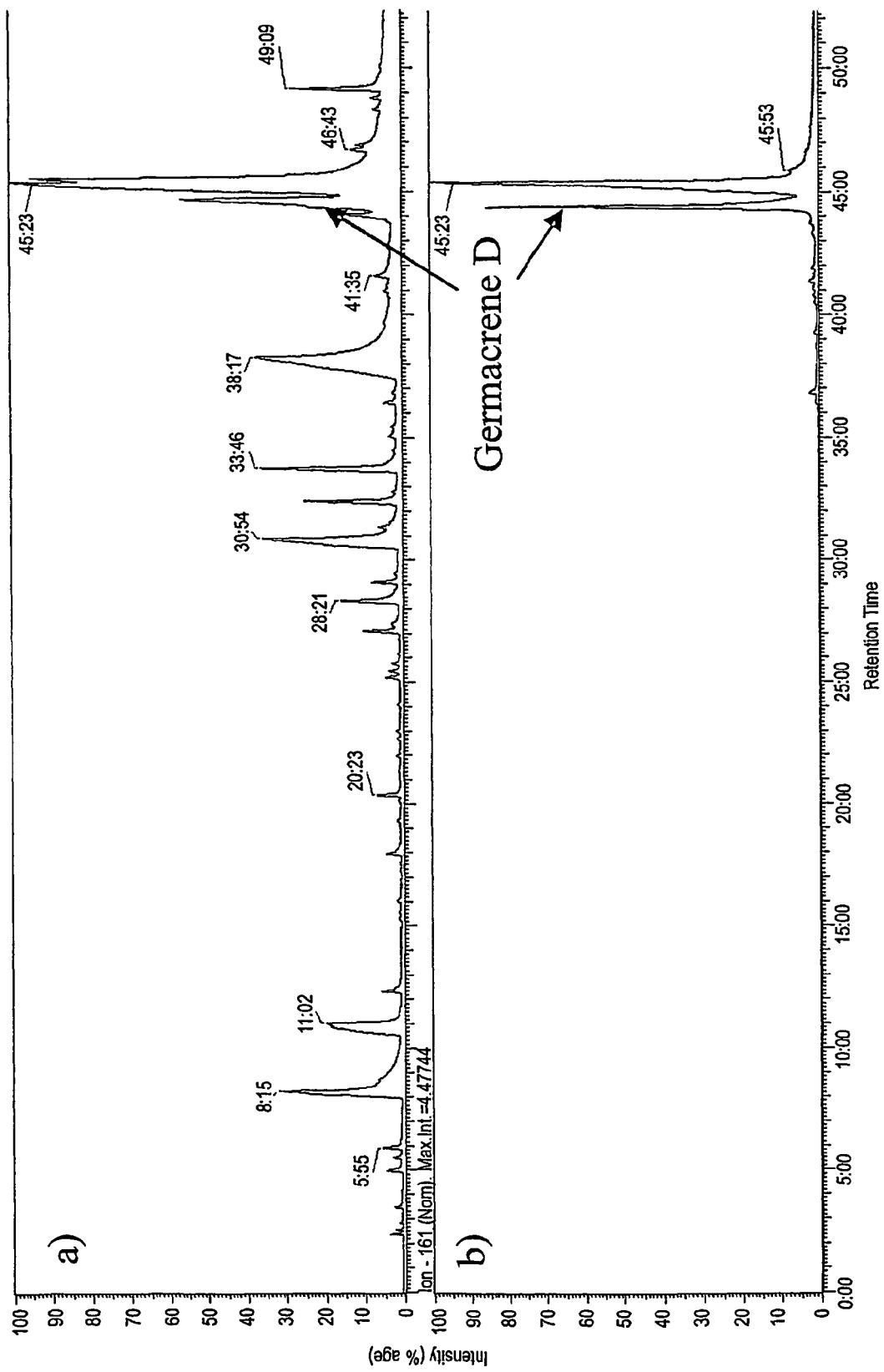
FIG. 7 shows the presence (a: total ion chromatogram, b: ion 161) of Germacrene D from the headspace volatiles in *Actinidia deliciosa* flowers.

Results:

Headspace analysis of volatiles emitted from kiwifruit flowers: Germacrene D is a commonly found constituent of plants and exists as one of two isomers. (S)-(−)-germacrene D mainly occurs in higher plants, whereas (R)-(+)-germacrene D is predominantly found in lower plants such as liverworts (König et at Phytochem 43, 629-633 (1996)). In the headspace of the *A. deliciosa* flowers analysed, germacrene D of unknown enantiomeric composition was detected, at an average concentration of 0.68 ng/g of petal tissue. In the total ion chromatogram, TIC (see FIG. 7*a*) the germacrene D is unresolved from the peak at 44.42 minutes but can be clearly identified by selecting ion 161 which is the base peak for Germacrene D (see FIG. 7*b*) from the total ion chromatogram. Germacrene D was identified as occurring at 44.22. Other major sesquiterpenes also show fragment ions at 161 and there is another major sesquiterpene in *A. deliciosa* flowers. This was identified as alpha-farnesene.

A number of minor sesquiterpenes were found in the flowers, these were delta-elemene, beta-elemene, germacrene B and elemol. Tentative identifications were also given to some trace level sesquiterpenes found, these were beta-cubebene, calarene (aka alpha-gujunene) and alpha-humulene. Three trace level sesquiterpenes remained unidentified. Some monoterpenes were present; these were beta-myrcene, alpha-terpinene, limonene and 2 isomers of ocimene. An identical experiment carried out previously in 2000 showed delta-elemene, beta-elemene, germacrene B, beta-citronellol and one unidentified sesquiterpene present in the flowers in addition to the higher levels of germacrene D and alpha-farnesene. Pentane extracts of this material showed germacrene D (592 ng/g), alpha-farnesene (23669 ng/g) and elemol (3353 ng/g) to be present. Both of these results confirmed Tenax trap extracts from another genotype of *A. deliciosa* ([A. chev] C. F. Liang et A. R. Ferguson var. deliciosa) flowers collected in a similar manner in 2000. These too showed Germacrene D and alpha-farnesene as the only major sesquiterpenes present.

Example 2

EST Library Construction and Analysis of Gene and Peptide Characteristics Including Variants and Phylogenetic Analysis Isolation of mRNA and construction of cDNA library: Total RNA was extracted from *A. deliciosa* petals by an adaptation of the method of Gomez and Gomez (Langenkamper, et al., 36, 857-869 (1998)). mRNA was purified from the total RNA by oligo(dT)-cellulose chromatography (Pharmacia) and was used to construct a Lambda ZAP-CMV (Stratagene) cDNA library according to the manufacturer's instructions. The cDNA-containing pBK-CMV plasmids were massed excised and used to transform *Escherichia coli* XLOLR (Stratagene). Plasmid was isolated from the XLOLR colonies and partially sequenced; the resulting cDNA sequences were then entered into the HortResearch EST database. All sequences on the database were compared to the NRDB90 database using the BLAST program (Altschul, Stephen F., Thomas L. Madden, Alejandro A. Schaffer, Jinghui Zhang, Zheng Zhang, Webb Miller, and David J. Lipman (1997), "Gapped BLAST and PSI-BLAST: a new generation of protein database search programs", Nucleic Acids Res. 25:3389-3402.). Putative terpene synthase cDNA sequences were identified by their similarity to known terpene synthases based on key protein motifs. A full-length sequence encoding a terpene synthase (EST75565) was identified. EST75565 was fully sequenced to determine that a functional cDNA suitable for in vitro expression studies had been isolated SEQ ID NO: 1, FIG. 3. Two other variants isolated from the *A. deliciosa* 'Hayward' petal cDNA library, ESTs 72838 and 80968 were fully sequenced also (SEQ ID NO:3 and SEQ ID NO:4, FIG. 5). The encoded amino acid sequences are shown in FIG. 4 (SEQ ID NO. 2) and FIG. 6 (SEQ ID NO: 5 and SEQ ID NO: 6).

Computational analysis of sequence information: Computational analysis was performed using the European Molecular Biology Open Software Suite (EMBOSS). (Rice et al, 2000). The Transeq program was used to determine the amino acid sequence and the Pepstats program was used for the determination of molecular weight and isoelectric point. Sequence identity and similarity was calculated using the pair wise alignment program Needle, which uses the algorithm of Needleman and Wunsch (J. Mol. Biol. 48; 443-453 (1970)). The default parameters were used (Gap extension penalty: 0.5 for any sequence; Gap opening penalty: 10 for any sequence). Amino acid sequence alignments were performed using the program CLUSTALW (Thompson et al., 1994), and trimmed and shaded using the program GeneDoc (Nicholas and Nicholas, 1997).

Results:

Sequence analysis of multifunctional germacrene D synthase: Sequencing of EST75565 revealed an insert size of 1995 base pairs excluding the poly (A) tail. The cDNA sequence had an ORF encoding 565 amino acids with a putative start codon 82 bases downstream of the 5' end. The molecular mass of EST75565 was calculated to be 65 kDa. The predicted amino acid sequence of the multifunctional germacrene D synthase does not contain a chloroplast-signalling peptide sequence (Emanuelsson, Nielsen, Brunak and von Heijne, 2000). These signalling peptides are typical of monoterpene and diterpene synthases and its absence is suggestive of it being a sesquiterpene synthase. As has been found for most other terpene synthases the predicted amino acid sequence of the multifunctional germacrene D synthase also contains a DDXX(D,E) motif (DDIYD) at amino acids 317 to 321 (FIG. 4, SEQ ID NO:2). This motif is involved in the binding of divalent metal ions necessary for catalysis. Multifunctional germacrene D synthase was also shown to contain the angiosperm sequiterpene consensus sequence GVYXEP (GVYFEP) (Cai et al Phytochem 61, 523-529 (2002)), from amino acids 292 to 297.

Bohlmann, Meyer-Gauen and Croteau (Proc. Natl. Acad. Sci. USA 95, 4126-4133 (1998)) compared the amino acid sequences of 33 terpene synthases and showed that there were seven absolutely conserved amino acid residues. Our multifunctional germacrene D synthase contains all seven of these absolutely conserved amino acids (FIG. 4). They also found that six positions were absolutely conserved for aromatic amino acids and four positions were absolutely conserved for acidic amino acids. In our multifunctional germacrene D synthase, four of the six aromatic positions and three of the four acidic positions are conserved.

Several variants were also isolated. EST 80968 is a full length homologue of EST 75565 (SEQ ID NO: 4) with 95% identity at the amino acid level (SEQ ID NO:6) and 97% similarity. It is predicted to form a protein of the same size. It contains the same GVYFEP motif from amino acids 292 to 297, and the DDIYD metal binding motif at amino acids 317 to 321. The ORF encoding 565 amino acids has a putative start codon 123 bases downstream of the 5' end. The EST is 1897 base pairs long. EST 72838 is a further full length homologue of EST 75565 with an exon deleted (SEQ ID NO:3). Where there are corresponding regions the proteins are 98% identical and 99% similar (SEQ ID NO:5). It does not contain the GVYFEP or DDIYD motifs as these are situated in the deleted exon. The 1817 base pair insert has a predicted ORF of 491 amino acids with a putative start codon 174 downstream from the ATG. Based on the untranslated regions the ESTs appear to be allelic variants of EST75565 (SEQ ID NO:1).

The predicted isoelectric point for multifunctional germacrene D synthase is 5.6 which is similar to the isoelectric point calculated for other sesquiterpene synthases. For example, two sesquiterpene synthases isolated from *Artemisia annua*, cASC34 and cASC125, have isoelectric points of 5.28 and 5.50, respectively (Van Geldre, et al., Plant Sci. 158, 163-171 (2000)).

BLAST searches revealed that the predicted amino acid sequence of germacrene/cadinene synthase is most similar to the rose germacrene-D synthase (Guterman et al, Plant Cell 14, 2325-2338 (2002)), having 59% identity and 74% similarity. Two sesquiterpene synthases from *Gossypium arboreum* (tree cotton), delta-cadinene synthase (Liang, Genbank, 1998), and delta-cadinene synthase isozyme A (Chen et al., J. Nat. Prod. 59 (10), 944-951 (1996)) with only two base pairs of difference, show the second highest similarity having 52% identity and 69% similarity at the amino acid level for both proteins. A sesquiterpene synthase from *Lycopersicon hirsutum* (tomato) of unknown function has the third highest similarity (van Der Hoeven et al., Plant Cell 12 (11), 2283-2294 (2000)), with 49% identity and 69% similarity. Specific regions of amino acid identity between these synthases are generally short (usually between 5 and 10 amino acids). The most notable homologies between all four proteins is a region immediately upstream of and including the putative angiosperm sesquiterpene synthase consensus sequence GVYFEP (Cai et al Phytochem 61, 523-529 2002). This includes a region of 13 or 14 identical amino acids for rose germacrene D synthase and the *Lycopersicon hirsutum* sesquiterpene synthase. The rose germacrene-D synthase also shares a region of 16 identical amino acids with EST 75565 from amino acids 314 to 329. Other regions of identity between these synthases include 4 amino acids from amino acid 167 to 170 and 4 amino acids from amino acid 265 to 268.

Homologues to EST 75565 were searched for among ESTs from other fruit species cDNA libraries. Two variants were found: EST 304951, a partially sequenced EST isolated from active *A. chinensis* 'Hort16A' meristems (FIG. 5 and 6, SEQ NO: 7 and SEQ NO: 8) and EST 82293, a partially sequenced EST from blueberry (*Vaccinium corymbosum*

'Duke' fruit (FIGS. 5 and 6, SEQ ID NO: 9 and SEQ ID NO: 10)). Both sequence fragments start after the DDIYD motif at amino acid 375 (*A. chinensis*) and amino acid 395 (blueberry).

Phylogenetic analysis using the full length protein against known characterized and putative terpene synthases clustered multifunctional germacrene D synthase with rose germacrene D synthase, and *Gossypium* cadinene synthases in terpene synthase family a. The separation between rose and *A. deliciosa* germacrene D synthases and the cadinene synthases was well supported (95% of the time segregating with 1000 bootstraps in a neighbour joining unrooted tree), and the separation between the two germacrene D synthases was also well supported (100% of the time segregating with 1000 bootstraps).

Example 3

Volatiles produced by bacterial cultures and purified protein Cloning into pGEM-T Easy and pET-30 vectors: For functional expression, a 1735 bp cDNA fragment encoding EST75565, excluding the initiating methionine, was amplified by PCR using the following primers: forward primer: 5'-GAA TTC CAA CTA CCT TGT GCT CAA GC-3' (SEQ ID NO:11); and reverse primer: 5'-CTC GAG CCT CCA CTT CAG TGT CTT G-3' (SEQ ID NO: 12) (restriction sites underlined). PCR reactions were carried out in a total volume of 50 mL with the following reagents: 1× Expand High Fidelity PCR buffer (Boehringer), 0.2 mM dNTP's (Boehringer), 0.2 µM of each primer, and 1.75 units of Expand High Fidelity polymerase (Boehringer). PCR cycling was 94° C. (4 min); 25 cycles of 94° C. (30 s), 55° C. (30 s), 72° C. (2 min); and a final extension period at 72° C. (10 min). PCR products were purified using the QIAquick PCR clean up system (Qiagen) following the manufacture's specifications and cloned into pGEM-T Easy (Promega). A pGEM-T Easy clone harbouring a potential cDNA was fully sequenced to check for PCR errors, then excised using Eco RI and Aho I and subcloned into the expression vector pET-30a, yielding plasmid pET-30a75565. pET-30a75565 was resequenced at the 5' end to ensure the inserted cDNA was in frame, and then transformed into *E. coli* BL21-CodonPlus™-RIL cells (Stratagene).

Characterization of multifunctional germacrene D synthase from bacterial extracts and purified recombinant protein: *E. coli* BL21-Plus™-RIL cells harbouring pET-30a75565 were grown overnight at 37° C. in Lauria-Bertani media supplemented with 30 µg ml$^{-1}$ kanamycin and 34 µg ml chloramphenicol$^{-1}$. 5 mL aliquots of overnight culture were used to inoculate 4×300 mL of fresh 2× YT medium supplemented with 30 µg ml$^{-1}$ kanamycin and 34 µg ml$^{-1}$ chloramphenicol in 1 L baffled flasks. Cultures were grown at 37° C. with vigorous agitation to $A_{600}$=0.8, then removed to 4° C. to equilibrate to 16° C. before induction with 0.3 mM IPTG. Following induction, cultures were immediately transferred to a 16° C. incubator and allowed to grow for a further 24 hours with continuous agitation and then harvested by centrifugation (2000×g for 10 min). Pelleted cells were resuspended in 20 mL binding buffer (5 mM imidazole, 0.5 mM NaCl, 10 mM DTT, 20 mM Tris-HCl (pH 7.9). Cells were disrupted with 2 times exposure to 12,700 psi in a French Pressure Cell Press (American Instrument Co. Inc, Silver Spring, Md. USA) and then centrifuged at 10000×g for 15 min. 5 mL of supernatant was transferred to a 50 mL test-tube and adjusted to 10 mM $MgCl_2$ and 20 µM $MnCl_2$. FDP (or GDP) was added to a final concentration of 100 µM and the reaction mixture was incubated at 30° C. with shaking (110 rpm). Headspace volatiles were collected as below. The remainder of the extract (15 mL) was applied to a PD-10 gel filtration column (Amersham-Pharmacia Biotech) pre-equilibrated with binding buffer (DTT omitted). Eluent fractions were then pooled and purification of recombinant protein was carried out in a single step using immobilised metal affinity chromatography (IMAC) utilising the recombinant proteins hexa-histidine ($His_6$ or His) tag. The eluent was applied to a Hi-Trap Chelating HP column (Amersham-Pharmacia Biotech) charged with $Ni^{2+}$. Non-bound proteins were removed and recombinant protein was eluted following the manufacturer's specifications. 5 mL samples of the eluted protein were transferred to 50 mL test tubes and adjusted to 100 µM FDP (or GDP), 10 mM $MgCl_2$, 20 µM $MnCl_2$. Optimum activity conditions are described in Example 5. Headspace volatiles were collected as below. A 5 mL purified sample was also trapped without the addition of any precursors as a further control. Aliquots of the remaining protein fraction were stored at −80° C. in 20% glycerol until required for further analysis.

Electrophoresis and western analysis: Whole culture, His-purified and non His-purified protein extracts were analysed by SDS-PAGE. Protein bands were separated on a polyacrylamide gel comprising a 4% stacking layer and a 10% separation layer. Protein bands were either visualised using modified Neuhoff stain or were transferred on to Immobilin-P PVDF membrane (Millipore) using a Trans-Blot semi dry electrophoretic transfer cell (Bio Rad). Blotted proteins were incubated with Anti-$His_6$ monoclonal antibody (Roche) and then with Anti-Mouse IgG-AP (Stressgen) secondary antibody, and were detected using 1-STEP™ NBT/BCIP (Pierce) alkaline phosphatase detection reagent.

Protein quantification: The protein concentration of crude and partially purified protein extracts were determined using the Bio Rad Protein-Assay™ reagent according to the manufacturers specifications. The reactions were quantified at 595 nm with a SPECTROmax PLUS spectrophotometer (Molecular Devices) using bovine serum albumin (13SA) as a standard.

Headspace Trapping of Purified Protein

The headspace in the testubes was collected immediately after the addition of FDP (or GDP) and hexadecane (internal standard) using solid phase micro extraction (SPME). The SPME fibres (65 µm Carbowax®/DVB Supelco, Australia) were conditioned 30 min at 220° C. The background was analysed for contamination using GC-FID (HP5890) prior to use. The headspace volatiles were collected for ~20 hours at 30° C. with continuous agitation (110 rpm). Prior to analysis using a GC-FID/MS, the fibres were stored at ambient temperature in septum sealed glass vials.

GC-MS Analysis of SPME Fibre Samples

The volatiles were desorbed from the fibres in the GC injection port for 10 minutes at 220° C. for the Carbowax/DVB fibres. The GC system was equipped with a DB-Wax capillary column (J & W Scientific, Folsom, USA), 30 m×0.25 mm i.d., with a 0.5 µm film thickness. The carrier gas was helium at a flow rate of 30 cm s$^{-1}$. The GC oven was programmed to remain at 30° C. for 6 min, then to increase by 3° C. min$^{-1}$ to 102° C., followed by an increase of 5° C. min$^{-1}$ to 210° C., which was maintained for 11 min. The mass spectrometer operated in electron impact ionisation (EI-MS) mode at 70 eV with a scan range of 30-320 amu. Peak identification was carried out by comparison of sample spectra with those from NIST98, Wiley 7, and our own mass spectra libraries and was confirmed by retention indices of authentic standards and literature values (Davies 1998).

Semi-quantitative data was obtained by measuring sample peak area relative to hexadecane internal standard.

Dynamic Headspace Trapping and Pentane Extraction and Identification of Volatiles Produced by the Recombinant Multifunctional Germacrene D Synthase Protein.

Dynamic headspace methods were also used to collect the headspace volatiles from the purified extracts on to 100 mg Chromosorb 105 adsorbent traps. The protein was placed into 50 mL Quickfit® test tubes, which were fitted with a headspace adaptor with an air inlet and outlet. Volatiles were collected onto the Chromosorb 105 adsorbent traps, which were fitted to the air outlet port of each adaptor. The volatiles were purged from the vessel onto the traps with clean air at 50 mL min$^{-1}$ for 18 hours. The traps were stored at −15° C. for up to one week, and then subjected to GC-FIDIMS analysis. Finally, pentane extracts were taken from the purified extracts. An aliquot (2.5 ml) of pentane was added to the purified extracts and was left to extract for 18 hours. The pentane was removed and then concentrated with a stream of $N_2$ gas. This was then injected onto the GC-MS at 150° C.

Results

Western analysis: Western analysis confirmed the presence of a soluble expression product that was slightly larger (ca. 70 kDa) than the predicted 65 kDa for the native protein. This size difference can be attributed to a $His_6$ tag being present in the recombinant EST75565 expression product. This product was detected in both the bacterial and partially purified recombinant protein extracts. No equivalent bands were detected in any of the vector only control extracts.

Figure 8:
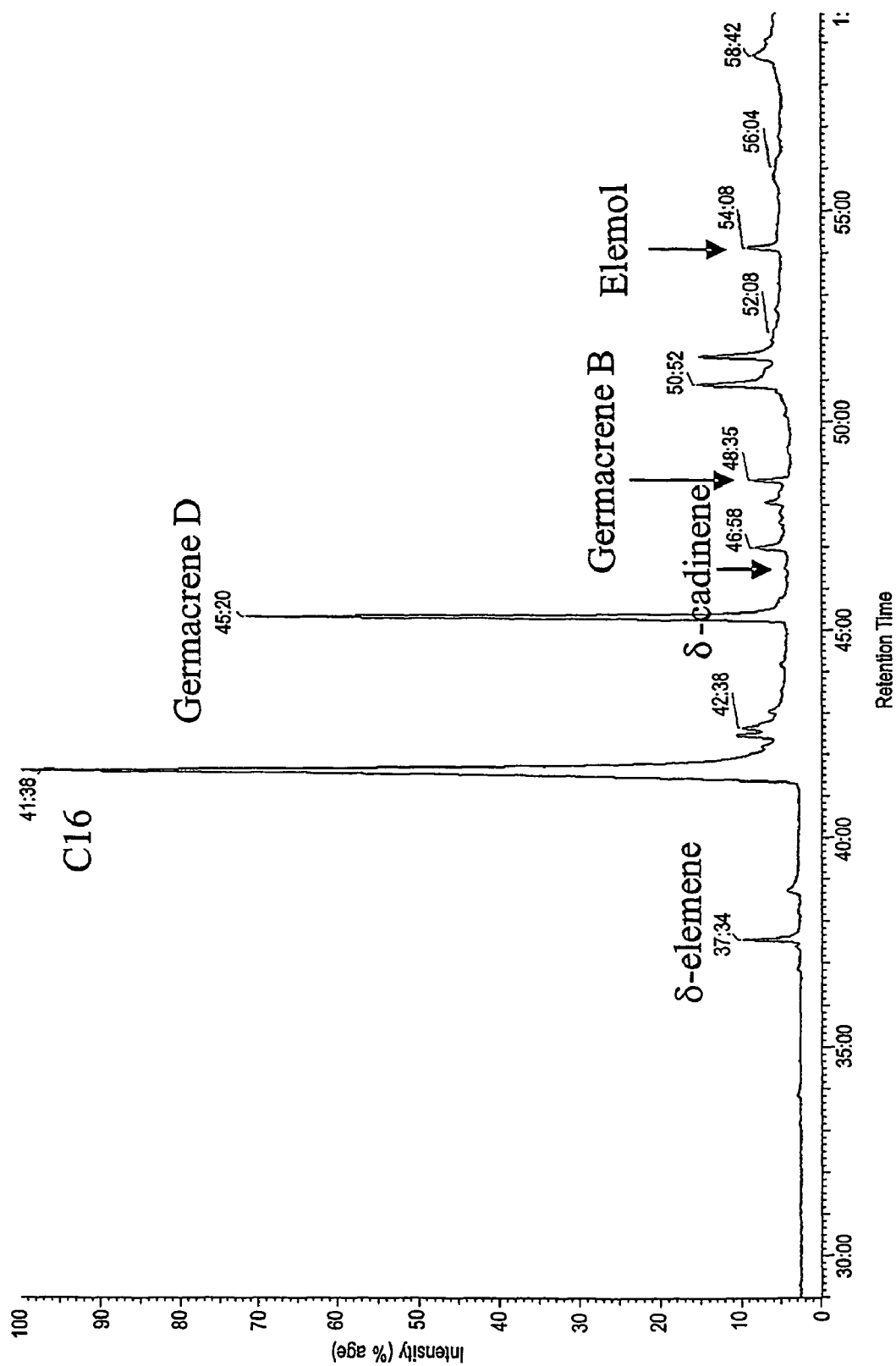
FIG. 8 shows a GC-MS trace of headspace above partially purified cell free extracts (optimum activity conditions) showing internal standard (C16) and sesquiterpene trapped on Carbowax®/DVB SPME fibres after 21 hours

Characterisation of Multifunctional Germacrene D Synthase:

When the purified protein sample which contained pET30/75565 and the FDP precursor was analysed for presence of compounds in the volatile headspace, a significant new peak was found, when compared to the control of empty vector protein and FDP. Library identification of this peak showed that it was germacrene D (see FIG. 8). When trapping using the Carbowax®/DVB fibres Germacrene-D (83%), a lesser amount of gamma-elemene (1.3%), delta-elemene (7%), germacrene-B (4.3%), elemol (4.2%) and delta-cadinene (0.5%/0) and gamma-muurolene (0.3%) were identified (see FIG. 8).

Figure 9:
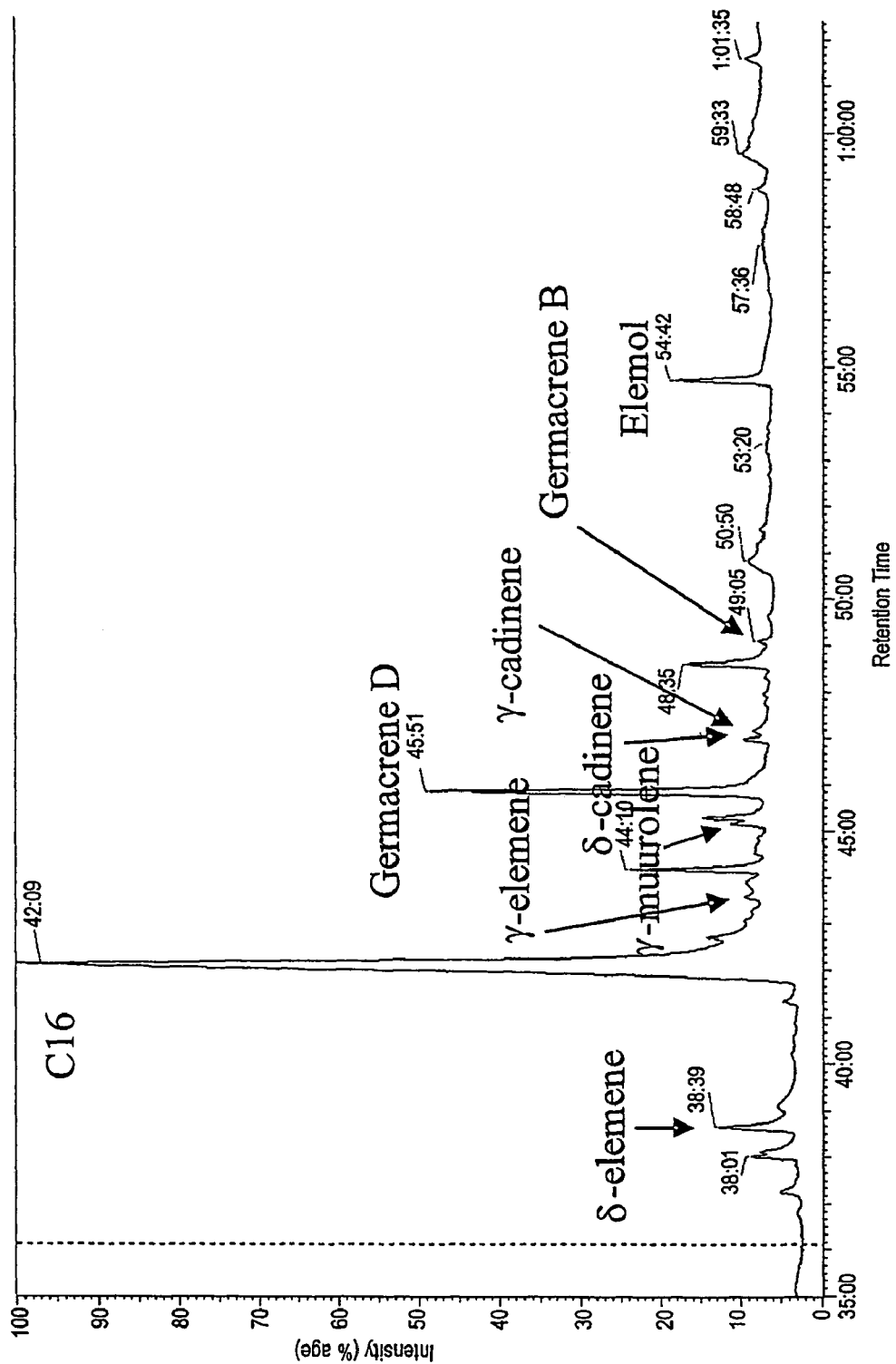
FIG. 9 shows a GC-MS trace of headspace above partially purified cell free extracts (optimum activity conditions) .showing internal standard (C16) and sesquiterpene products trapped on Chromosorb 105 cartridge after 18 hours.

The profile given by the dynamic headspace trapping method was quite similar to that of the Carbowax®/DVB SPME fibres, in that Germacrene D was the main product (54%) with smaller amounts of delta-elemene (15.5%), gamma-elemene (2.9%), Germacrene B (1.4%), delta-cadinene (3.9%) and elemol (16.6%) (FIG. 9). The levels of delta-elernene, gamma-elemene, delta-cadinene, gamma-muurolene and elemol were higher using this method but germacrene D was much lower than found with the SPME fibre. Gamnma-muurolene (3.8%) was at a much higher percentage in this sample and gamma-cadinene (1.8%) was also identified; it could not be identified in the Carbowax®/DVB SPME fibres. This difference in ratios is likely to be due to the chemical properties and specificity of the trapping matrix The decrease of germacrene D and concomitant increase in delta-elemene, gamma-elemene, delta-cadinene, gamma-muurolene and elemol may suggest that these compounds are rearrangements of germacrene D, in particular thermal, photochemical or acid catalysed. It is well established that thermal rearrangement of germacrene compounds leads to the corresponding elemene compounds (germacrene A rearranges to beta-elemene, germacrene B rearranges to gamma-elemene and germacrene C rearranges to delta-elemene), however, germacrene D does not thermally rearrange to an elemene structure. Germacrene A and C are very thermally labile, hence require low temperature GC-MS analysis (<100° C.) (Feger et al., Flavour and Fragrance Journal 15: 170-173 (2000)) to ascertain whether these products are due to rearrangement of the corresponding germacrenes. Although germacrene D is stable up to 180° C., germacrene D can thermally rearrange to beta-ylangene, beta-copaene, epsilon-muurolene and epsilon-amorphene as major products (Bülow and König, Phytochem 55: 141-168 (2000)). The comparison of the products on the Chromosorb cartridge (which was desorbed at 150° C.) and the Carbowax®/DVB SPME fibre (which was desorbed at 220° C.) does not reveal any differences which can be attributed to thermal rearrangement of germacrene D. In terms of the acid catalysed rearrangement, germacrene D completely rearranges to different sesquiterpenes by contact with weakly acidic media over a period of several days (Yoshihara et al., Tetrahedron Letts. 27: 2263-22264 (1969)), the main products of acid catalysed rearrangements are cadinene, muurolene and amorphene structures. Cadinenes are the predominant products due to a greater thermodynamic favorability of forming the cadinyl cation compared to the formation of the muurolenyl and amorphenyl cations. Although the acidity of the 2 matrices may have caused some rearrangement to the cadinene type structures, the extractions were introduced to the MS within a matter of hours, and germacrene D very often occurs with delta-cadinene in plants (Yoshihara and Hirose, Bull. Chem. Soc. Jpn, 51: 3395-3396 (1978)).

More light can be shed on the possibility of rearrangement of the products using pentane extraction. Pentane extraction does not subject the products to different pHs and can be injected into the GC-MS at specific temperatures such that potential for thermal rearrangement can be assessed.

TABLE 1

Thermal rearrangements and peak areas for pentane extracts from purified protein

| | Injection Port Temperature (° C.) | | |
| --- | --- | --- | --- |
| Compound | 125 | 150 Peak Area | 210 |
| Germacrene D | $4.22 \times 10^6$ | $4.90 \times 10^6$ | $3.91 \times 10^6$ |
| Germacrene B | $7.57 \times 10^5$ | $8.58 \times 10^5$ | $5.87 \times 10^5$ |
| Elemol | ca. $9 \times 10^4$ | ca. $1.4 \times 10^5$ | $5.75 \times 10^6$ |
| δ-Elemene | nd | nd | $9.05 \times 10^5$ | nd compound not detected.
The ca. values were for small elemol peaks that were not fully resolved and thus are only approximations.

TABLE 2

Thermal rearrangements and peak areas for pentane extracts from *Actinidia* flowers.

| | Injection Port Temperature (° C.) | | | |
| --- | --- | --- | --- | --- |
| Compound | 100 | 125 | 150 Peak Area | 210 |
| Germacrene D | $2.85 \times 10^7$ | $3.78 \times 10^7$ | $3.87 \times 10^7$ | $2.42 \times 10^7$ |
| Germacrene B | $5.0 \times 10^6$ | $7.40 \times 10^6$ | $1.0 \times 10^7$ | $3.92 \times 10^6$ |
| Elemol | nd | nd | ca. $8.4 \times 10^6$ | $3.78 \times 10^7$ |
| δ-Elemene | nd | nd | ca. $5.7 \times 10^5$ | $4.14 \times 10^6$ | nd compound not detected.
The ca. values were for small peaks that were not fully resolved and thus are only approximations.

In an experiment to test for thermal rearrangement, injections of pentane extract from purified protein were made at temperatures of 125, 150 and 210° C.; or pentane extract from *Actinidia* flowers were made at temperatures of 100, 125, 150 and 210° C. This demonstrated that while germacrene D remained at similar levels, elemol and delta-elemene increased in amount from non detectable (delta-elemene) or low levels (elemol) to significant quantities (Tables 1 and 2). Germacrene B modulated slightly in response to temperature shifts although no gamma-elemene was found as might be predicted. In addition the predicted precursor for delta elemene—germacrene C (Feger et al., Flavour and Fragrance Journal 15: 170-173 (2000)) was not detected at any time. Germacrene A was also not detected at any time. This suggests that these elemene-based compounds may be present in our experiments due to thermal rearrangements, although the source of rearrangement is unclear. Elemol may arise from further rearrangements of delta-elemene or from other elemene sources or from hedycaryol (Chamblee et al., J. Essent. Oil Res. 9: 127-132 (1997)). No GC-MS traces in any experiments indicated evidence for germacrene-C or for hedycaryol. Hence although the multifunctional germacrene D synthase may also produce germacrene C we have no evidence to support this other than the appearance of the elemene-based compounds at higher temperatures.

Example 4

Effect Of Trapping Method On Products Detected.

Expression and characterization of multifunctional germacrene D synthase from bacterial cultures: *E. coli* BL21-Plus™-RIL cells harbouring pET30a75565, or empty pET30a vector as a control, were grown overnight at 37° C. in Luria-Bertani media supplemented with 30 µg/mL kanamycin and 50 µg/mL chloramphenicol. A 500 mL aliquot of overnight culture was used to inoculate 50 mL of fresh 2× YT medium supplemented with 30 µg/mL kanamycin and 50 µg/mL chloramphenicol. The culture was grown at 37° C. with vigorous agitation to $A_{600}$=0.6 before induction with 0.3 mM isopropyl-β-D-thiogalactopyranoside (IPTG) and simultaneous addition of both farnesyl diphosphate (FDP) (100 µM) and hexadecane (required as an internal standard) or geranyl diphosphate (GDP) and hexadecane. The culture was immediately transferred to an incubator set at 16° C., 30° C. or 37° C. depending on the experiment The headspace in the vessels above the bacterial cultures was collected immediately after the addition of FDP (or GDP) and hexadecane (the internal standard) using solid phase micro extraction (SPME). The SPME fibres (65 µm PDMS/DVB, Supelco, Australia) were conditioned for 45 min at 260° C. The background was analysed for contamination using GC-FID (HP5890) prior to use. The headspace volatiles were collected for ~20 hours at 30° C. with continuous agitation (110 rpm). Prior to analysis using a GC-FID/MS, the fibres were stored at ambient temperature in septum sealed glass vials. The PDMS/DVB fibres were desorbed in the injector at 260° C.

As trapping whole cultures with PDMS/DVB fibres demonstrated the presence of compounds that had not been detected using the Carbowax®/DVB SPME fibres, other fibres were compared. The headspace of purified protein was also trapped using 85 µm Polyacrylate SPME and PDMS/DVB SPME fibres to allow comparison with the Carbowax®/DVB SPME fibres (Supelco, Australia). The polyacrylate SPME fibres were conditioned for 120 min at 300° C. and were desorbed in the injector at 300° C.

Results

Figure 10:
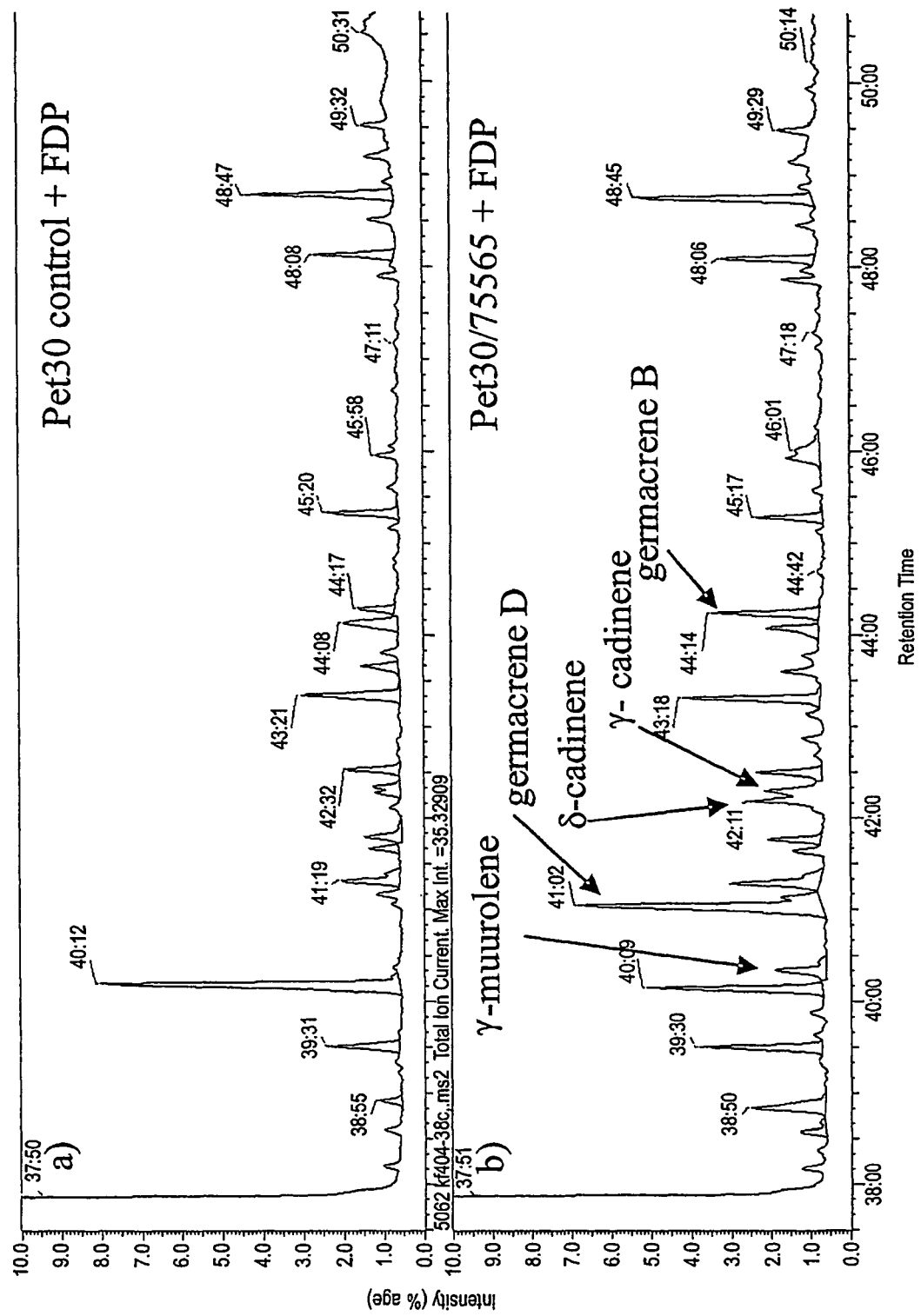
FIG. 10 shows a GC-MS trace of headspace above bacterial cultures harbouring (a) pET control vector or (b) pET 30/75565. FDP was added to both cultures. Trapping used PDMS/DVB fibres.

Bacterial Cultures:

Controls comprising *E. coli* BL21 cells transformed with pET-30a lacking the multifunctional germacrene-D synthase cDNA insert produced none of the compounds indicated by trapping of the purified protein with Carbowax®/DVB fibres (FIG. 10a). Trapping the whole cultures containing the multifunctional germacrene-D synthase cDNA insert using the PDMS/DVB fibres gave rise to different compounds and different ratios compared to those detected from the purified recombinant protein using Carbowax®/DVB fibres (compare FIG. 10b with FIG. 8). In particular germacrene D was present in a lower ratio and gamma-muurolene appeared at a much higher level.

In this experiment the production of germacrene-D was the largest (37.6%). Delta-elemene (12.5%), a lesser amount of cadinene, primarily delta isomer (10.9%) but also the gamma-isomer (6.3%), germacrene B (9.1%), gamma-muurolene (5.7%), and smaller quantities (less than 5%) of a range of sesquiterpenes: gamma-elemene, selina-3,7(11)-diene, alpha-humulene, alpha-cadinene, alpha-muurolene, alpha-amorphene, alpha-ylangene, alpha-cubebene, elemol and 3 unknowns were also produced.

In the empty vector control, there were some sequiterpenes produced, these were cis-alpha- and beta-bisabolene. There was no evidence of germacrene D or any of the products listed above. The internal standard indicated even efficiency of trapping for both the pet30/75565+FDP and pet30 control only+FDP samples. In addition, for the sample pet30/75565 with no added precursor, no germacrene D or any other sesquiterpenes were found.

Addition of geranyl diphosphate (GDP) to bacterial cultures did not result in the production of any monoterpenes. Germacrene-D was still produced, although at significantly lower levels to that exhibited with FDP addition. This is due presumably to the presence of bacterial FDP.

Purified Protein:

Compounds released from incubation of purified protein with FDP were similar to those in whole cultures, although there were less background (bacterial) compounds present. In contrast to the addition of GDP to bacterial cultures, purified protein did not produce any germacrene D. This reinforces the theory that the germacrene D found in the pet30/75565+GPP bacterial culture was only due to the presence of endogenous FDP in the bacteria.

Figure 11:
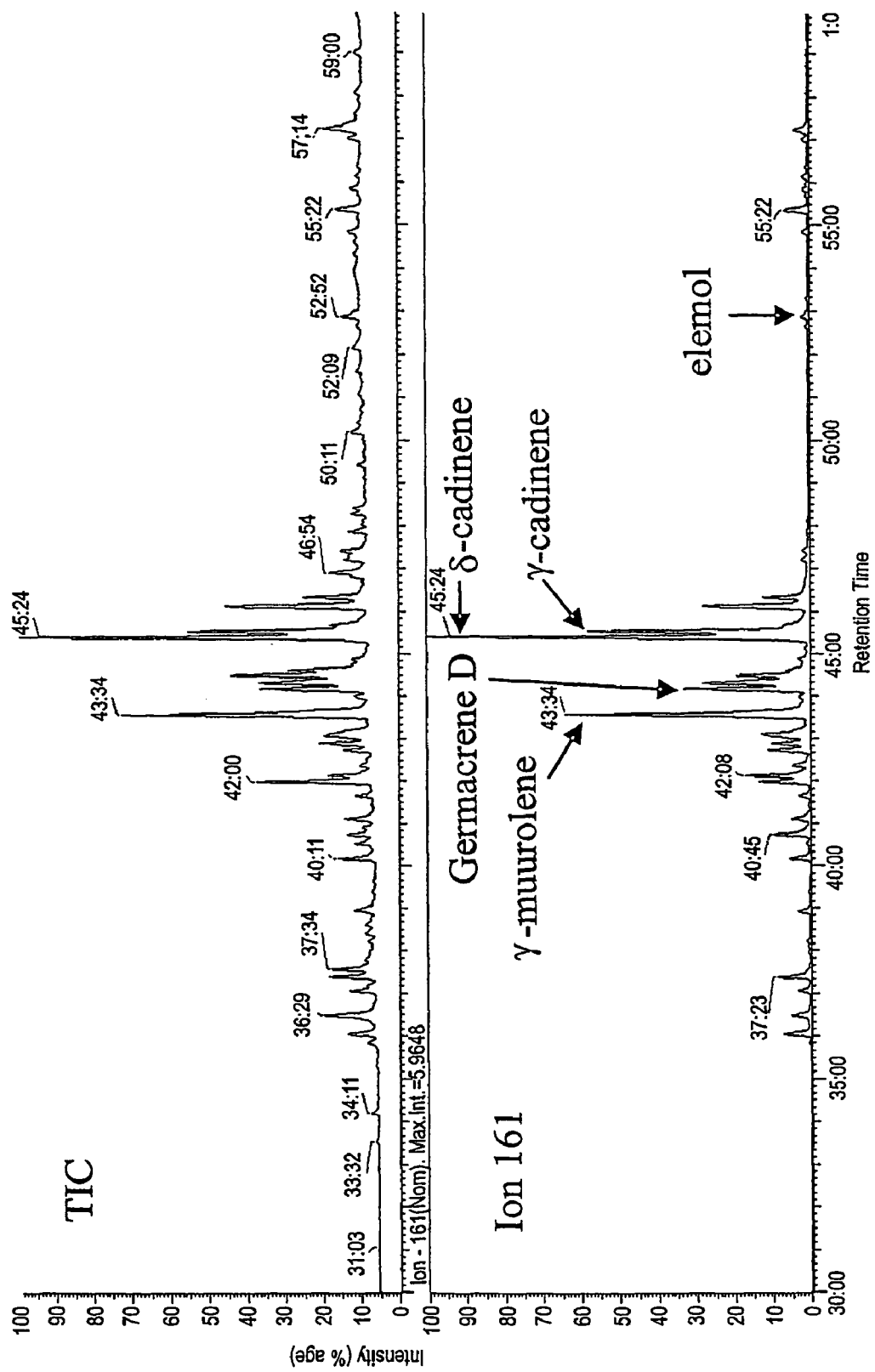
FIG. 11 shows the effect of trapping matrix on sesquiterpene composition, in particular sesquiterpene products from pET30/75565 purified protein extract+FDP trapped on PDMS/DVB SPME fibres after 24 hours.

Effect of trapping matrix on sesquiterpene composition: The enzyme produced different products depending on how the volatile products were extracted and analysed. When trapping with the PDMS/DVB fibre a range of sesquiterpene products were identified (FIG. 11).

Of the 42 sesquiterpenes or sesquiterpene alcohols present, 84.7% of the products could be identified. The major products were gamma-muurolene (14.8%), delta-cadinene (14.2%), eudesma-3,7(11)-diene (aka selina-3,7(11)-diene (7.3%)), gamma-cadinene (7.3%), alpha-muurolene (5.9%), gamma-elemene (4.9%), germacrene-D (4.6%). Other compounds which were identified as products were delta-elemene, isomers of cadinol (including alpha-, delta- and tau-), alpha-cadinene, alpha-humulene, alpha-selinene, alpha-copaene, alpha-cubebene, elemol, germacrene-B, alpha-amorphene, -alpha-ylangene, beta-elemene, beta-cubebene, isomers of eudesrnol and muurolol. Tentative identifications based on structure were given to epibicyclosesquiphellandrene and isoledene. Bicyclosesquiphellandrene is a known compound from acid catalysed rearrangement of delta-cadinene or through the muurolenyl cation from germacrene D (Bulow and Konig, Phytochem 55: 141-168 (2000)). 18 compounds remained unidentified, only 2 of these were in amounts over 1%, but these could not be resolved from each other hence no assignment could be made. Two of these eighteen compounds were sesquiterpene alcohols.

The polyacrylate fibre was found to be least efficient at extracting the sesquiterpenes, and showed low profiles of only germacrene D. The Carbowax®/DVB fibre showed germacrene D as the main product with smaller and similar amounts of delta-elemene, gamma-elemene, small amounts of beta-elemene, germacrene B, delta-cadinene and gamma-cadinene and elemol. Finally the PDMS/DVB fibre showed a wide range of products, with gamma-muurolene as the major product, followed by delta-cadinene, eudesma-3,7 (11)-diene, gamma-cadinene, alpha-muurolene, gamma-elemene and germacrene-D. There were also a host of other sesquiterpenes which could potentially be attributed to acid catalysed rearrangements of Germacrene D, which may also account for the decrease in intensity of the Germacrene D on this fibre. Elemol was also detected but at very low amounts.

The differences in the SPME coatings relates to the acidity, and these results illustrate that germacrene D is capable of rearranging under certain conditions (Yoshihara et al., Tetrahed Lett 27: 2263-2364 (1969)), acid catalysis being an important rearrangement mechanism.

However, headspace trapping is a sensitive method for collecting the volatile products of enzymes which allows for preconcentration on the sampling medium and comparison of the different products obtainable with different extraction methods shows the scope of usability for this enzyme, in that the products obtained can be manipulated by the extraction method.

Figure 12:
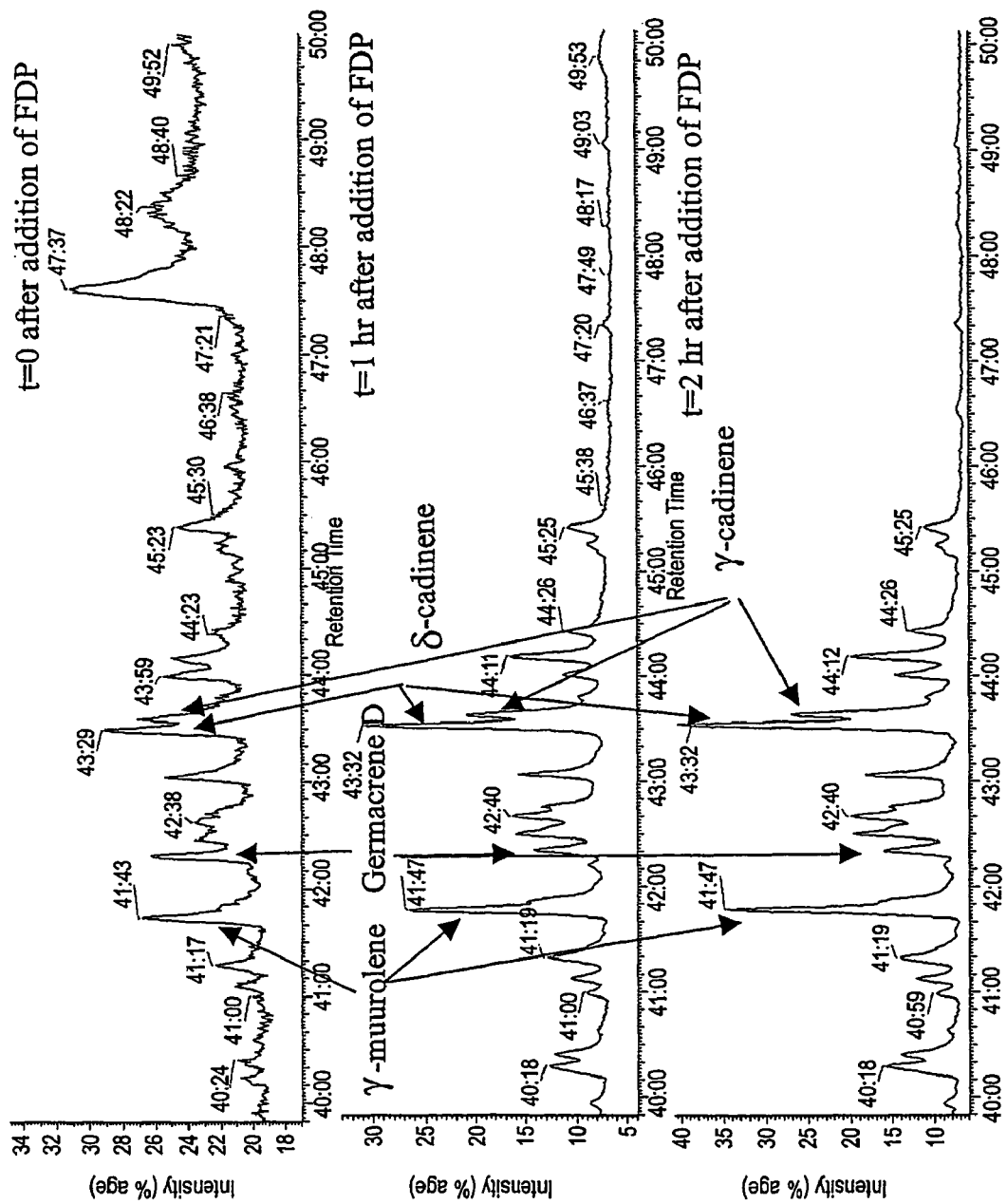
FIG. 12 shows the results of a time course experiment showing how the ratio of Germacrene D changes relative to the other Germacrene D derivative compounds over time A) at t=0 after addition of FDP, B) at t=1 hr after addition of FDP and C) at t=2 hrs after addition of FDP.
Figure 13:
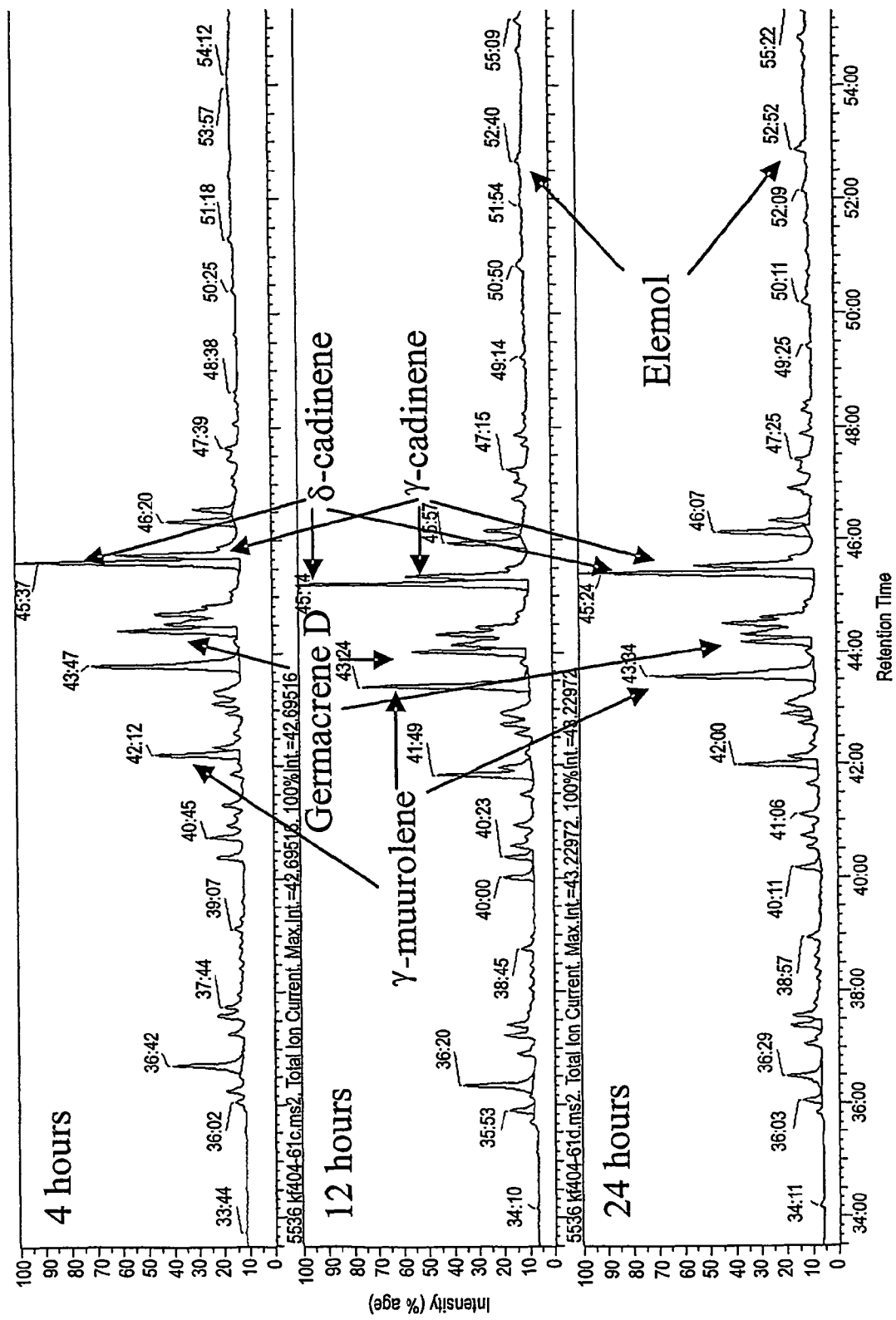
FIG. 13 shows the change in headspace volatile profile trapped on PDMS/DVB fibres over a time course of 24 hours.

Rearrangement with time of trapping: The time courses (Table 3 and FIGS. 12 and 13) show that over the period of time on PDMS/DVB fibres, the ratios of germacrene D become less compared to that of the gamma-muurolene and the 2 cadinene isomers, but gamma-muurolene and delta-cadinene maintain the same ratio relative to each other.

Gamma-muurolene is higher than delta-cadinene. This is not as predicted by Bulow and Konig (Phytochem 55: 141-168 (2000)) where delta-cadinene is 2-fold more prominent than gamma-muurolene in a silica catalysed rearrangement. In addition, elemol is not detectable with 4 hour trapping but is present after 12 hours and 24 hours. This may be due to lack of equilibrium or slow kinetics.

TABLE 3

Relative quantities (%) of sesquiterpenes trapped onto PDMS/PDV fibres with time of trapping. Each trapping sampled for 30 minutes at 0, 1 and 2 hours after addition of FDP to the purified enzyme.

| Compound | 0 | 1 | 2 |
| --- | --- | --- | --- |
| delta-elemene | 0 | 2.7 | 4.0 |
| gamma-elemene | 0 | 5.6 | 5.9 |
| gamma-muurolene | 15 | 20.2 | 20.0 |
| germacrene D | 9.4 | 5.0 | 4.4 |
| unresolved | 18.5 | 9.0 | 8.7 |
| alpha-muurolene | 0 | 6.9 | 8.3 |
| alpha-selinene | 0 | 6.0 | 4.5 |
| delta-cadinene | 12.6 | 15.8 | 16.6 |
| gamma-cadinene | 14.5 | 13.2 | 12.3 |
| selinadiene | 15.4 | 7.7 | 7.6 |
| alpha-cadinene | 0 | 3.4 | 3.9 |
| germacrene B | 14.6 | 4.5 | 3.8 |

Example 5

Optimisation of large-scale production of protein and protein kinetics: *E. coli* BL21-Plus™-RIL cells harbouring pET-30a75565 were grown overnight at 37° C. in Lauria-Bertani media supplemented with 30 µg ml$^{-1}$ kanamycin and 34 µg ml chloramphenicol$^{-1}$. 5 mL aliquots of overnight culture were used to inoculate 4×300 mL of fresh 2× YT medium supplemented with 30 µg ml$^{-1}$ kanarnycin and 34 µg ml$^{-1}$ chloramphenicol in 1 L baffled flasks. Cultures were grown at 37° C. with vigorous agitation to $A_{600}$=0.8, then removed to 4° C. to equilibrate to 16° C. before induction with 0.3 mM IPTG. Induced cultures were then incubated at 16° C. and 220 rpm for a further 72 hours. Cells were pelleted by centrifugation (2500×g; 10 min) and stored overnight at −20° C. The following day cell pellets were resuspended in 20 mL His6 binding buffer and cells were disrupted by 2 passes through an EmulsiFlex®-C15 high-pressure homogeniser (Avestin) with a pressure setting between 15000-20000 psi. Cell debris was pelleted by centrifugation 2× at 10000×g for 15 min; 4° C. (Sorval SS34 rotor). The supernatant was filtered through a 0.45 µm filter (Amicon). Filtered extract was desalted and passed over a Nickel affinity column. Concentration of the recombinant synthase in the purified protein extracts was estimated from SDS-PAGE gels by comparing against a BenchMark™ Protein Ladder (Invitrogen). Purified extracts were adjusted to a workable concentration with His6 elution buffer (without Imidazole) containing 10% glycerol and 1 mM DTT. The extract was then separated into 100 µl aliquots and stored at −80° C. until required. As a control for future analysis, BL21-Plus™-RIL cells harbouring pET-30a only were also induced and purified as above.

Protein oligomerisation: 1.5 mL of His6 purified protein extract (containing ~60 µg of the recombinant synthase purified protein) was loaded onto a 600×16 mm S200 Sephacryl column (Pharmacia) at a flow rate of 1 mL min$^{-1}$. The column was pre-equilibrated and eluted with 50 mM Bis-tris propane buffer (pH7.5) containing 10% glycerol and 150 mM KCl. Fractions corresponding to protein peak of interest were pooled and assayed after adjusting to 10 mM $MgCl_2$ and adding 20 µM $^3$H-FDP for activity. Molecular mass of active fractions was calculated based on comparison to standards of known molecular mass.

Kinetic Studies: For kinetic studies, Germacrene D synthase active protein that had been induced in culture and purified as described for protein optimisation was added to a minimal assay buffer containing 50 mM Bis-Tris-Propane (pH 7.5), 10% (v/v) glycerol, 1 mM DTT and 0.1% (v/v) Tween-20. Tritiated FDP was added variously depending on the experiment. One mL assays containing 100-150 ng of the recombinant synthase were overlaid with 0.6 mL pentane and incubated in 1.5 mL microfuge tubes for 2 hours at 30° C. and 150 rpm. All assays were performed in triplicate. Following incubation assays were immediately placed on ice and a 200 µL aliquot of the pentane layer removed for analysis. The aliquots were added to 1.5 mL microfuge tubes containing 0.7 mL Organic Counting Scintillant (OCS) (Amersham) and vortexed briefly. Scintillation analysis was performed using a Wallac 1409 Liquid Scintillation Counter ($^3$H efficiency≈70%).

Kinetic studies with $^3$H-FDP (10.06 Mbq/mL) as substrate (concentration range 1 µM to 100 µM with saturating $Mg^{2+}$ were carried out to determine Km for FDP. Kinetic constants for $Mg^{2+}$, and $Mn^{2+}$ at 10 µM $^3$H-FDP (assay range 50 µM to 10 mM and 25 µM to 5 mM of the chloride salts respectively) were determined. The effect on enzyme activity of metal co-factors with and without salts was also tested. $Mg^{2+}$ and $Mn^{2+}$ were added in the presence and absence of 50 mM KCL and 50 mM NaCl in all possible combinations. Controls included incubation without enzyme, with enzyme but without metal ion cofactors and with enzyme and cofactors in the presence of 10 mM EDTA. A further control comprising His6 purified pET-30a extract was also assayed to determine potential utilisation of FDP by co-purifying bacterial proteins.

For determination of the enzyme pH optimum, assays were carried in a tri-buffer system containing 51 mM diethanolamine, 100 mM MES, and 51 mM N-ethylmorpholine at pH values between 5.7 and 9.5 with 10 mM $MgCl_2$, 10 µM FDP, 10% (v/v) glycerol, 1 mM DTT and 0.1% (v/v) Tween-20. Optimal temperatures for enzyme activity in the range 16° C.-50° C. were also determined using the standard assay buffer and 10 mM $MgCL_2$, and 10 µM FDP. Kinetic constants were determined from the DPM data by nonlinear regression using the Origin50 graphics package. Data presented represents the means of three determinations with standard errors within ±10% and with background DPM calculated from controls subtracted.

All experiments were carried out at least twice.

Because it was apparent that the matrix of the fibres could affect the composition of the sesquiterpenes trapped, we also checked the production of individual sesquiterpenes produced by purified protein in response to different pH conditions in the enzyme assay medium.

Figure 14:
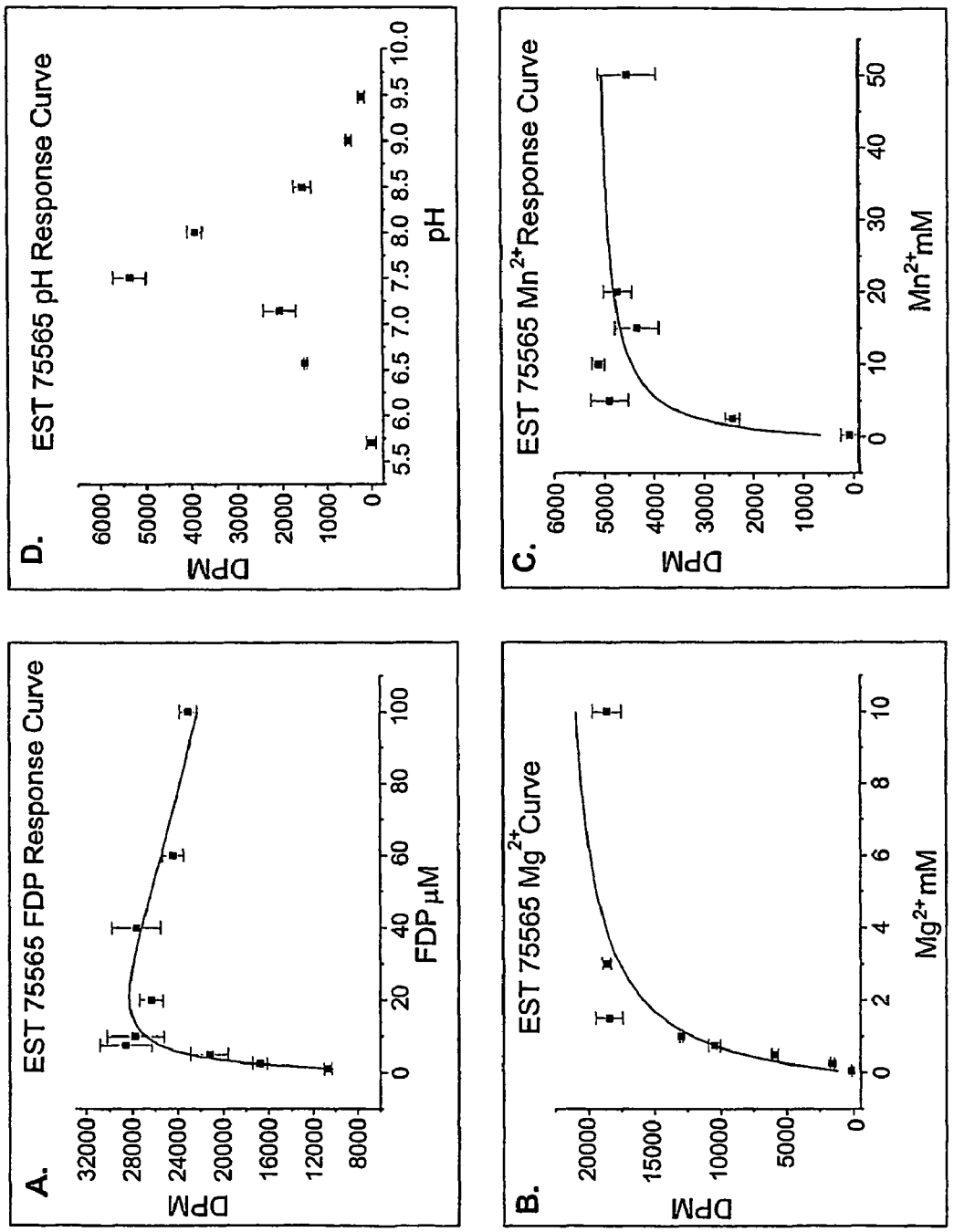
FIG. 14 shows graphs of the variation of the multifunctional germacrene-D synthase activity with (A) substrate concentration, (B) $Mg^{2+}$ concentration (C) $Mn^{2+}$ concentration and (D) pH.

Results:

Km The Km for FDP was in the 1-2 µM range with saturating concentrations at ~7.5 µM (FIG. 14A). The recombinant synthase exhibited a low Ki with ~50% inhibition at 1 mM substrate concentrations. Km for the cofactor $Mg^{2+}$ was in the 0.6 to 1.2 mM range (FIG. 14B) and the Km for $Mn^{2+}$, although difficult to determine with a high degree of accuracy given very low synthase activity in the presence of $Mn^{2+}$, was in the 50 to 300 µM range (FIG. 14C). No significant inhibition was observed in the presence of high concentrations (>5 mM and 10 mM) of the respective $Mg^{2+}$ and $Mn^{2+}$ chloride salts. Kms in the literature range from 0.4-4.5 µM for FDP, 70-150 µM for Mg, 7-30 µM for Mn for other sesquiterpene synthases (e.g. Cai et al Phytochemistry 61, 523-529 (2002), Steele et al J. Biol. Chem. 273, 2078-2089(1998)).

pH Germacrene D synthase showed a pH optimum of 7.5. pH values of 0.5 pH units lower and 1 pH unit higher than 7.5 resulted in 47% and 59% respective decreases in enzyme activity FIG. 14D. This pH is within the range (between pH 7 and 9) reported for other characterised sesquiterpene synthases in the literature (Cai et al Phytochemistry 61, 523-529 (2002); Steele et al J. Biol. Chem. 273, 2078-2089 (1998))

Figure 15:
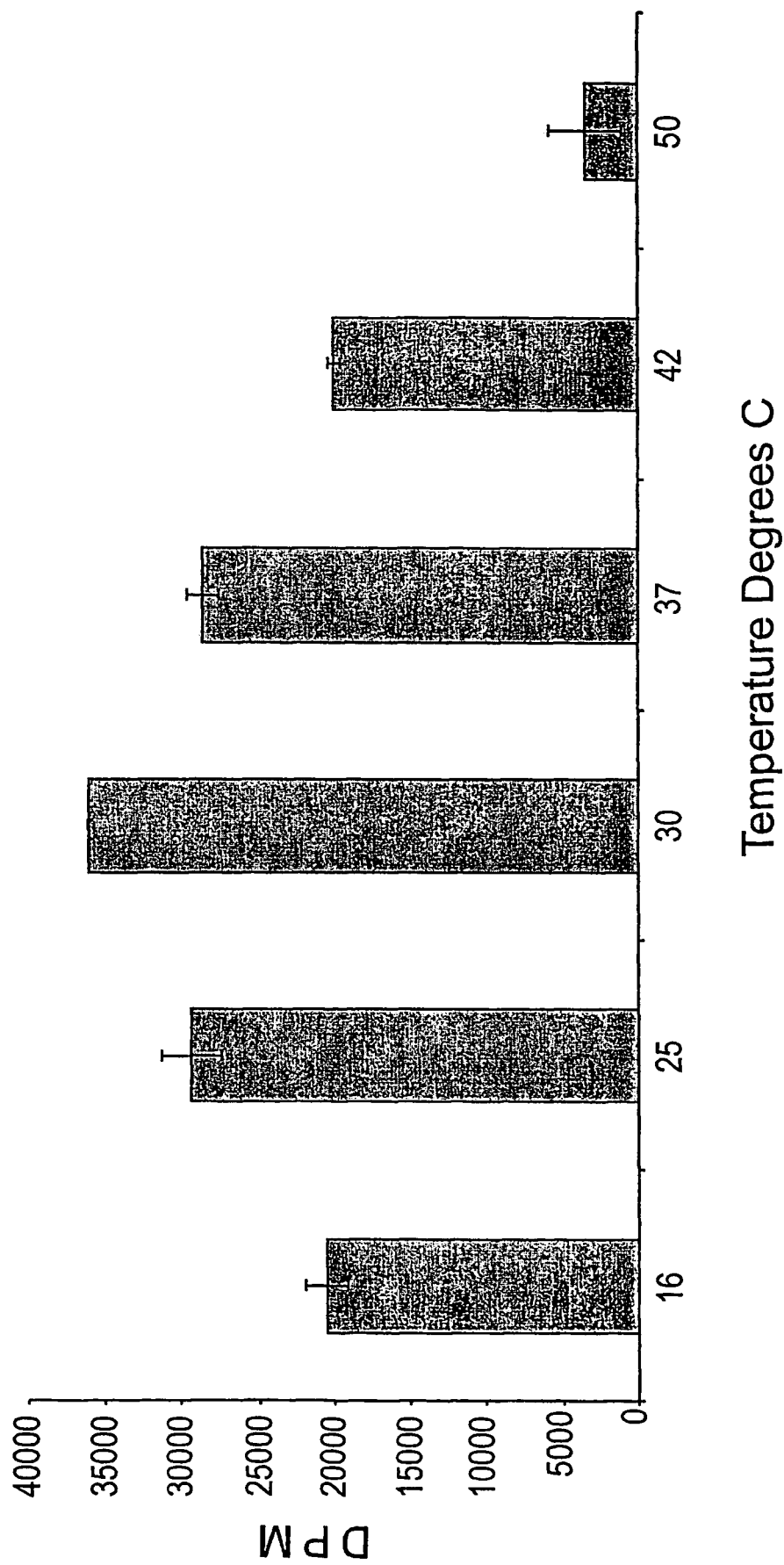
FIG. 15 shows graph of germacrene-D synthase activity against temperature.

Temperature Maximum synthase activity occurred at 30° C., with a significant reduction in activity observed above 42° C. (FIG. 15). Little or no activity was observed at 50° C. Significant activity was observed at low temperatures however with the synthase exhibiting ~56% of the optimal temperature activity at 16° C. The optimal temperature is similar to that reported for other sesquiterpene synthases.

Figure 16:
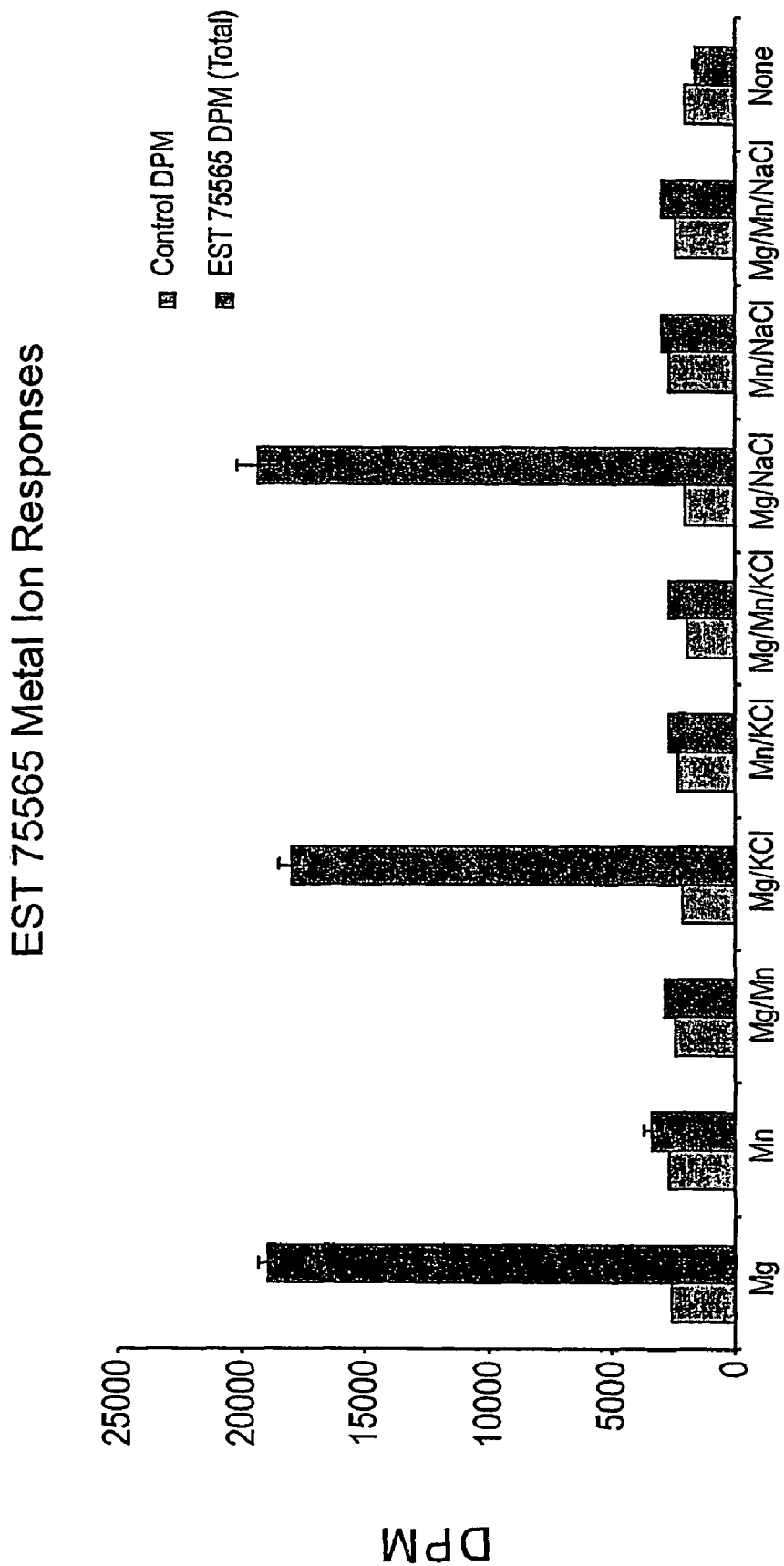
FIG. 16 shows variation of germacrene-D synthase activity with varying metal ion contents.
Figure 17:
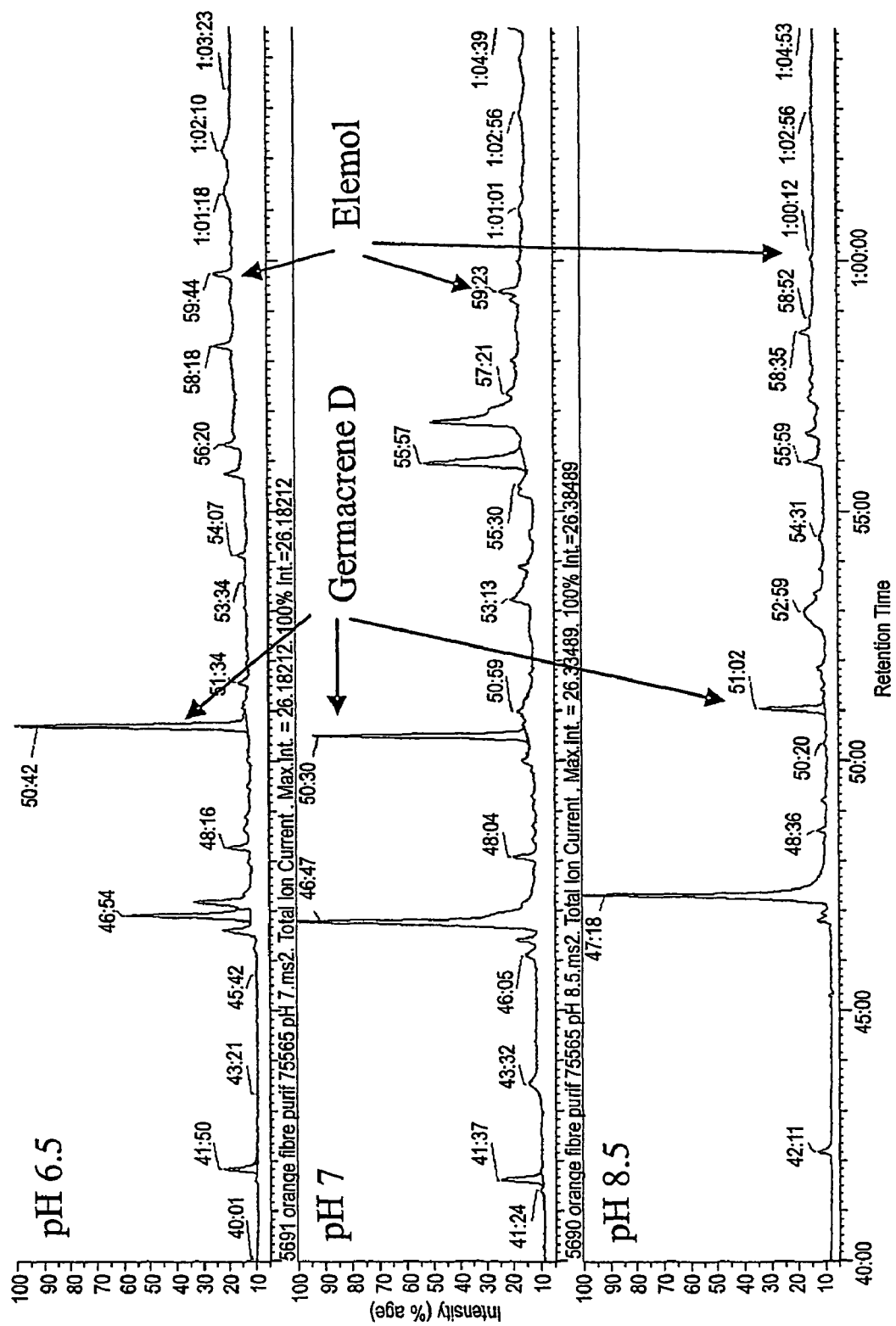
FIG. 17 shows GC-MS trace of headspace profiles at 3 different pHs trapped on Carbowax®/DVB SPME fibres after 21 hours.

Other metal ion effects. Germacrene D synthase has a requirement for $M^{2+}$ as a cofactor for activity and inhibition by $Mn^{2+}$ ions. Mn can act as a cofactor when alone, but inhibits Mg requiring cofactor activity. Addition of $K^+$ or $Na^+$ ions had little or no effect on activity, and the recombinant enzyme showed a strong preference for $Mg^{2+}$ over $Mn^{2+}$ (Vrel $Mn^{2+}$~27%). (FIG. 16). The absence of DTT was also shown to significantly decrease activity (Vrel in the absence of DTT ~53% under optimal conditions. The presence of Mn in the buffer resulted in inhibition of activity even if $Mg^{2+}$ was present.

pH effect on ratios of sesquiterpene products: Germacrene D was the major product when the volatiles produced by the purified enzyme were trapped at 3 different pHs onto Carbowax®/DVB fibres. Germacrene D was the major product at all 3 pH levels (FIG. 17) and was present in similar percentages (Table 4).

The headspace profiles show that there is clearly less product at pH 8.5 and these results agree with the kinetic studies which suggest that the optimum pH is at pH7.5. However the other products, delta-elemene, beta-elemene, gamma-elemene, Germacrene B, delta-cadinene and elemol, varied in relative contribution with pH. The ratios of these products are given in Table 4

TABLE 4

Ratios of products at 3 different pHs trapped on Carbowax ®/DVB SPME fibres after 21 hours

| Compound | % at pH 6.5 | % at pH 7.5 | % at pH 8.5 |
| --- | --- | --- | --- |
| delta-elemene | 10.4 | 13.4 | 14.6 |
| beta-elemene | 10.6 | 6.3 | 1.7 |
| gamma-elemene | 5.9 | 6.8 | 9.0 |
| germacrene D | 64.6 | 64.8 | 64.9 |
| germacrene B | 2.7 | 2.3 | 4.8 |
| delta-cadinene | nd | 1.2 | nd |
| elemol | 5.9 | 5.2 | 4.9 |

Example 6

Copy Number and Expression in *Actinidia*:

DNA was extracted from leaves of four *Actinidia* species (*Actinidia deliciosa* 'Hayward', *Actinidia chinensis* 'Hort16A', *Actinidia arguta* 'Hortgem Tahi' and *Actinidia* CK51_05) by a modification of the plant DNA extraction method of Murray and Thompson Nucleic Acids Res. 8: 4321-5 (1980). The leaf material (up to 1 g) was ground in liquid nitrogen and the powder was added to 20 ml buffer (2% cetyltrimethylammonium bromide, 100 mM Tris pH 8.0, 20 mM EDTA, 1.4 M NaCl) that had been heated to 55° C. The extract was placed in a 55° C. waterbath, 400 µl β-mercaptoethanol was added and the extract was gently swirled until the temperature of the waterbath reached 50° C. The extract was then left at room temperature for 15 minutes, after which 20 ml chloroform:isoamyl alcohol (24:1) was added and the extract gently swirled until well-mixed. The extract was then centrifuged at 8000 rpm for 20 minutes at 20° C. The top layer was removed and an equal volume of isopropanol was added. After inverting gently until mixed the DNA was spooled out. RNAse (Roche) (1 µl of 10 mg/ml) was added to remove RNA.

Southern analysis: Genomic DNA that had been extracted from leaves of four *Actinidia* species was put through the Wizard DNA Clean-Up system (Promega) and then digested overnight with EcoR1 in a total volume of 50 µl. The digested DNA was then electrophoresed through 0.5% agarose, visualised with ethidium bromide, hydrolysed in 0.25M HCl and washed in water before transfer to Nytran-Plus (Schleicher & Schuell) membrane in 0.4M NaOH overnight. The membrane was then neutralised in 0.5M Tris and prehybridised in Washing and Pre-Hyb Solution (MRC) for two hours. Hybridisation was performed in 10 ml of High Efficiency Hybridzation System (MRC) using as a probe a $^{32}$P-labelled 350 base pair PCR fragment that was complementary to a region near the 5' end of the coding sequence of germacrene D synthase. The probe (40 ng) was labelled with $^{32}$P dCTP using the rediprime™II (Amersham Pharmacia) random labelling system, following the manufacturer's directions. The labelled probe was denatured in 0.1 M NaOH for 30 minutes before hybridisation overnight. The membrane was washed in Washing and Pre-Hyb Solution (MRC) according to the manufacturer's recommendations. Hybridisation signals were visualised by scanning on a Storm 840 phospho-imaging system (Molecular Dynamics) and analysed using ImageQuant software.

RT-PCR amplification of multifunctional germacrene D synthase in plants: RT-PCR (Platinum® Quantitative RT-PCR Thermoscript One-Step System, Invitrogen) amplifications were performed according to the manufacturer's recommendations on total RNA extracted from different tissues of *Actinidia deliciosa* and from *Actinidia chinensis* fruit and from the leaves of transgenic *Arabidopsis thaliana* transformed with EST 75565. cDNA synthesis was at 60° C. for 30 minutes, followed by denaturation at 96° C. for 5 minutes, then 40 cycles of amplification involving denaturation at 96° C. for 30 seconds, annealing at 55° C. for 40 seconds and extension at 72° C. for 60 seconds. For the final cycle extension at 72° C. was continued for a further 5 minutes. Prior to RT-PCR the total RNA was treated with DNase I (Life Technologies) for 10 minutes at room temperature. Concurrently with RT-PCR amplification, PCR amplification was also performed on the DNase I-treated total RNA to check for genomic DNA contamination. The PCR primers were as follows: 75565GSP1 CAATTGAGAGGTGGGAGATC (SEQ ID NO: 13) and 75565GSP2 GTTGGAACATATCCTTGGTG (SEQ ID NO: 14) (Primer set 1); 75565NF1 TAGGCGTGTCTTACCATITT (SEQ ID NO: 15) and 75565NR1 GCATGAATGATrrGTTCCTT (SEQ ID NO: 16) (Primer set 2). PCR primer 75565GSP1, which is specific for EST 75565, was designed to amplify over an intron splice site to prohibit genomic DNA amplification. The resulting amplification products (5 µl) were analysed by electrophoresis through 1% agarose (AppliChem), followed by staining with ethidium bromide and visualisation on an ultraviolet transilluminator (UVP) attached to a camera (UV tec, Total Lab Systems Ltd).

Results:

Southern analysis revealed that the multifunctional germacrene D synthase was present at low copy number in all four genotypes tested. A homologous gene was clearly also present in *A. arguta* although EST sequencing had not revealed its presence.

Figure 18:
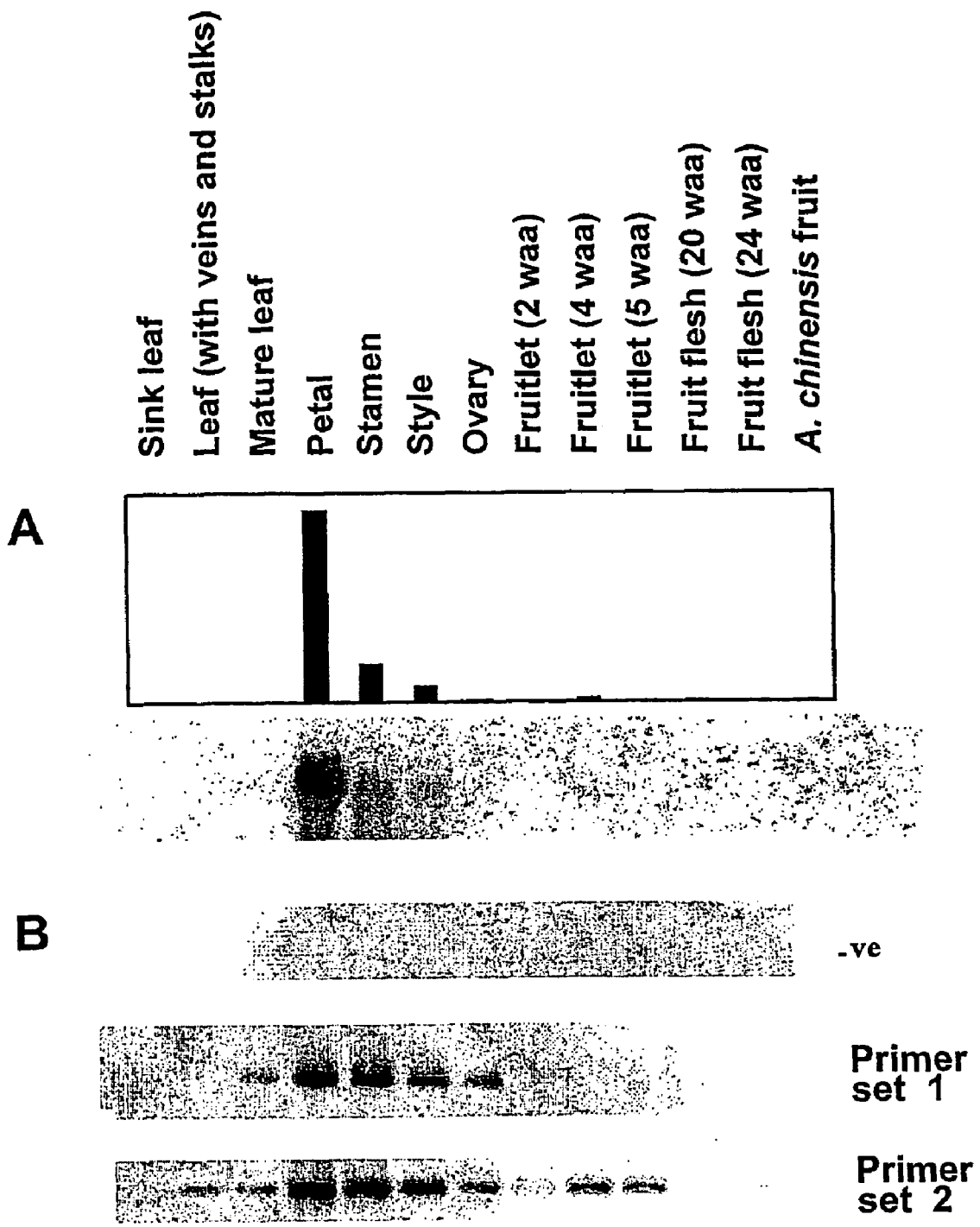
FIG. 18 shows Northern and RT-PCR analysis of total RNA extracted from different tissues of *Actinidia deliciosa* and from *Actinidia chinensis* fruit. (A) Northern analysis using as a probe an approximately 350 base pair [a-$^{32}$P] dCTP-labelled PCR fragment that was amplified from EST 75565 with the primers 75565NF1 (5' TAGGCGTGTCTTACCATT=T 3') (SEQ ID NO: 15) and 75565NR1 (5' GCATGAATGATITGTTCCTT 3') (SEQ ID NO: 16). (B) RT-PCR analysis using two sets of PCR primers that amplify an approximately 210 base pair fragment about 1000 base pairs in from the start ATG (Primer set 1) and an approximately 350 base pair fragment about 450 base pairs in from the start ATG (Primer set 2). -ve=PCR amplification using Primer set 1.

The multifunctional germacrene D synthase was highly expressed in *A. deliciosa* 'Hayward' petals (FIG. 18). Lower concentrations of transcript were detected by northern analysis in stamens and styles. The more sensitive PCR technique indicated low levels of transcript in ovaries and mature leaves of 'Hayward' with one set of primers. A second set of primers however detected transcripts in expanded leaves and young fruitlets (to 5 weeks after anthesis) in 'Hayward'. No transcripts were detected in mature fruit of either 'Hayward' or *A. chinensis* 'Hort16A'. However a virtual northern analysis based on discovery of related transcripts in libraries in the EST database indicated expression of transcripts in 'Hayward' petals, *A. chinensis* 'Hort16A' vegetative meristems and young fruit of Vaccinium corymbosum (blueberry).

Example 7

Expression of Multifunctional Germacrene D Synthase in *Arabidopsis*

Preparation of competent *Agrobacterium tumefaciens* GV3101: *A. tumefaciens*, strain GV3101, containing binary vectors for plant transformation, was inoculated into 10 mL of LB or 2YT media containing rifampicin (10 mg/mL); gentamycin (25 mg/mL); and spectinomycin (100 mg/mL) for 24 hours at 28° C., with shaking at 200 rpm. These cultures were then used to inoculate a further 100-200 mL of LB or 2YT media, with antibiotics as above, which were again grown for 24 hours at 28° C., with shaking. The cells were collected by centrifugation (3,500×g, 10 min, 4° C.) and resuspended, to a final $OD_{600}$ of 0.8, in 5% sucrose solution. Silwet L-77 was added to a concentration of 0.05%.

Transformation of *Agrobacterium tumefaciens* GV3101: 45 mL aliquots of competent *Agrobacterium* cells were thawed gently on ice. 50-200 ng of plasmid DNA was added to each aliquot and gently mixed, then 40 mL of the cell/plasmid mixture was pipetted into a pre-chilled electroporation cuvette (0.2 cm gap, Bio-Rad). The cells were electroporated using a BioRad GenePulser, on the following settings:
Voltage: 2.5 kV
Capacitance: 25 mFd
Resistance: 400 Ohms The time constant for the pulse was typically 7-9 ms.

The cells were immediately recovered by addition of 1 mL LB media, then decanted into sterile 15 mL centrifuge tubes and incubated at room temperature, with shaking (60 rpm). After 2 hours, 10 mL and 100 mL of the transformed bacteria was spread onto separate LB plates containing rifampicin (10 mg/mL); gentamycin (25 mg/mL); and spectinomycin (100 mg/mL); then grown for 48 hours at 28-30° C.

Transformation of *Arabidopsis thaliana* by floral dip: *Agrobacterium tumefaciens*, containing the appropriate plasmids, were grown in 5 mL cultures of LB media containing rifampicin (10 mg/mL); gentamycin (25 mg/mL); and spectinomycin (100 mg/mL) for 24 hours at 28° C. The cells were collected by centrifugation and resuspended, to a final $OD_{600}$ of 0.8, in 5% sucrose solution. Silwet L-77 was added to a concentration of 0.05%.

Healthy *Arabidopsis* plants, around five weeks old, showing a number of immature flower clusters, were used for the dipping procedure. The whole of the aboveground portion of the plant was dipped into the *Agrobacterium suspension*, and gently agitated for 3-5 seconds. The dipped plants were then placed in humidity chambers in reduced light for 2-3 days, before being allowed to flower and set seed as normal. The seed was harvested upon complete drying of the plants (5-6 weeks after dipping).

Growth of seed from transformed *Arabidopsis*: Approximately 1000 T1 seeds were measured into a microcentrifuge tube. The seed was sterilised by a 1.5% bleach solution containing 0.01% Triton-X, mixed, and incubated for 15 min with occasional mixing. The seed was washed several times with distilled water, and resuspended in 0.1% agarose, prior to plating on 0.5× MS media, containing 100 mg/nL kanamycin. The plates were placed into growth rooms with a 12-hour light/12-hour dark cycle. After 2-3 weeks growth the plants were transferred onto fresh plates to confirm kanamycin resistance and were allowed to continue growing in glasshouse conditions until required for headspace analysis.

Headspace Analysis of *Arabidopsis*

*Arabidopsis* plants were grown in soil in a glass house. When mature (8 weeks old) and with inflorescences, three plants were transferred to a 3 L glass vessel with ground glass joint flanges. The vessel was sealed with an appropriate ground glass flanged lid which was fitted with a headspace adaptor with an air inlet and outlet. Volatiles were collected onto 100 mg Chromosorb 105 adsorbent traps, which were fitted to the air outlet port of each adaptor. The volatiles were purged from the vessel onto the traps with clean air at 50 mL min$^{-1}$ for 6 days. The traps were analysed by GC-MS analysis immediately after extraction of volatiles in the same manner as for the dynamic headspace of kiwifruit flowers.

Results

Figure 19:
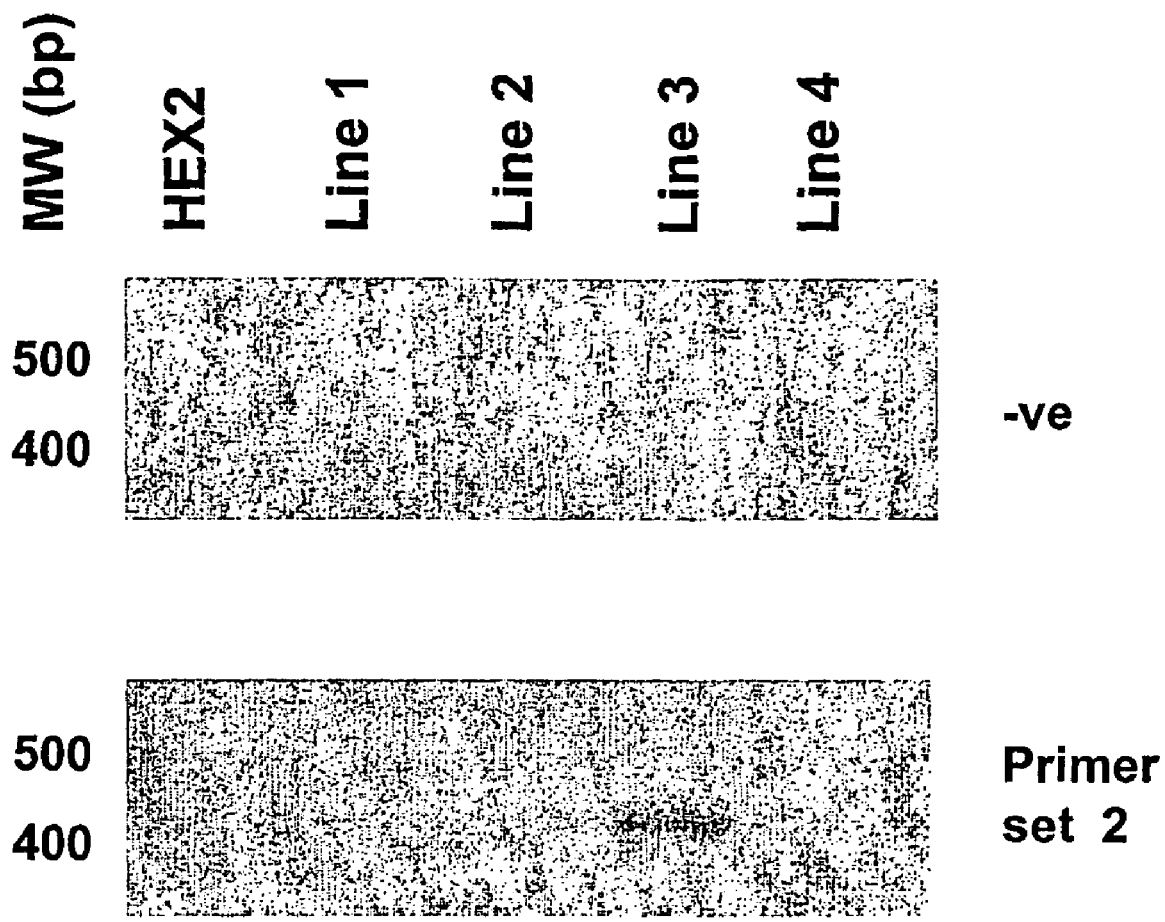
FIG. 19 shows RT-PCR amplification of total RNA extracted from seedlings of transgenic *Arabidopsis thaliana* lines using primers (Primer set 2) designed towards the 5' end of the germacrene D synthase cDNA sequence. The size of the amplification product expected is approximately 350 bp. The lane labelled MW is the molecular weight marker (Invitrogen). Lanes labelled Line 1 to 4 contain the resulting products from PCR amplification of the total RNA and Lanes labelled 2 contain the resulting products from RT-PCR amplification of the total RNA. bp=base pairs.
Figure 20:
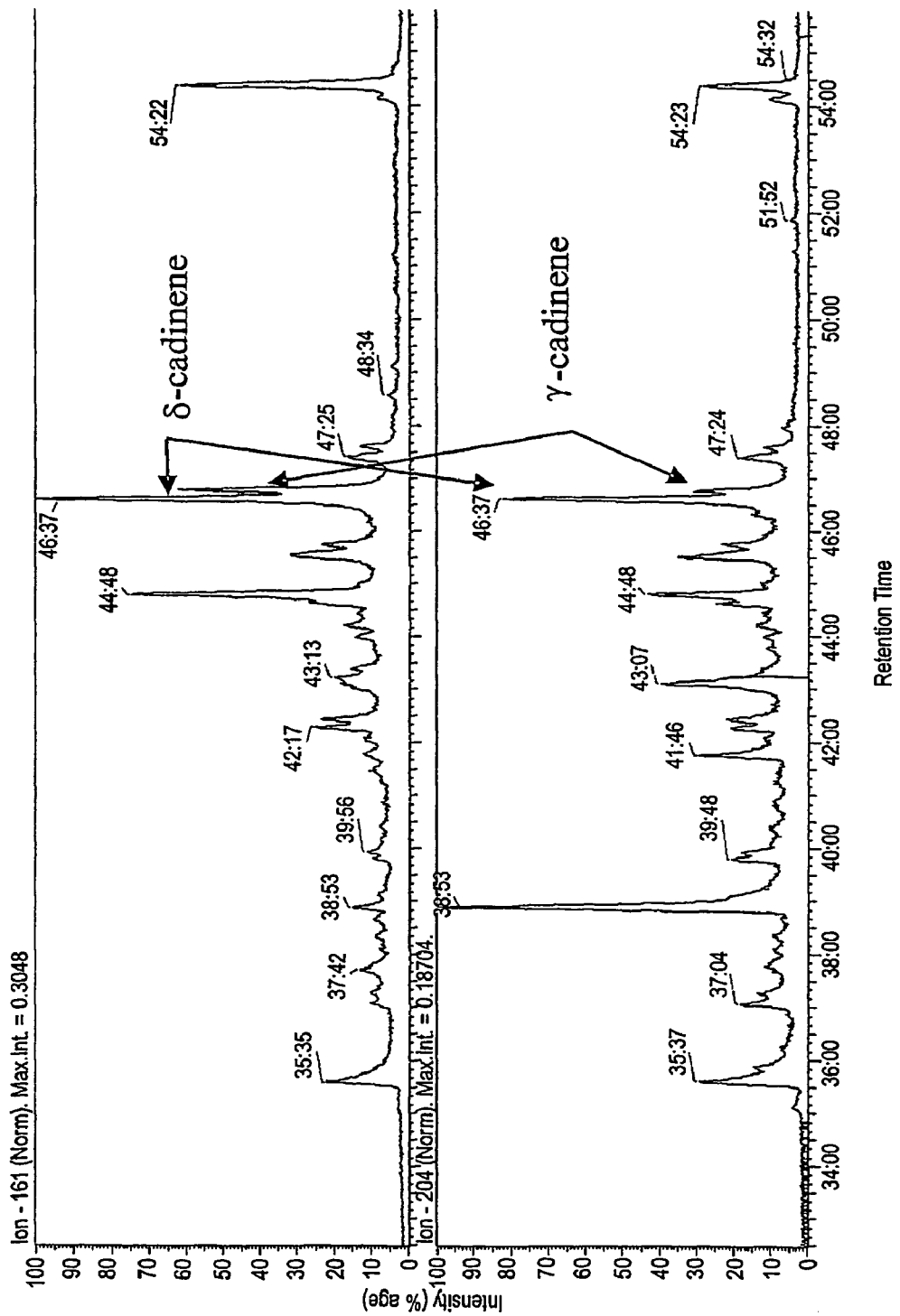
FIG. 20 Profiles of ions (A) 161 and (B) 204 (indicative of sesquiterpenes) from the GCMS trace of headspace collected above *Arabidopsis* plants transformed with multifunctional germacrene D synthase gene growing in a 3L growth vessel for 6 days.

Germacrene D synthase transcripts were detected in transgenic *Arabidopsis* (see FIG. 19). There were a number of compounds detected in the headspace of the transformed *Arabidopsis* grown in the growth vessel. In order to clarify if any of these compounds were germacrene D (or other sesquiterpenes) the ions of the base peak (161) and the molecular ion (204) were isolated from the TIC (see FIG. 20). This work showed that a number of sesquiterpenes were produced in the *Arabidopsis* including delta-elemene, alloaromadendrene, beta-caryophyllene, thujopsene, an unidentified sesquiterpene which may be Germacrene D or gamma-muurolene, delta-cadinene, gamma-cadinene, possibly alpha-muurolene and elemol. Recently, literature has been published which cites caryophyllene, thujopsene, beta-chamigrene, humulene, farnesene, bisabolene, and nerolidol as being present in flowering *Arabidospis* plants (Aharoni et al., The Plant Cell, Vol. 15, 2866-2884 (2003)). Neither this work or the published literature suggests that delta-elemene, Germacrene D, gamma-muurolene, delta-cadinene, gamma-cadinene, alpha-muurolene or elemol can be found in wild type flowering *Arabidopsis*. The presence of delta-elemene, Germacrene D, gamma-muurolene delta-cadinene, gamma-cadinene, alpha-muurolene or elemol in the transformed *Arabidopsis* is consistent with the results shown by the purified recombinant protein.

The above Examples are an illustration of practice of the invention. It will be appreciated by those skilled in the art that the invention can be carried out with numerous modifications and variations. For example, variations to the nucleotide sequences may be used and the sequences may be expressed in different organisms.

SEQUENCE LISTING

<160> NUMBER OF SEQ ID NOS: 16

<210> SEQ ID NO 1
<211> LENGTH: 2019
<212> TYPE: DNA
<213> ORGANISM: Actinidia deliciosa

<400> SEQUENCE: 1

```
gtgaaaacta aaataggcca agtgtgtagg ttcatctcta gtttttctct ttaaattaat      60
tcttcaaccc agaaaaaaaa catgcaacta ccttgtgctc aagctttgcc aataccaact     120
gttacaacca ccactagtat tgaaccacca catgtaacgc gtcgctctgc aaattatcat     180
cctagcattt ggggagatca tttcctcgcc tactcttccg atgctatgga agaagaggtt     240
attaacatgg aacaacaaca acgacttcat cacctgaaac aaaaggtgag aaaaatgcta     300
gaggcagctg ctgaacaatc ttcacagatg ctgaacctcg tcgacaaaat ccaacgctta     360
ggcgtgtctt accattttga aactgagatc gaaacagctt tacggcacat atacaaaacc     420
tgtgattacc attttgatga tctccacact gctgctctct cttttcggtt acttagacaa     480
caaggatatc cagtttcttg tgatatgttc gacaaattca agaacagcaa aggtgagttt     540
caagaatcca taatcagcga tgtgcaagga atgttaagtt tgtatgaagc tacatgtcta     600
aggatacacg gagaagatat actagacgaa gcactagctt ttaccatcac tcaacttcgg     660
tccgcattgc ccaacttaag cactcctttc aaggaacaaa tcattcatgc tctgaaccag     720
cccatccaca aggggttgac aaggctcaac gcaaggagcc acatttttatt ttttgaacag     780 aatgattgcc atagcaaaga cctttttgaat ttcgcaaaat tagatttcaa cttattacaa     840
aagttgcacc agagggagct atgtgaaatc acaaggtggt ggaaagattt gaattttgca     900
aagacactac cttttgccag agacagaatg gtagagtgct acttttggat acttggggtg     960
tactttgagc cccaatatct gcttgctagg aggatgctaa ccaaggtgat tgccatgatt    1020
tccattatcg atgacatcta cgatgtctac ggtaccttgg aagaacttgt tctcttcact    1080
gatgcaattg agaggtggga gatcagtgcc ttggatcaac ttccagagta tatgaaacta    1140
```

-continued

```
tgttatcaag cacttttgga tgtttatagt atgattgatg aagagatggc gaagcaagga    1200
agatcttatt gcgtagacta tgcaaaatct tcaatgaaaa ttttggttag agcatacttc    1260
gaagaagcca aatggtttca ccaaggatat gttccaacta tggaagagta tatgcaagtt    1320
gcattagtaa ccgcgggtta caaaatgctt gcaacctctt cctttgttgg catgggagat    1380
ttggcaacca aagaggcctt tgattgggtg tcaaatgatc ctttaattgt tcaagctgca    1440
tcagtgatag gcagactcaa ggatgacatt gttggccaca gtttgagca aaagagaggg     1500
cacgtggcgt cggctgtcga atgctacagt aagcaacatg gtacaacaga ggaagaggct    1560
attattgaat tggataaaca agttacacat tcatggaaag acatcaacgc agagtgcctc    1620
tgcccaatca aggtcccaat gcctcttctt gcgcgagttc tcaatcttgc acgagtgctt    1680
tatgttatat accaggatga agacggatac actcatcctg aaccaaggt cgagaacttt     1740
gtaacctcag tgcttatcga ttctatgcca atcaattaga aaatgtaaca agacactgaa    1800
gtggaggcat aaataaattc aaaagttgat ttaaagttgg ggtagtgaac ggggattctt    1860
accattaaga gatattcttg ctaaaaagca attaattcaa tgcatttcca ataaaataat    1920
ttagccagtt gttcttcatc ttgttttttt tttgtttctc tttcctttct aaatataaaa    1980
ttataattaa ttggcaaaaa aaaaaaaaaa aaaaaaaa                             2019
```

<210> SEQ ID NO 2
<211> LENGTH: 565
<212> TYPE: PRT
<213> ORGANISM: Actinidia deliciosa

<400> SEQUENCE: 2

```
Met Gln Leu Pro Cys Ala Gln Ala Leu Pro Ile Pro Thr Val Thr Thr
1               5                   10                  15

Thr Thr Ser Ile Glu Pro Pro His Val Thr Arg Arg Ser Ala Asn Tyr
            20                  25                  30

His Pro Ser Ile Trp Gly Asp His Phe Leu Ala Tyr Ser Ser Asp Ala
        35                  40                  45

Met Glu Glu Val Ile Asn Met Glu Gln Gln Gln Arg Leu His His
    50                  55                  60

Leu Lys Gln Lys Val Arg Lys Met Leu Glu Ala Ala Glu Gln Ser
65                  70                  75                  80

Ser Gln Met Leu Asn Leu Val Asp Lys Ile Gln Arg Leu Gly Val Ser
                85                  90                  95

Tyr His Phe Glu Thr Glu Ile Glu Thr Ala Leu Arg His Ile Tyr Lys
            100                 105                 110

Thr Cys Asp Tyr His Phe Asp Asp Leu His Thr Ala Ala Leu Ser Phe
        115                 120                 125

Arg Leu Leu Arg Gln Gln Gly Tyr Pro Val Ser Cys Asp Met Phe Asp
    130                 135                 140

Lys Phe Lys Asn Ser Lys Gly Glu Phe Gln Glu Ser Ile Ile Ser Asp
145                 150                 155                 160

Val Gln Gly Met Leu Ser Leu Tyr Glu Ala Thr Cys Leu Arg Ile His
                165                 170                 175

Gly Glu Asp Ile Leu Asp Glu Ala Leu Ala Phe Thr Ile Thr Gln Leu
            180                 185                 190

Arg Ser Ala Leu Pro Asn Leu Ser Thr Pro Phe Lys Glu Gln Ile Ile
        195                 200                 205

His Ala Leu Asn Gln Pro Ile His Lys Gly Leu Thr Arg Leu Asn Ala
```

-continued

```
                    210                 215                 220
Arg Ser His Ile Leu Phe Phe Glu Gln Asn Asp Cys His Ser Lys Asp
225                 230                 235                 240

Leu Leu Asn Phe Ala Lys Leu Asp Phe Asn Leu Leu Gln Lys Leu His
                245                 250                 255

Gln Arg Glu Leu Cys Glu Ile Thr Arg Trp Trp Lys Asp Leu Asn Phe
            260                 265                 270

Ala Lys Thr Leu Pro Phe Ala Arg Asp Arg Met Val Glu Cys Tyr Phe
        275                 280                 285

Trp Ile Leu Gly Val Tyr Phe Glu Pro Gln Tyr Leu Leu Ala Arg Arg
290                 295                 300

Met Leu Thr Lys Val Ile Ala Met Ile Ser Ile Asp Asp Ile Tyr
305                 310                 315                 320

Asp Val Tyr Gly Thr Leu Glu Glu Leu Val Leu Phe Thr Asp Ala Ile
                325                 330                 335

Glu Arg Trp Glu Ile Ser Ala Leu Asp Gln Leu Pro Glu Tyr Met Lys
            340                 345                 350

Leu Cys Tyr Gln Ala Leu Leu Asp Val Tyr Ser Met Ile Asp Glu Glu
        355                 360                 365

Met Ala Lys Gln Gly Arg Ser Tyr Cys Val Asp Tyr Ala Lys Ser Ser
370                 375                 380

Met Lys Ile Leu Val Arg Ala Tyr Phe Glu Glu Ala Lys Trp Phe His
385                 390                 395                 400

Gln Gly Tyr Val Pro Thr Met Glu Glu Tyr Met Gln Val Ala Leu Val
                405                 410                 415

Thr Ala Gly Tyr Lys Met Leu Ala Thr Ser Ser Phe Val Gly Met Gly
            420                 425                 430

Asp Leu Ala Thr Lys Glu Ala Phe Asp Trp Val Ser Asn Asp Pro Leu
        435                 440                 445

Ile Val Gln Ala Ala Ser Val Ile Gly Arg Leu Lys Asp Asp Ile Val
        450                 455                 460

Gly His Lys Phe Glu Gln Lys Arg Gly His Val Ala Ser Ala Val Glu
465                 470                 475                 480

Cys Tyr Ser Lys Gln His Gly Thr Thr Glu Glu Ala Ile Ile Glu
                485                 490                 495

Leu Asp Lys Gln Val Thr His Ser Trp Lys Asp Ile Asn Ala Glu Cys
            500                 505                 510

Leu Cys Pro Ile Lys Val Pro Met Pro Leu Leu Ala Arg Val Leu Asn
        515                 520                 525

Leu Ala Arg Val Leu Tyr Val Ile Tyr Gln Asp Glu Asp Gly Tyr Thr
        530                 535                 540

His Pro Gly Thr Lys Val Glu Asn Phe Val Thr Ser Val Leu Ile Asp
545                 550                 555                 560

Ser Met Pro Ile Asn
                565
```

<210> SEQ ID NO 3
<211> LENGTH: 1815
<212> TYPE: DNA
<213> ORGANISM: Actinidia deliciosa

<400> SEQUENCE: 3

```
ctaaaatagg ccaagtgtgt aggttcatct ctagttttc tcttgaaaac taaaataggc    60
caagtgtgta ggttcatctc tagttttct cttgaaaact aaaataggcc aagtgtgtag   120
```

-continued

```
gttcatctct agttttctc tttaaattaa tccttcaacc cagaaaaaaa acatgcaact      180
accttgtgct caagctttgc caataccaac tgttacaacc aacactagta ttgaaccacc      240
acatgtaact cgtcgatctg caaattatca tcctagcatt tggggagatc atttcctcgc      300
ctactcttcc gatgctatgg aagaagagga tattaacatg gaacaacaac aacgacttca      360
tcacctgaaa caaaaggtga gaaaaatgct agaggcagct gctgaacaat cttcacagat      420
gctgaacctc gtcgacaaaa tccaacgctt aggcgtgtct taccattttg aaactgagat      480
cgaaacagct ttacggcaca tatacaaaac ctgtgattac cattttgatg atctccacac      540
tgctgctctc tcttttcggt tacttagaca acaaggatat ccagtttctt gtgatatgtt      600
cgacaaattc aagaacagca aggtgaatt caagaatcc ataatcagcg atgtgcgagg      660
aatgttaagt ttgtatgaag ctacatgtct aatgatacac ggagaagata tactagacga      720
agcactagct tttaccatca ctcaacttcg gtccgcattg cccaacttaa gcactccttt      780
caaggaacaa atcattcatg ctctgaacca gcccatccac aaggggttga caaggctcaa      840
tgcaaggagc cacatttat tttttgaaca gaatgattgc catagcaaag acctttgaa      900 tttcgcaaaa ttagatttca acttattaca aaagttgcac cagagggagc tatgtgaaat      960
cacaaggtga gatcagtgcc ttggatcaac ttccagagta tatgaaacta tgttatcaag     1020
cacttttgga tgtttatagt atgattgatg aagagatggc gaagcaagga agatcttatt     1080
gcgtagacta tgcaaaatct tcaatgaaaa ttttggttag agcatacttc gaagaagcca     1140
aatggtttca ccaaggatat gttccaacta tggaagagta tatgcaagtt gcattagtaa     1200 ccgcggggtta caaaatgctt gcaacctctt cctttgttgg catgggagag ttggcaacca     1260
aagaggcctt tgattgggtg tcaaatgatc ctttaattgt tcaagctgca tcagtgatag     1320
gcagactcaa ggatgacatt gttggccaca gtttgagca aagagaggg cacgtggcgt     1380 cggctgttga atgctacagt aagcaacatg gtacaacaga ggaagaggct attattgaat     1440
tgtataaaca agttacacat tcatggaaag acatgaacgc agagtgcctc tgcccaacca     1500
aggtcccaat gcctcttctt gcgcgagttc tcaatcttgc acgagtgctt tatgttatat     1560
accaggatgc agatggctac actcattctg gaaccaaggt caagaacttt gtaacctcag     1620
tgcttatcga ttctatgcca atcaattaga aaatttaaca agacactgaa gtggaggtat     1680
aaataaattc aaaagttgat ttaaagttgg gctagtgaac ggggattctt accattaaga     1740
gatattcttg ctaaaaagca attaattcaa tgcatttcca ataaaataat ttagccagct     1800
gttgttcaaa aaaaa                                                      1815
```

```
<210> SEQ ID NO 4
<211> LENGTH: 1897
<212> TYPE: DNA
<213> ORGANISM: Actinidia deliciosa

<400> SEQUENCE: 4
```

```
ctaaaatagg ccaagtgtgt aggttcatct ctagtttttc tcttgaaaac taaaataggc       60
caagtgtgta ggttcatctc tagttttct ctttaaatta atccttcaac ccagaaaaaa      120
aacatgcaac taccttgtgc tcaagctttg ccaataccaa ctgttacaac caacactagt      180
attgaaccac cacatgtaac tcgtcgatct gcaaattatc atcctagcat tggggagat      240 catttcctcg cctactcttc cgatgctatg gaagaagagg atattaacat ggaacaacaa      300
caacgacttc atcacctgaa acaaaaggtg agaaaaatgc tagaggcagc tgctaaacaa      360
```

-continued

```
tcttcacaga tgctgaacct cgtcgacaaa atccaacgct taggcgtgtc ttaccatttt       420
gaaactgaga tcgaaacagc tttacggcac atatacaaaa cctgtgatta ccattttgat       480
gatctccaca ctgctgctct ctcttttcgg ttacttagac aacaaggata tccagtttct       540
tgtgacatgt tcggcaaatt caagaactgc aaaggtgagt ttcaagaatc cataatcagc       600
gatgtgcgag gaatgttaag cttgtatgaa gctacatgtc taaggatacg cggagaagat       660
atactagacg aagcactagc ttttaccacg actcagcttc agtctgcatt gcccaactta       720
agcactccta tcaaggaaca aatcattcat gctctgaacc agcccatcca caagtggttg       780
acaaggctcg acgcaaggcg ccacatttta ttcttcgaac agaatgattg ccatggcaaa       840
gaccttttga atttcgcaaa attagatttc aactcgttac aaaagttgca ccagagggag       900
ctatgtgaaa tcacaaggtg gtggaaagat ctggattttg ccaagaaact accttttgcc       960
agagacagaa tggtagagtg ctacttctgg atacttgggg tgtactttga gccccaatat      1020
ttgcgtgcta ggaggatgct aaccaaggtg attgccttga cttccattat cgatgacatc      1080
tacgatgtct acggtacctt ggaagaactt gttctcttca ctgatgcaat gagaggtgg       1140
gaaattagtg ccttggataa ccttccagat tatatgaaac tatgttatca agcacttttg      1200
gatgtttata gtatgattga tgaagagatg gccaagcaag aagatcttta ttgcgtagac      1260
tatgcaaaat cttcaatgaa aatttttggtt agagcatact tcgaagaagc caaatggttt      1320
caccaaggat atgttccaac tatggaagag tatatgcaag ttgcattagt aaccgcgggt      1380
tacaaaatgc ttgcaacctc ttcctttgtt ggcatgggag agttggcaac caagagggcc      1440
tttgattggg tgtcaaatga tccttaaatt gttcaagctg catcagtgat aggcagactc      1500
aaggatgaca ttgttggcca caagtttgag caaaagagag ggcacgtggc gtcggctgtc      1560
gaatgctaca gtaagcaaca tggtacaata gaggaagagg ctattattga attggataaa      1620
caagttacac attcatggaa agacatcaac gcagagtgcc tctgcccaat caaggtccca      1680
atgcctcttc ttgcgcgagt tctcaatctt gcacgagtgc tttatgttat ataccaggat      1740
gaagacggct acactcattc tggaaccaag gtcaagaact ttgcaacctc agtgcttatc      1800
gattctatgc caatcaatta gaaaatgtaa caagacactg aagtggaggc ataaataaat      1860
tcaaaagttg gcttaaagtt gggctaaaaa aaaaaa                                 1897
```

<210> SEQ ID NO 5
<211> LENGTH: 491
<212> TYPE: PRT
<213> ORGANISM: Actinidia deliciosa

<400> SEQUENCE: 5

Met Gln Leu Pro Cys Ala Gln Ala Leu Pro Ile Pro Thr Val Thr Thr
1               5                   10                  15

Asn Thr Ser Ile Glu Pro Pro His Val Thr Arg Arg Ser Ala Asn Tyr
            20                  25                  30

His Pro Ser Ile Trp Gly Asp His Phe Leu Ala Tyr Ser Ser Asp Ala
        35                  40                  45

Met Glu Glu Asp Ile Asn Met Glu Gln Gln Arg Leu His His
    50                  55                  60

Leu Lys Gln Lys Val Arg Lys Met Leu Glu Ala Ala Glu Gln Ser
65                  70                  75                  80

Ser Gln Met Leu Asn Leu Val Asp Lys Ile Gln Arg Leu Gly Val Ser
                85                  90                  95

Tyr His Phe Glu Thr Glu Ile Glu Thr Ala Leu Arg His Ile Tyr Lys

```
                    100                 105                 110
Thr Cys Asp Tyr His Phe Asp Leu His Thr Ala Ala Leu Ser Phe
            115                 120                 125
Arg Leu Leu Arg Gln Gln Gly Tyr Pro Val Ser Cys Asp Met Phe Asp
130                 135                 140
Lys Phe Lys Asn Ser Lys Gly Glu Phe Gln Glu Ser Ile Ile Ser Asp
145                 150                 155                 160
Val Arg Gly Met Leu Ser Leu Tyr Glu Ala Thr Cys Leu Met Ile His
                165                 170                 175
Gly Glu Asp Ile Leu Asp Glu Ala Leu Ala Phe Thr Ile Thr Gln Leu
            180                 185                 190
Arg Ser Ala Leu Pro Asn Leu Ser Thr Pro Phe Lys Glu Gln Ile Ile
        195                 200                 205
His Ala Leu Asn Gln Pro Ile His Lys Gly Leu Thr Arg Leu Asn Ala
        210                 215                 220
Arg Ser His Ile Leu Phe Phe Glu Gln Asn Asp Cys His Ser Lys Asp
225                 230                 235                 240
Leu Leu Asn Phe Ala Lys Leu Asp Phe Asn Leu Leu Gln Lys Leu His
                245                 250                 255
Gln Arg Glu Leu Cys Glu Ile Thr Arg Glu Ile Ser Ala Leu Asp Gln
            260                 265                 270
Leu Pro Glu Tyr Met Lys Leu Cys Tyr Gln Ala Leu Leu Asp Val Tyr
        275                 280                 285
Ser Met Ile Asp Glu Glu Met Ala Lys Gln Gly Arg Ser Tyr Cys Val
        290                 295                 300
Asp Tyr Ala Lys Ser Ser Met Lys Ile Leu Val Arg Ala Tyr Phe Glu
305                 310                 315                 320
Glu Ala Lys Trp Phe His Gln Gly Tyr Val Pro Thr Met Glu Glu Tyr
                325                 330                 335
Met Gln Val Ala Leu Val Thr Ala Gly Tyr Lys Met Leu Ala Thr Ser
            340                 345                 350
Ser Phe Val Gly Met Gly Glu Leu Ala Thr Lys Glu Ala Phe Asp Trp
        355                 360                 365
Val Ser Asn Asp Pro Leu Ile Val Gln Ala Ala Ser Val Ile Gly Arg
        370                 375                 380
Leu Lys Asp Asp Ile Val Gly His Lys Phe Glu Gln Lys Arg Gly His
385                 390                 395                 400
Val Ala Ser Ala Val Glu Cys Tyr Ser Lys Gln His Gly Thr Thr Glu
                405                 410                 415
Glu Glu Ala Ile Ile Glu Leu Tyr Lys Gln Val Thr His Ser Trp Lys
            420                 425                 430
Asp Met Asn Ala Glu Cys Leu Cys Pro Thr Lys Val Pro Met Pro Leu
        435                 440                 445
Leu Ala Arg Val Leu Asn Leu Ala Arg Val Leu Tyr Val Ile Tyr Gln
        450                 455                 460
Asp Ala Asp Gly Tyr Thr His Ser Gly Thr Lys Val Lys Asn Phe Val
465                 470                 475                 480
Thr Ser Val Leu Ile Asp Ser Met Pro Ile Asn
                485                 490

<210> SEQ ID NO 6
<211> LENGTH: 565
<212> TYPE: PRT
<213> ORGANISM: Actinidia deliciosa
```

<400> SEQUENCE: 6

```
Met Gln Leu Pro Cys Ala Gln Ala Leu Pro Ile Pro Thr Val Thr Thr
1               5                   10                  15

Asn Thr Ser Ile Glu Pro Pro His Val Thr Arg Arg Ser Ala Asn Tyr
            20                  25                  30

His Pro Ser Ile Trp Gly Asp His Phe Leu Ala Tyr Ser Ser Asp Ala
        35                  40                  45

Met Glu Glu Asp Ile Asn Met Glu Gln Gln Arg Leu His His
50                  55                  60

Leu Lys Gln Lys Val Arg Lys Met Leu Glu Ala Ala Lys Gln Ser
65                  70                  75                  80

Ser Gln Met Leu Asn Leu Val Asp Lys Ile Gln Arg Leu Gly Val Ser
            85                  90                  95

Tyr His Phe Glu Thr Glu Ile Glu Thr Ala Leu Arg His Ile Tyr Lys
            100                 105                 110

Thr Cys Asp Tyr His Phe Asp Asp Leu His Thr Ala Ala Leu Ser Phe
            115                 120                 125

Arg Leu Leu Arg Gln Gln Gly Tyr Pro Val Ser Cys Asp Met Phe Gly
130                 135                 140

Lys Phe Lys Asn Cys Lys Gly Glu Phe Gln Glu Ser Ile Ile Ser Asp
145                 150                 155                 160

Val Arg Gly Met Leu Ser Leu Tyr Glu Ala Thr Cys Leu Arg Ile Arg
                165                 170                 175

Gly Glu Asp Ile Leu Asp Glu Ala Leu Ala Phe Thr Thr Thr Gln Leu
            180                 185                 190

Gln Ser Ala Leu Pro Asn Leu Ser Thr Pro Ile Lys Glu Gln Ile Ile
            195                 200                 205

His Ala Leu Asn Gln Pro Ile His Lys Trp Leu Thr Arg Leu Asp Ala
        210                 215                 220

Arg Arg His Ile Leu Phe Phe Glu Gln Asn Asp Cys His Gly Lys Asp
225                 230                 235                 240

Leu Leu Asn Phe Ala Lys Leu Asp Phe Asn Ser Leu Gln Lys Leu His
                245                 250                 255

Gln Arg Glu Leu Cys Glu Ile Thr Arg Trp Trp Lys Asp Leu Asp Phe
            260                 265                 270

Ala Lys Lys Leu Pro Phe Ala Arg Asp Arg Met Val Glu Cys Tyr Phe
            275                 280                 285

Trp Ile Leu Gly Val Tyr Phe Glu Pro Gln Tyr Leu Arg Ala Arg Arg
            290                 295                 300

Met Leu Thr Lys Val Ile Ala Leu Thr Ser Ile Ile Asp Asp Ile Tyr
305                 310                 315                 320

Asp Val Tyr Gly Thr Leu Glu Glu Leu Val Leu Phe Thr Asp Ala Ile
                325                 330                 335

Glu Arg Trp Glu Ile Ser Ala Leu Asp Asn Leu Pro Asp Tyr Met Lys
            340                 345                 350

Leu Cys Tyr Gln Ala Leu Leu Asp Val Tyr Ser Met Ile Asp Glu Glu
            355                 360                 365

Met Ala Lys Gln Gly Arg Ser Tyr Cys Val Asp Tyr Ala Lys Ser Ser
            370                 375                 380

Met Lys Ile Leu Val Arg Ala Tyr Phe Glu Glu Ala Lys Trp Phe His
385                 390                 395                 400

Gln Gly Tyr Val Pro Thr Met Glu Glu Tyr Met Gln Val Ala Leu Val
```

-continued

```
                405                 410                 415
Thr Ala Gly Tyr Lys Met Leu Ala Thr Ser Ser Phe Val Gly Met Gly
        420                 425                 430

Glu Leu Ala Thr Lys Glu Ala Phe Asp Trp Val Ser Asn Asp Pro Leu
            435                 440                 445

Ile Val Gln Ala Ala Ser Val Ile Gly Arg Leu Lys Asp Asp Ile Val
        450                 455                 460

Gly His Lys Phe Glu Gln Lys Arg Gly His Val Ala Ser Ala Val Glu
465                 470                 475                 480

Cys Tyr Ser Lys Gln His Gly Thr Ile Glu Glu Ala Ile Ile Glu
                485                 490                 495

Leu Asp Lys Gln Val Thr His Ser Trp Lys Asp Ile Asn Ala Glu Cys
            500                 505                 510

Leu Cys Pro Ile Lys Val Pro Met Pro Leu Leu Ala Arg Val Leu Asn
        515                 520                 525

Leu Ala Arg Val Leu Tyr Val Ile Tyr Gln Asp Glu Asp Gly Tyr Thr
        530                 535                 540

His Ser Gly Thr Lys Val Lys Asn Phe Ala Thr Ser Val Leu Ile Asp
545                 550                 555                 560

Ser Met Pro Ile Asn
                565

<210> SEQ ID NO 7
<211> LENGTH: 686
<212> TYPE: DNA
<213> ORGANISM: Actinidia chinensis

<400> SEQUENCE: 7
atcttattgc gtagactatg caaaatcttc aatgaaaagt ttggttagag catacttcga     60
agaagccaaa tggtttcacc aaggatatgt tccaactatg gaagagtata tgcaagttgc    120
aatagtaacc ggggcttaca aaattcttgc aaccacttcc tttgttggca tgggagagtt    180
ggcaaccaaa gaggtctttg attgggtgtc aaatgatcct ttaattgttc aagctgcatc    240
aattgtttcc agactcacgg atgacattgt tggccacaag tttgagcaaa agagagggca    300
cgtggcatcg gcggttgaat gctacatgaa gcaacatggt acaacagagg aagaggccat    360
tgttgaattg tataagcaag ttacaaatgc atggaaagac atgaatgcag agtgcctctt    420
ccccaccaag gtcccaatgc ctcttctcgt gagagttctc aatcttgcac gagtgattaa    480
tgttctatac aaggatgaag atggctacac tcattcaaga accaaggtta agaaatttgt    540
gacctcagtg cttgtagatt ttgtgccgat cagctagcaa acgttcctct ctaccacatg    600
ttaattagtc tgcttgctaa tgcagtttac taatatgaaa tttaataaat gcgtattttc    660
caataaagga atttaaaaaa aaaaaa                                         686

<210> SEQ ID NO 8
<211> LENGTH: 190
<212> TYPE: PRT
<213> ORGANISM: Actinidia chinensis

<400> SEQUENCE: 8

Tyr Cys Val Asp Tyr Ala Lys Ser Ser Met Lys Ser Leu Val Arg Ala
1               5                   10                  15

Tyr Phe Glu Glu Ala Lys Trp Phe His Gln Gly Tyr Val Pro Thr Met
                20                  25                  30

Glu Glu Tyr Met Gln Val Ala Ile Val Thr Gly Ala Tyr Lys Ile Leu
```

-continued

Ala Thr Thr Ser Phe Val Gly Met Gly Glu Leu Ala Thr Lys Glu Val
 50                  55                  60

Phe Asp Trp Val Ser Asn Asp Pro Leu Ile Val Gln Ala Ala Ser Ile
 65                  70                  75                  80

Val Ser Arg Leu Thr Asp Asp Ile Val Gly His Lys Phe Glu Gln Lys
                 85                  90                  95

Arg Gly His Val Ala Ser Ala Val Glu Cys Tyr Met Lys Gln His Gly
             100                 105                 110

Thr Thr Glu Glu Glu Ala Ile Val Glu Leu Tyr Lys Gln Val Thr Asn
         115                 120                 125

Ala Trp Lys Asp Met Asn Ala Glu Cys Leu Phe Pro Thr Lys Val Pro
130                 135                 140

Met Pro Leu Leu Val Arg Val Leu Asn Leu Ala Arg Val Ile Asn Val
145                 150                 155                 160

Leu Tyr Lys Asp Glu Asp Gly Tyr Thr His Ser Arg Thr Lys Val Lys
                165                 170                 175

Lys Phe Val Thr Ser Val Leu Val Asp Phe Val Pro Ile Ser
            180                 185                 190

<210> SEQ ID NO 9
<211> LENGTH: 755
<212> TYPE: DNA
<213> ORGANISM: Vaccinium corymbosum

<400> SEQUENCE: 9

```
ggaagccaaa tggtttcatg aaggttatgt tccgagtatg gaagagtata tgagagttgc      60
actggttacc ggtgcttaca aaatgcttgc aaccacttct tttgttggca tggggattt      120
ggtgaccaaa gaggcctttg aatgggtgtc aagtgatcct ttaattgttg aagctgcatc     180
cgtgatttgc agactcatgg atgatatggc aggccacaag tttgagcaag agagggaca    240
cgtggcttcg gcagttgaat gctacatgaa acaacatggt gcaacacaag aagtggttct    300
tcttgaattt aaaaaaagag ttacaaatgc atggaaagac atgaacgcag agtgcctccg    360
cccaactgcc gttccaatgc ctctcctcac ccgagttctc aatctcgcac gagtgatcaa    420
tgttatatac aaggatgaag atgggtacac tcattctgga acaaagctca gaactttgt    480
aatctcagtg cttatcgatt ctgtgccgat caattagcaa acagtagtcc taacttaaat    540
aatctgttgg cttataactt tataagtgtc gtgaaatgtt ctagtgaact tggtaaggat    600
gtatttccga tatgtagctc tatctccact gtacggttgt aatcttgctc tcttctacta    660
agaaagctca ttaatcgctg cttaaaatgt aaagccaact tgctcaagtt tatcgtcaaa    720
caagttctgt tttacgattt tgttggaaa aaaaa                                755
```

<210> SEQ ID NO 10
<211> LENGTH: 171
<212> TYPE: PRT
<213> ORGANISM: Vaccinium corymbosum

<400> SEQUENCE: 10

Glu Ala Lys Trp Phe His Glu Gly Tyr Val Pro Ser Met Glu Glu Tyr
 1               5                  10                  15

Met Arg Val Ala Leu Val Thr Gly Ala Tyr Lys Met Leu Ala Thr Thr
                20                  25                  30

Ser Phe Val Gly Met Gly Asp Leu Val Thr Lys Glu Ala Phe Glu Trp
             35                  40                  45

```
Val Ser Ser Asp Pro Leu Ile Val Glu Ala Ala Ser Val Ile Cys Arg
     50                  55                  60

Leu Met Asp Asp Met Ala Gly His Lys Phe Glu Gln Glu Arg Gly His
 65                  70                  75                  80

Val Ala Ser Ala Val Glu Cys Tyr Met Lys Gln His Gly Ala Thr Gln
                 85                  90                  95

Glu Val Val Leu Leu Glu Phe Lys Lys Arg Val Thr Asn Ala Trp Lys
                100                 105                 110

Asp Met Asn Ala Glu Cys Leu Arg Pro Thr Ala Val Pro Met Pro Leu
            115                 120                 125

Leu Thr Arg Val Leu Asn Leu Ala Arg Val Ile Asn Val Ile Tyr Lys
130                 135                 140

Asp Glu Asp Gly Tyr Thr His Ser Gly Thr Lys Leu Lys Asn Phe Val
145                 150                 155                 160

Ile Ser Val Leu Ile Asp Ser Val Pro Ile Asn
                165                 170

<210> SEQ ID NO 11
<211> LENGTH: 26
<212> TYPE: DNA
<213> ORGANISM: Synthetic primer

<400> SEQUENCE: 11
gaattccaac taccttgtgc tcaagc                                     26

<210> SEQ ID NO 12
<211> LENGTH: 25
<212> TYPE: DNA
<213> ORGANISM: Synthetic primer

<400> SEQUENCE: 12
ctcgagcctc cacttcagtg tcttg                                      25

<210> SEQ ID NO 13
<211> LENGTH: 20
<212> TYPE: DNA
<213> ORGANISM: Synthetic primer

<400> SEQUENCE: 13
caattgagag gtgggagatc                                            20

<210> SEQ ID NO 14
<211> LENGTH: 20
<212> TYPE: DNA
<213> ORGANISM: Synthetic primer

<400> SEQUENCE: 14
gttggaacat atccttggtg                                            20

<210> SEQ ID NO 15
<211> LENGTH: 20
<212> TYPE: DNA
<213> ORGANISM: Synthetic primer

<400> SEQUENCE: 15
taggcgtgtc ttaccatttt                                            20

<210> SEQ ID NO 16
<211> LENGTH: 20
<212> TYPE: DNA
```

```
<213> ORGANISM: Synthetic primer

<400> SEQUENCE: 16
gcatgaatga tttgttcctt                                        20
``` the invention claimed is:

1. An isolated polynucleotide encoding a multifunctional germacrene-D synthase, wherein the polynucleotide sequence is set forth in SEQ ID NO:1.

2. A genetic construct comprising the polynucleotide of claim 1.

3. A vector comprising a genetic construct of claim 2.

4. An isolated polynucleotide encoding a multifunctional germacrene-D synthase having the amino acid sequence of SEQ ID NO:2.

5. A genetic construct comprising the polynucleotide of claim 4.

6. The genetic construct of claim 5 further comprising a promoter sequence.

7. The genetic construct of claim 6 further comprising a termination sequence.

8. A vector comprising a genetic construct of claim 5.

* * * * *